(12) United States Patent
Begriche et al.

(10) Patent No.: US 12,342,877 B2
(45) Date of Patent: Jul. 1, 2025

(54) CONDUCTIVE BAND FOR BIOSENSING GARMENTS

(71) Applicant: HONEYWELL SAFETY PRODUCTS USA, INC., Fort Mill, SC (US)

(72) Inventors: Aldjia Begriche, Montreal (CA); Payam Lazemi, Montreal (CA); Maria Elina Nurkka, Verdun (CA); Thierry Dumont, Montreal (CA); Pascal Fortier-Poisson, Brossard (CA)

(73) Assignee: Honeywell Safety Products USA, Inc., Charlotte, NC (US)

( * ) Notice: Subject to any disclaimer, the term of this patent is extended or adjusted under 35 U.S.C. 154(b) by 242 days.

(21) Appl. No.: 17/963,780

(22) Filed: Oct. 11, 2022

(65) Prior Publication Data

US 2023/0035612 A1 Feb. 2, 2023

Related U.S. Application Data

(60) Division of application No. 15/966,912, filed on Apr. 30, 2018, now Pat. No. 11,497,255, which is a
(Continued)

(51) Int. Cl.
*B32B 5/02* (2006.01)
*A41C 3/00* (2006.01)
(Continued)

(52) U.S. Cl.
CPC ............ *A41D 1/005* (2013.01); *A41C 3/0057* (2013.01); *A41D 13/1281* (2013.01);
(Continued)

(58) Field of Classification Search
CPC .............. A41C 3/0057; A41D 1/005; A41D 13/1281; A41F 15/002; A61B 2562/0209;
(Continued)

(56) References Cited

U.S. PATENT DOCUMENTS 4,580,572 A 4/1986 Granek et al.
6,341,504 B1 1/2002 Istook
(Continued)

FOREIGN PATENT DOCUMENTS

CA 2877802 A1 1/2014
CN 1976804 A 6/2007
(Continued)

OTHER PUBLICATIONS

CN Office Action Mailed on Feb. 25, 2022 for CN Application No. 201680073065.
(Continued)

*Primary Examiner* — Lawrence D Ferguson
(74) *Attorney, Agent, or Firm* — Alston & Bird LLP

(57) ABSTRACT

Embodiments described herein relate generally to wearable electronic biosensing garments. In some embodiments, an apparatus comprises a biosensing garment and a plurality of electrical connectors that are mechanically fastened to the biosensing garment. A plurality of printed electrodes is disposed on the biosensing garment, each being electrically coupled, via a corresponding conductive pathway, to a corresponding one of the plurality of electrical connectors. The apparatus can further include an elongate member including a conductive member that is coupled to a plurality of elastic members in a curved pattern and that is configured to change from a first configuration to a second configuration as the elongate member stretches. The change from the first configuration to the second configuration can result in a change of inductance of the conductive member.

20 Claims, 57 Drawing Sheets

Related U.S. Application Data continuation of application No. PCT/CA2016/051274, filed on Nov. 2, 2016.

(60) Provisional application No. 62/264,580, filed on Dec. 8, 2015, provisional application No. 62/261,465, filed on Dec. 1, 2015, provisional application No. 62/258,338, filed on Nov. 20, 2015, provisional application No. 62/249,721, filed on Nov. 2, 2015.

(51) Int. Cl.

| | |
|---|---|
| A41D 1/00 | (2018.01) |
| A41D 13/12 | (2006.01) |
| A41F 15/00 | (2006.01) |
| A61B 5/00 | (2006.01) |
| A61B 5/25 | (2021.01) |
| A61B 5/282 | (2021.01) |
| A61B 5/296 | (2021.01) |
| A63B 24/00 | (2006.01) |
| B32B 5/26 | (2006.01) |
| B32B 27/12 | (2006.01) |
| B32B 27/40 | (2006.01) |
| D02G 3/44 | (2006.01) |
| H05K 1/02 | (2006.01) |
| H05K 1/03 | (2006.01) |

(52) U.S. Cl.
CPC .............. *A41F 15/002* (2013.01); *A61B 5/25* (2021.01); *A61B 5/282* (2021.01); *A61B 5/296* (2021.01); *A61B 5/6804* (2013.01); *A63B 24/0062* (2013.01); *B32B 5/02* (2013.01); *B32B 5/26* (2013.01); *B32B 27/12* (2013.01); *B32B 27/40* (2013.01); *D02G 3/441* (2013.01); *H05K 1/0283* (2013.01); *H05K 1/038* (2013.01); *A61B 2562/0209* (2013.01); *A61B 2562/043* (2013.01); *A61B 2562/125* (2013.01); *A61B 2562/166* (2013.01); *A61B 2562/227* (2013.01); *A63B 2230/04* (2013.01); *A63B 2230/06* (2013.01); *A63B 2230/42* (2013.01); *A63B 2230/60* (2013.01); *B32B 2307/202* (2013.01); *B32B 2437/00* (2013.01); *B32B 2457/00* (2013.01); *D10B 2501/02* (2013.01); *H05K 2201/10151* (2013.01); *H05K 2201/10189* (2013.01); *H05K 2201/10287* (2013.01); *H05K 2201/10401* (2013.01)

(58) Field of Classification Search
CPC ........ A61B 2562/043; A61B 2562/125; A61B 2562/166; A61B 2562/227; A61B 5/25; A61B 5/282; A61B 5/296; A61B 5/6804; A63B 2230/04; A63B 2230/06; A63B 2230/42; A63B 2230/60; A63B 24/0062; B32B 2307/202; B32B 2437/00; B32B 2457/00; B32B 27/12; B32B 27/40; B32B 5/02; B32B 5/26; D02G 3/441; D10B 2501/02; H05K 1/0283; H05K 1/038; H05K 2201/10151; H05K 2201/10189; H05K 2201/10287; H05K 2201/10401
See application file for complete search history.

(56) References Cited

U.S. PATENT DOCUMENTS

| | | | |
|---|---|---|---|
| 7,025,596 B2* | 4/2006 | Zollo | H01R 12/7076 |
| | | | 428/102 |
| 10,530,083 B2* | 1/2020 | Dumont | H05K 3/361 |
| 11,497,255 B2* | 11/2022 | Begriche | A61B 5/296 |
| 2005/0067402 A1 | 3/2005 | Green et al. | |
| 2006/0281382 A1 | 12/2006 | Karayianni et al. | |
| 2008/0196783 A1 | 8/2008 | Van Bruggen et al. | |
| 2011/0094785 A1 | 4/2011 | Howell et al. | |
| 2011/0143562 A1 | 6/2011 | Wu et al. | |
| 2014/0187900 A1 | 7/2014 | Pernu et al. | |
| 2014/0305536 A1 | 10/2014 | Gao et al. | |
| 2014/0318699 A1 | 10/2014 | Longinotti-Buitoni et al. | |

FOREIGN PATENT DOCUMENTS

| | | |
|---|---|---|
| CN | 101827967 A | 9/2010 |
| CN | 102713037 A | 10/2012 |
| CN | 103597133 A | 2/2014 |
| CN | 103908047 A | 7/2014 |
| CN | 104582517 A | 4/2015 |
| DE | 102011111061 A1 | 2/2013 |
| WO | 03/60449 A1 | 7/2003 |
| WO | 2014/001577 A1 | 1/2014 |
| WO | 2014/165997 A1 | 10/2014 |
| WO | 2015/078451 A1 | 6/2015 |

OTHER PUBLICATIONS

CN Office Action Mailed on Jul. 3, 2020 for CN Application No. 201680073065.
CN Office Action Mailed on May 11, 2021 for CN Application No. 201680073065.
CN Office Action Mailed on Oct. 11, 2021 for CN Application No. 201680073065.
CN Office Action Mailed on Oct. 17, 2022 for CN Application No. 201680073065.
English Translation of CN Office Action Mailed on Feb. 25, 2022 for CN Application No. 201680073065.
English Translation of CN Office Action Mailed on May 11, 2021 for CN Application No. 201680073065.
English Translation of CN Office Action Mailed on Oct. 11, 2021 for CN Application No. 201680073065.
International Search Report and Written Opinion mailed Dec. 5, 2016 for International Application No. PCT/CA2016/051274, 15 pages.
Non-Final Office Action received for U.S. Appl. No. 15/966,912, mailed on Mar. 1, 2022, 8 pages.
Notice of Allowance received for U.S. Appl. No. 15/966,912, mailed on Jul. 12, 2022, 7 pages.
Office Action for Chinese Patent Application No. 201680073065.6 dated Jul. 3, 2020, 17 pages.
Office Action issued in Chinese Application No. 201680073065.6 on May 11, 2021, 18 pages.
Office Action issued in Chinese Application No. 201680073065.6 on Oct. 11, 2021, 17 pages.
Requirement for Restriction/Election Mailed on May 18, 2021 for U.S. Appl. No. 15/966,912.
CN Office Action Mailed on Jan. 18, 2023 for CN Application No. 201680073065.
English Translation of CN Office Action Mailed on Jan. 18, 2023 for CN Application No. 201680073065.
CA Office Action Mailed on Jan. 24, 2023 for CA Application No. 3002253, 5 page(s).
CA Office Action Mailed on Nov. 20, 2023 for CA Application No. 3002253, 4 page(s).
CA Office Action Mailed on Sep. 24, 2024 for CA Application No. 3002253, 4 page(s).

* cited by examiner

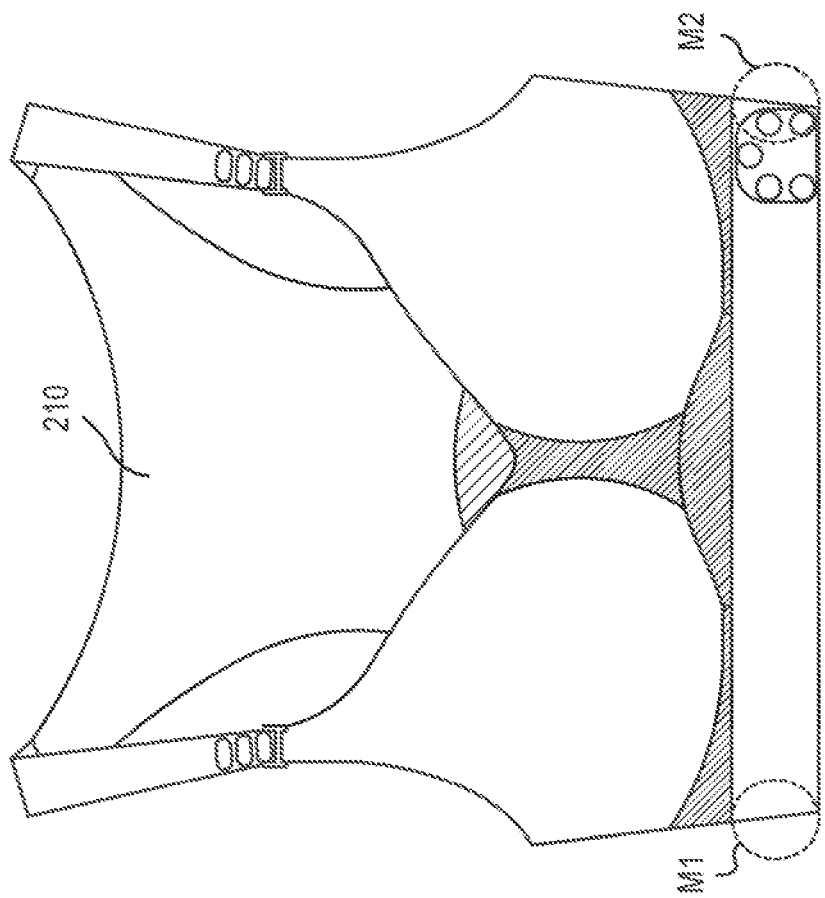
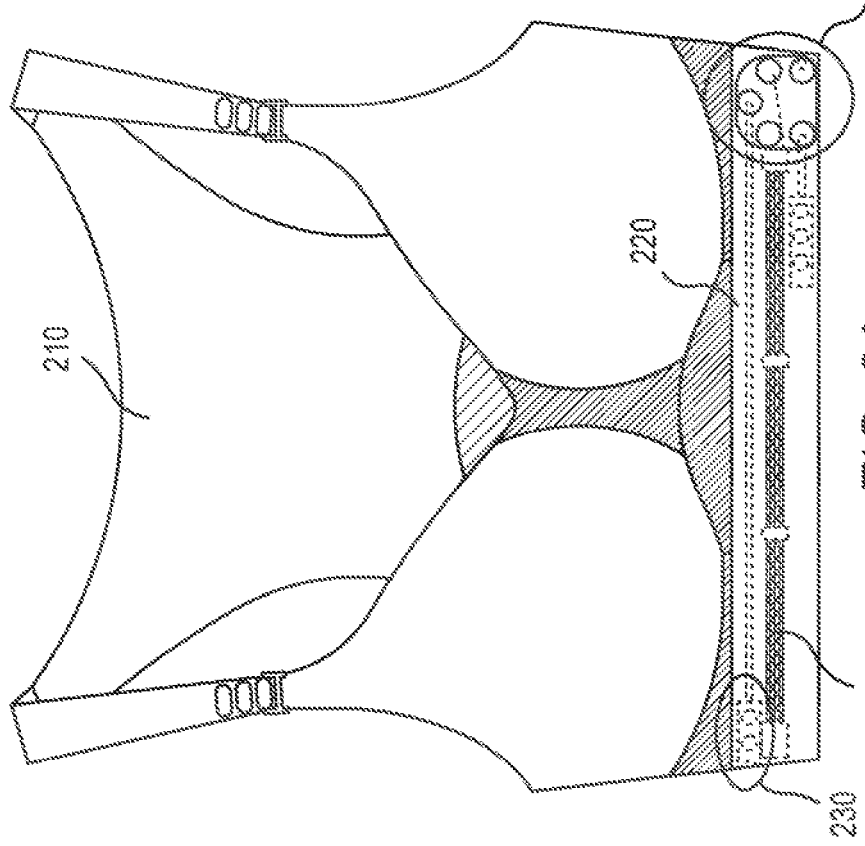
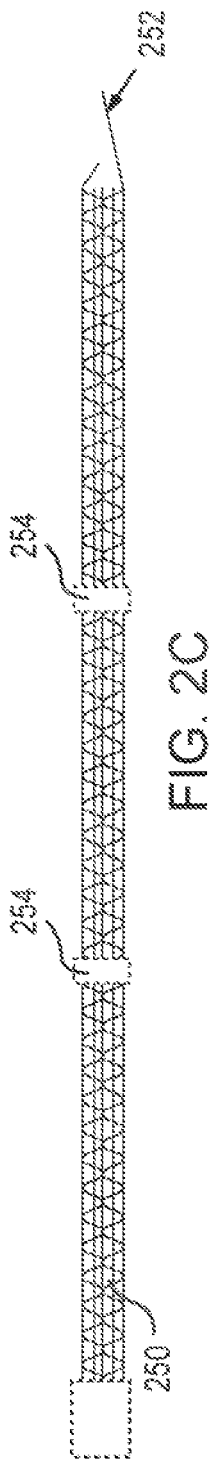
FIG. 2A
FIG. 2B
FIG. 2C

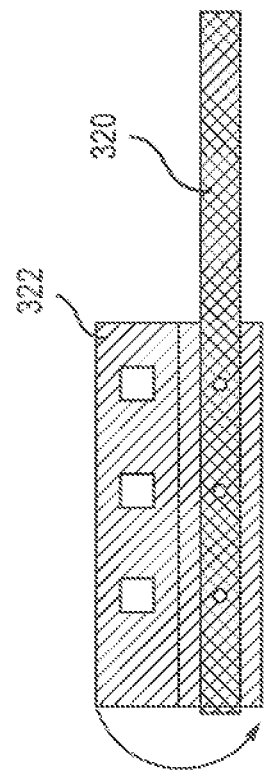
FIG. 4A
FIG. 4B
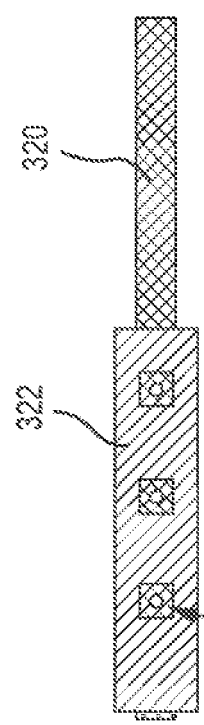
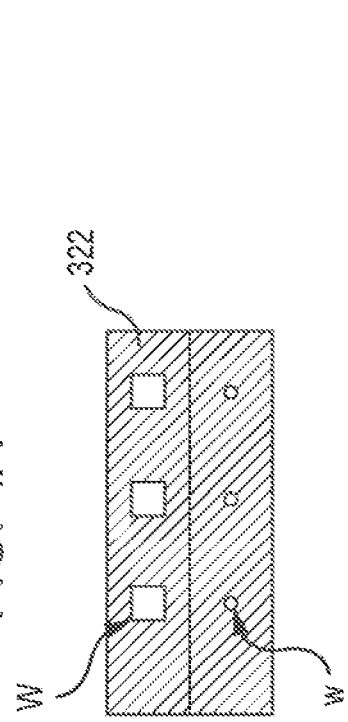
FIG. 4C
FIG. 4D
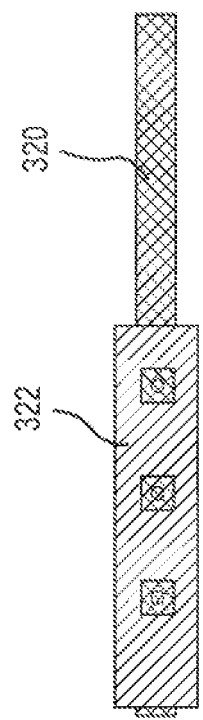

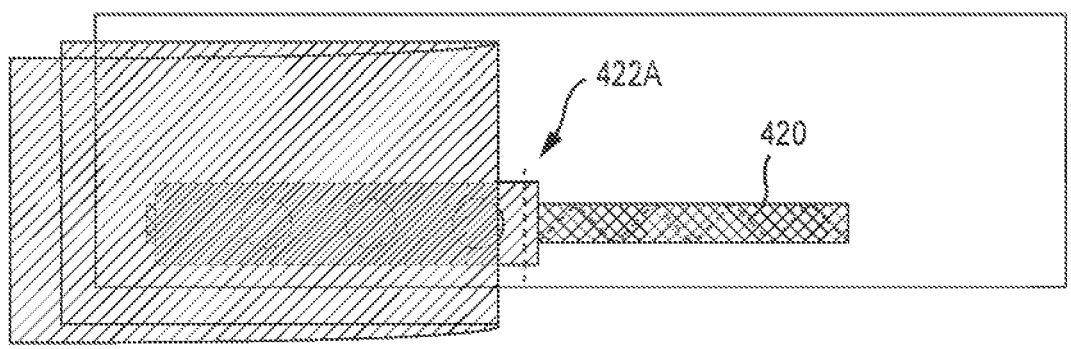
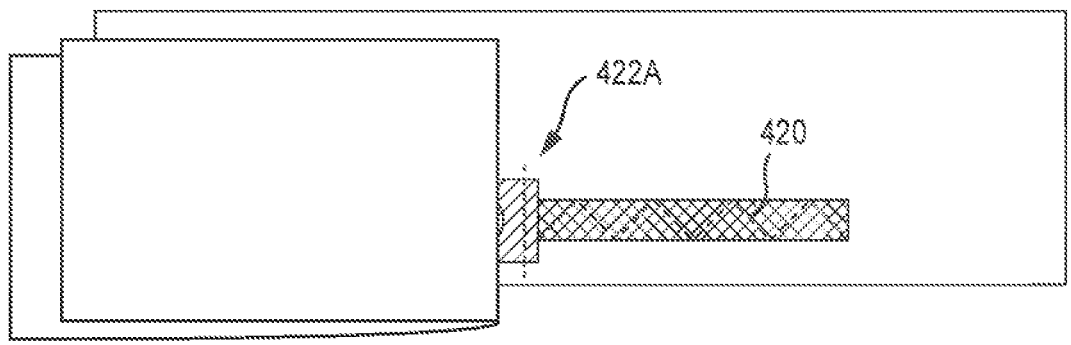
FIG. 5B

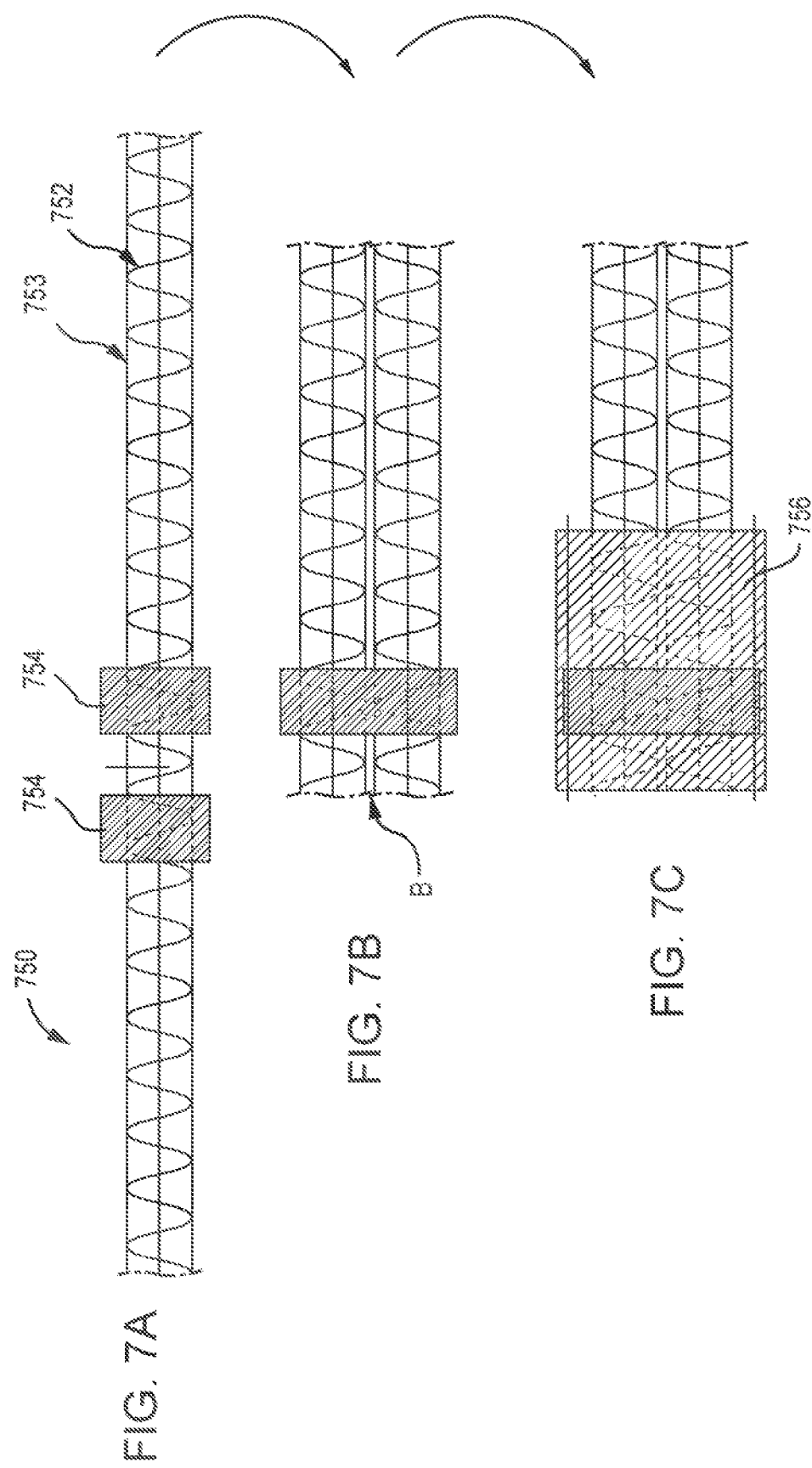

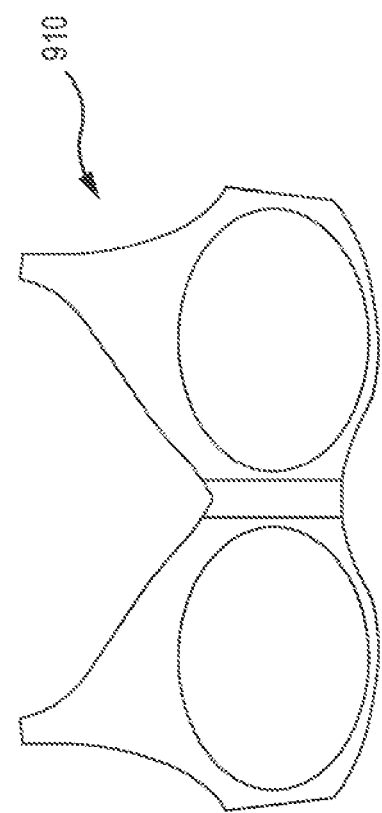
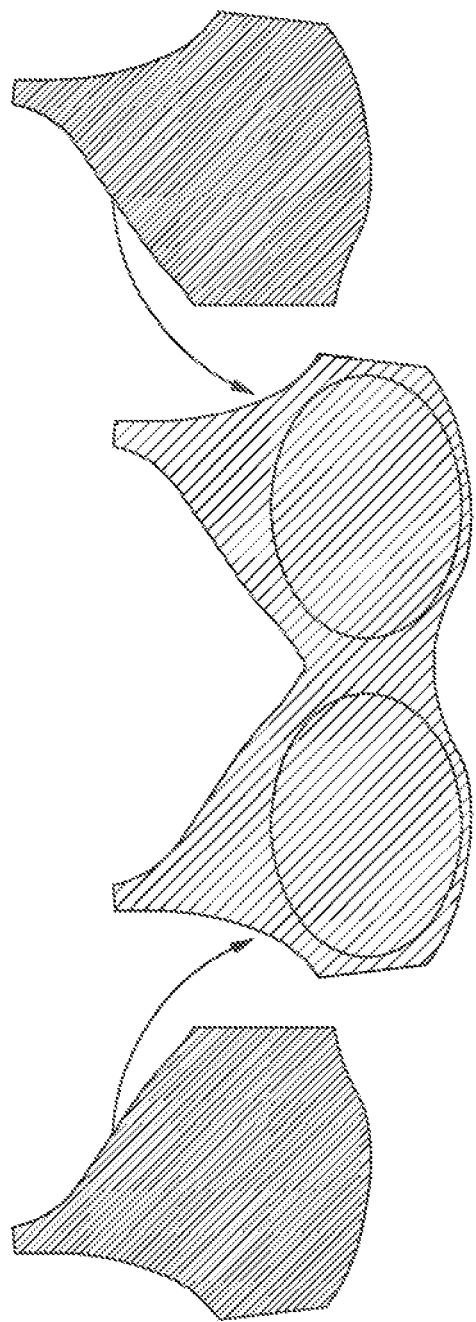
FIG. 9A
FIG. 9B

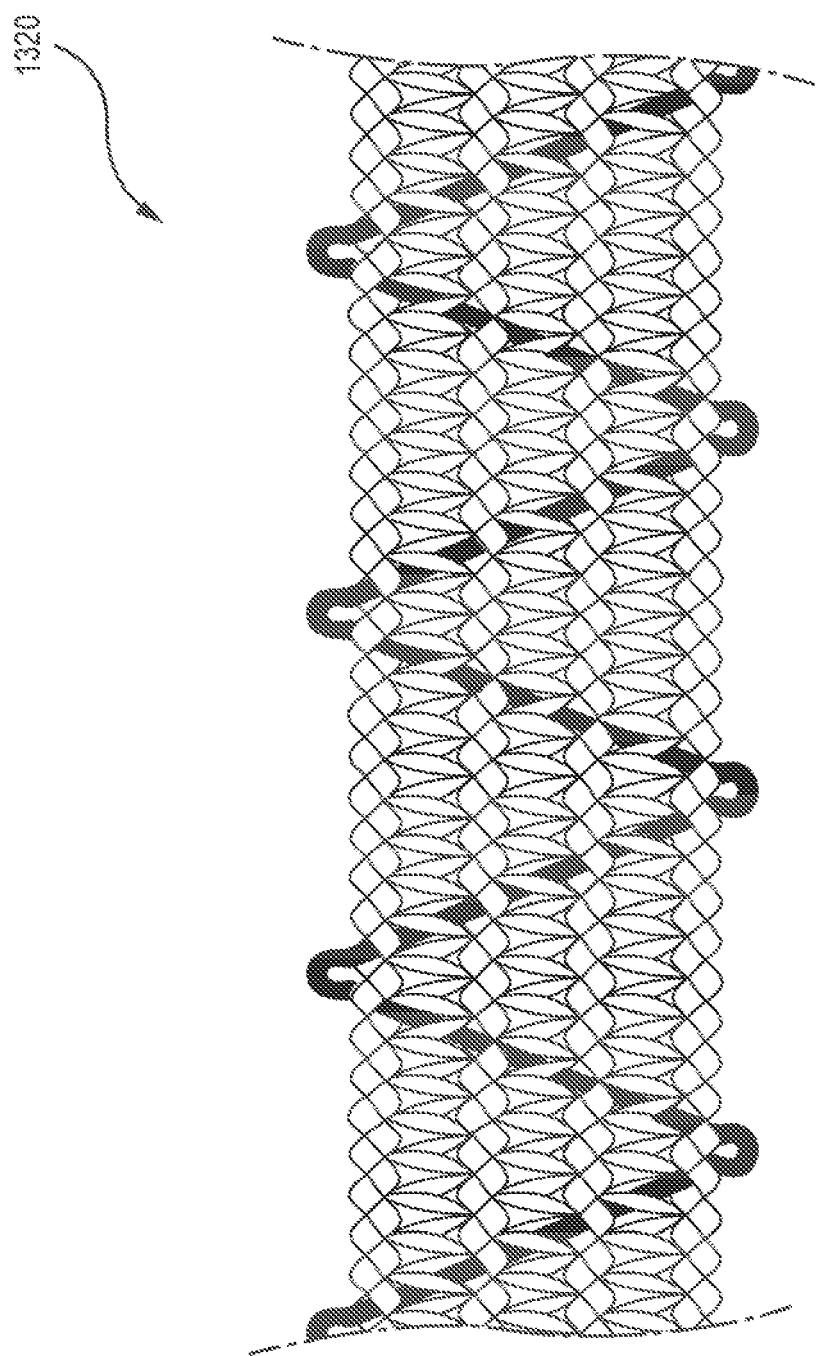

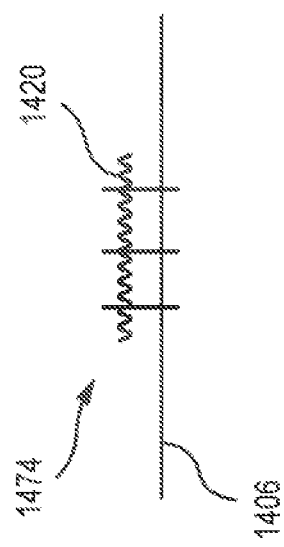

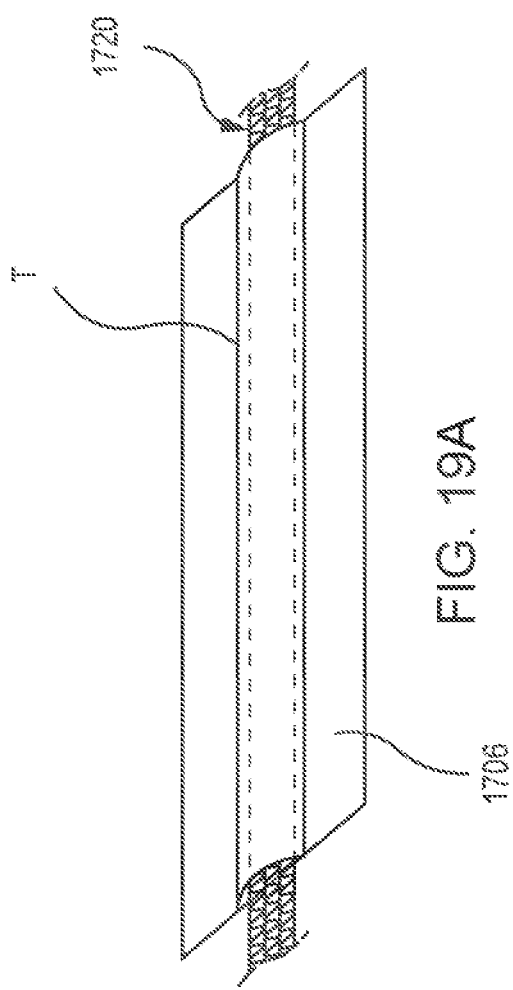
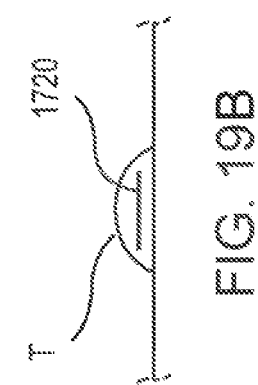

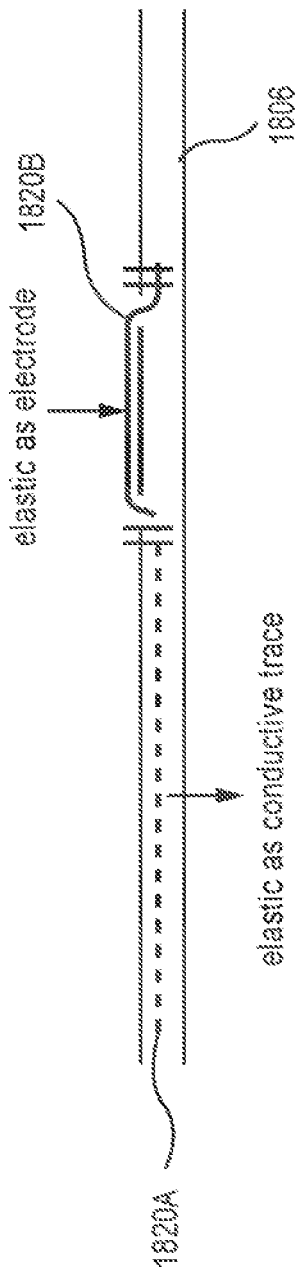

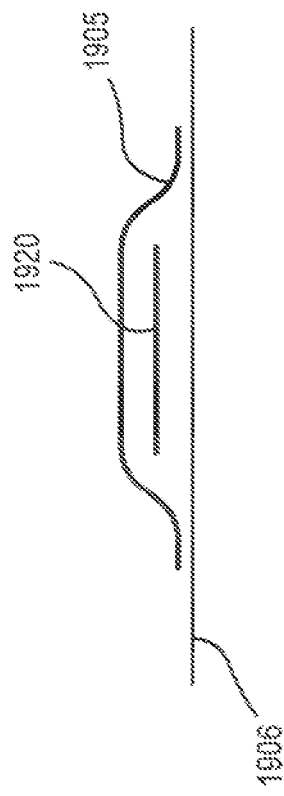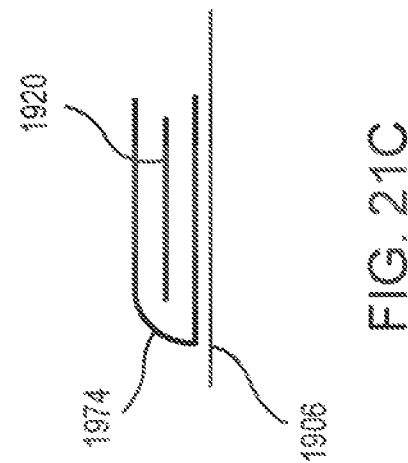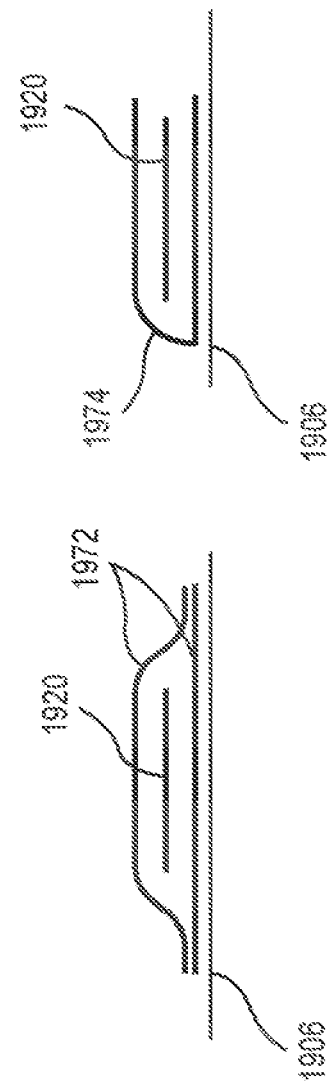

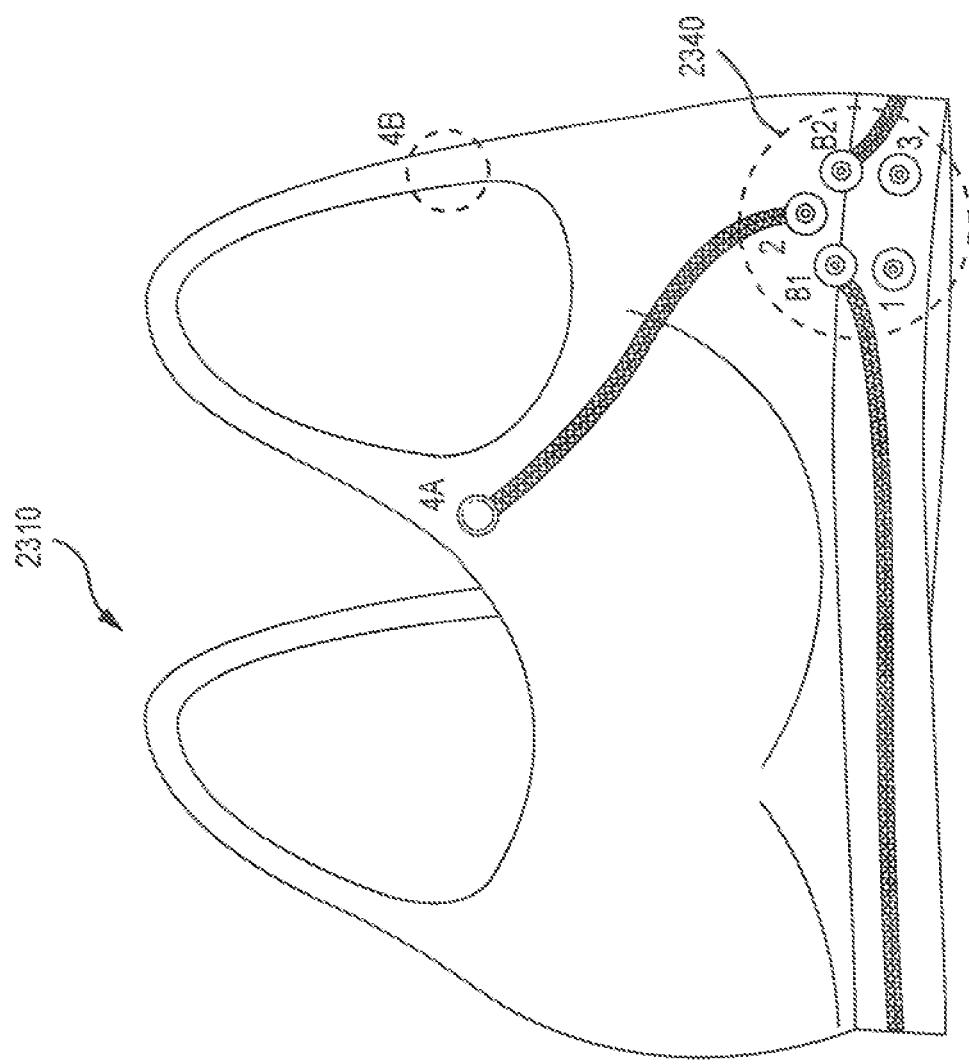

CONDUCTIVE BAND FOR BIOSENSING GARMENTS

CROSS-REFERENCE TO RELATED APPLICATIONS

This application is a division of U.S. Non-Provisional patent application Ser. No. 15/966,912, filed Apr. 30, 2018 and entitled "Biosensing Garment," which was a continuation of International Patent Application Serial No. PCT/CA2016/051274, filed Nov. 2, 2016 and entitled "Systems and Methods for Monitoring Respiration in a Biosensing Garment," and also claims priority to, and the benefit of, U.S. Provisional Patent Application Ser. No. 62/264,580, filed on Dec. 8, 2015 and entitled "Biosensing Garment," U.S. Provisional Patent Application Ser. No. 62/261,465 filed on Dec. 1, 2015 and entitled "Printed Electrodes," U.S. Provisional Patent Application Ser. No. 62/258,338 filed on Nov. 20, 2015 and entitled "Electrode System for Wearable Electronic Applications," and U.S. Provisional Patent Application Ser. No. 62/249,721 filed on Nov. 2, 2015 and entitled "Conductive Elastic Band for Wearable Electronic Applications," the entire disclosures of each of which are hereby incorporated herein by reference in their entireties for all purposes.

BACKGROUND

The adoption of wearable consumer electronics, or "smart clothing," is currently on the rise. Biosensing garments, a subset of wearable electronics, are designed to interface with a wearer of the garment, and to determine information such as the wearer's heart rate, rate of respiration, activity level, body positioning, etc. Such properties can be measured via a sensor assembly that contacts the wearer's skin and that receive signals from the wearer's body. Through these sensor assemblies, signals are transmitted to one or more sensors and/or microprocessors for transduction, analysis, etc. A drawback of many biosensing garments on the market today, however, is that they do not achieve acceptable signal quality (e.g., the signal is too noisy). Also, many biosensing garments contain bulky electronic hardware, wires, and other components that can make them uncomfortable to the wearer. As such, there is a general need for biosensing garments with improved performance and/or that are more comfortable to wear.

SUMMARY

Embodiments described herein relate generally to wearable electronic biosensing garments. In some embodiments, an apparatus comprises a biosensing garment and a plurality of electrical connectors that are mechanically fastened to the biosensing garment. A plurality of printed electrodes is disposed on the biosensing garment, each being electrically coupled, via a corresponding conductive pathway, to a corresponding one of the plurality of electrical connectors. The apparatus can further include an elongate member including a conductive member that is coupled to a plurality of elastic members in a curved pattern and that is configured to change from a first configuration to a second configuration as the elongate member stretches. The change from the first configuration to the second configuration can result in a change of inductance of the conductive member.

BRIEF DESCRIPTION OF THE DRAWINGS

FIG. 2A shows a front view of a biosensing garment and internal components thereof, according to an embodiment.

FIG. 2B shows a further front view of the biosensing garment of FIG. 2A, with internal components hidden.

FIG. 2C shows an elongate member suitable for use in the biosensing garment of FIG. 2A.

FIGS. 4A-4D show an assembly process, according to an embodiment.

FIGS. 5A-5C show an assembly process, according to an embodiment.

FIGS. 7A-7C show an assembly/folding process, according to an embodiment.

FIG. 9A shows an inner mesh lining and molded cups of a biosensing garment, according to an embodiment.

FIG. 9B shows the inner mesh lining of FIG. 9A with an outer lining fabric sewn onto it.

FIG. 15 is a detail view of the conductive band of FIG. 14.

FIG. 16A is a cross-sectional view of a conductive band that is laminated to a substrate, according to an embodiment.

FIG. 16B is a cross-sectional view of a conductive band that is bonded to a substrate, according to an embodiment.

FIG. 16C is a cross-sectional view of a conductive band that is stitched to a substrate, according to an embodiment.

FIG. 19A is a perspective view of a conductive band disposed within a tunnel structure on a substrate, according to an embodiment.

FIG. 19B is an end view of the conductive band and tunnel of FIG. 19A.

FIG. 20 is a cross-sectional view of a conductive band disposed within a garment or portion thereof, with a portion of the conductive band exposed at a surface of the garment, according to an embodiment.

FIGS. 21A-21C are cross-sectional views of a conductive band that is laminated to a substrate, according to some embodiments.

FIG. 28A shows a biosensing garment including an electrode array, according to an embodiment.

DETAILED DESCRIPTION

Figure 1:
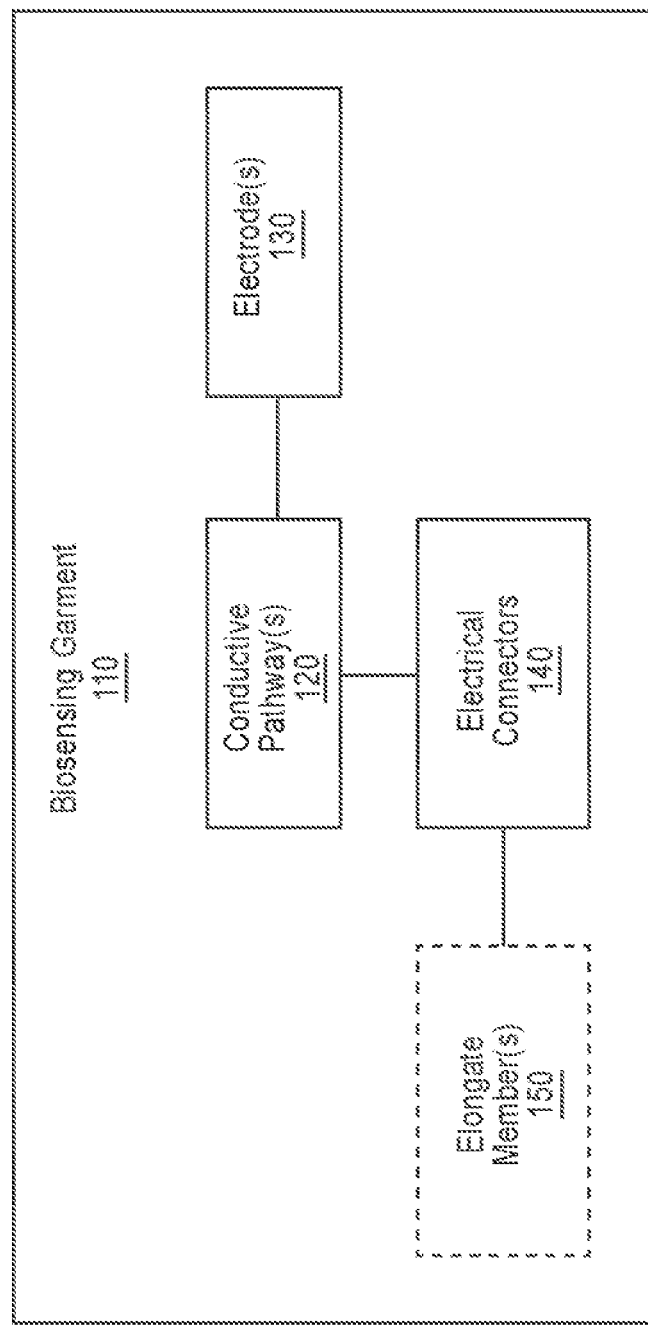
FIG. 1 is a schematic block diagram of a biosensing garment, according to an embodiment.

Wearable electronics such as biosensing garments (end the electronic textiles from which they are made) are subjected to different mechanical stresses than traditional electronic systems. For example, biosensing garments may be stretched during enrobing, disrobing, and wear (e.g., during physical activity of the wearer). This stretching can result in deformation of conductors and/or sensor elements that are embedded within and/or secured to a surface of the biosensing garment. As a result, wearable electronics often suffer from compromised performance after only a limited period of use. Additionally, biosensing garment electrodes designed to contact a wearer's skin are often prone to shift during activity, resulting in inconsistent signal strength and/or intermittent signal reliability. Existing textile-based electrodes used in biosensing applications can also be limited in their performance due to high skin-electrode impedance, sensitivity to motion artifacts, and poor signal-to-noise ratio.

In the present disclosure, biosensing garments including improved conductor and electrode configurations are described that result in improved signal quality, durability and reliability. Some embodiments described herein include a scalable metal-based electrode system, a carbon based electrode system, or configurations that overcomes disadvantages commonly associated with other textile-based electrodes, both in dry environments and in moist environments (e.g., in the presence of sweat). Embodiments described herein achieve increased design flexibility, increased measurement surface area for signal detection, increased degree of redundancy, increased resistance to movement artifacts, increased flexibility, and adaptability to variation in body shapes. Bio-sensing garments described herein can include functionality for a variety of applications, such as electro-cardiography (ECG), electromyography (EMG), impedance pneumography (IP) or respiratory inductance plethysmography (RIP)), for example to derive breathing rate from an ECG signal, such as from heart rate variability (HRV) or R peak amplitude (i.e., the maximum amplitude in the R wave deflection of an ECG). Conductors and electrodes of the present disclosure can be integrated into any type of garment/textile or other bio-sensing assembly. Electrodes described herein can be connected directly to any type of conductive pathway, such as a wire, knitted conductive trace, conductive elastic band, and/or the like.

Embodiments described herein relate generally to wearable electronic biosensing garments. In some embodiments, an apparatus comprises a biosensing garment and a plurality of electrical connectors that are mechanically fastened to the biosensing garment. A plurality of printed electrodes is disposed on the biosensing garment, each being electrically coupled, via a corresponding conductive pathway, to a corresponding one of the plurality of electrical connectors. The apparatus can further include an elongate member including a conductive member that is coupled to a plurality of elastic members in a curved pattern and that is configured to change from a first configuration to a second configuration as the elongate member stretches. The change from the first configuration to the second configuration can result in a change of inductance of the conductive member.

In other embodiments, an apparatus comprises a biosensing garment and a plurality of electrical connectors that are mechanically fastened to the biosensing garment. In some such embodiments, at least one array (e.g., a configuration, cluster, arrangement, and/or the like) of rivet or snap electrodes is electrically coupled, via a conductive pathway, to a corresponding one of the plurality of electrical connectors, and each rivet or snap electrode of the electrode array is mechanically fastened to the biosensing garment. The apparatus can further include an elongate member including a conductive member coupled to a plurality of elastic members in a curved pattern that is configured to change from a first configuration to a second configuration as the elongate member stretches. The change from the first configuration to the second configuration can result in a change of inductance of the conductive member.

Turning now to FIG. 1, a schematic block diagram of a biosensing garment, according to an embodiment, is shown. Specifically, a biosensing garment 110 includes one or more conductive pathways 120 electrically connecting one or more electrodes 130 to a plurality of respective electrical connectors 140. One or more elongate members 150 are also optionally connected to respective electrical connectors of the plurality of electrical connectors 140. A biosensing garment 110 can comprise a shirt, brassiere (e.g., a "sports bra," as discussed further herein, for example with reference to FIGS. 2A-2C below), shorts, pants, arm or leg sleeve, jacket/coat, glove, armband, headband, hat/cap, collar, wristband, stocking, sock, shoe, or any other wearable garment or portion thereof, or a segment of fabric that has not yet been fashioned into a wearable form. In some embodiments, the conductive pathway(s) 120 are conductive elastic bands, for example, including a plurality of elastic filaments disposed substantially parallel to one another and mechanically coupled to one another by one or more conductive and/or non-conductive filaments that are knitted or woven about the elastic filaments. In other embodiments, either additionally or alternatively, the conductive pathway(s) 120 include one or more wires, conductive traces, metallizations, printed conductors, conductive laminates, and/or the like. Examples of conductive pathways include one or more conductive bands as disclosed in further detail herein. In some embodiments, an electrode 130 is an electrode that is screen printed, inkjet printed, transfer printed, sublimation printed, pad printed, coated, transfer coated, sprayed, or extruded onto a surface of the biosensing garment. For example, the electrode 130 can be formed from one or more conductive inks, conductive pastes and/or conductive coatings, or any combination thereof. An ink suitable for use in forming an electrode 130 can be silver, carbon, or graphene based. In other words, a conductive ink may include particles (e.g., microparticles and/or nanoparticles), flakes, threads, filaments, etc. In some embodiments, an electrode 130 includes a conductive polymer. In other embodiments, each electrode 130 is an array that includes a plurality of electrodes that are mechanically secured to the biosensing garment (e.g., by virtue of a snap-cap, press-fit, or other type of connection through a fabric of the biosensing garment, optionally also including a lamination or adhesive layer and/or stitching, as discussed in greater detail below). Each such electrode of an electrode array can comprise a rivet, a snap cap, a socket, a pin, a stud, a post (e.g., an S-spring, ring-spring, prong type), a cover button, and/or the like. As defined herein, an "electrode array" is a plurality of individual electrodes in any configuration, where the electrodes of the plurality of electrodes may or may not be evenly spaced or distributed. In some embodiments, the electrode 130 includes a two-dimensional arrangement of electrodes that can be symmetric or asymmetric. In some embodiments, the electrode 130 includes a one-dimensional arrangement of electrodes that can be a single row or column. In some embodiments, the electrode 130 is a three-dimensional arrangement of electrodes. Each electrode can comprise a metal such as brass, stainless steel, or any other metal or other material that is biocompatible (i.e., that can be safely placed against the skin of a wearer of the biosensing garment), hypoallergenic and/or non-allergenic. Electrodes of the electrode 130 can all be of the same type, or can comprise any combination of electrodes described herein. Examples of suitable electrodes and electrode arrays are disclosed in further detail in sections herein. In some embodiments, the electrode 130, whether comprising an array of electrodes or a single electrode, is electrically coupled via a single/common conductive pathway to a respective one of the electrical connectors 140. The electrical connectors 140 collectively comprise/define a biosensing garment connector region, for example that is configured to interface with a transmitter or other communications or measurement device (e.g., to measure and/or process biological signals collected via the biosensing garment). Each connector of the electrical connectors 140 can comprise a rivet, snap cap, socket, pin, and/or the like, and the plurality of electrical connectors can comprises connectors that are all of the same type, or any combination thereof.

The optional elongate member(s) 150 can include a RIP sensor, for example including a conductive member that is mechanically coupled (e.g., via knitting, weaving, threading, twisting, folding, wrapping, braiding, adhesion, or any other method of attachment) to a plurality of elastic members in a curved pattern that is configured to change from a first configuration to a second configuration as the elongate member stretches, said change from the first configuration to the second configuration resulting in a change of inductance of the conductive member. Examples of elongate members can be found in International Application PCT/CA2016/051034, titled "Systems and Methods for Monitoring Respiration in a Biosensing Garment", incorporated by reference herein. In some embodiments, an elongate member is not included in the biosensing garment 110. In some embodiments, one elongate member is included in the biosensing garment 110. In some embodiments, multiple elongate members are included in the biosensing garment 110. Each said elongate member 150 is electrically coupled, e.g., via the conductive member of a RIP sensor, to a corresponding pair of the electrical connectors 140 (i.e., to two of the plurality of electrical connectors 140). In some embodiments, each connector of the electrical connectors 140 is electrically connected to only one component within the biosensing garment (i.e., to an electrode 130 or to an elongate member 150).

In some embodiments, a biosensing garment 110 includes three ECG electrode arrays, each including three round rivets having a diameter of about 9 mm. The rivets are connected to conductive pathway 120 comprising an approximately 6 mm wide knitted conductive elastic band, the knitted conductive elastic band being knitted with 4 elastane monofilaments and a 2-ply X-Static yarn (i.e., a silver-clad polymeric fiber) or any other conductive filament (e.g., a metal-clad filament, strand, yarn, etc.).

In some embodiments, a conductive pathway 120 is knit using 4 elastomer filaments and 5 strands of conductive thread. Of the 5 strands of conductive thread, 1 is used to traverse across the width of the conductive pathway 120 to bind the elastomer filaments together, and 4 are used to stitch or knit around the elastomer fibers. In other embodiments, 8 strands of conductive thread are used instead of 5, 4 of which are used to traverse across the width of the conductive pathway 120 to bind the elastomer filaments together and to obtain improved coverage and higher conductivity/lower resistance, and 4 of which are used to stitch or knit around the elastomer fibers. In other embodiments, elastomer filaments can be wrapped with a conductive fiber or fibers (e.g., silver fibers).

In some embodiments, the biosensing garment 110 is a biosensing sports brassiere (or "sports bra") with ECG and/or breathing (e.g., RIP) sensors attached to a chest band of the biosensing sports bra, as described in greater detail below.

Figure 2D:
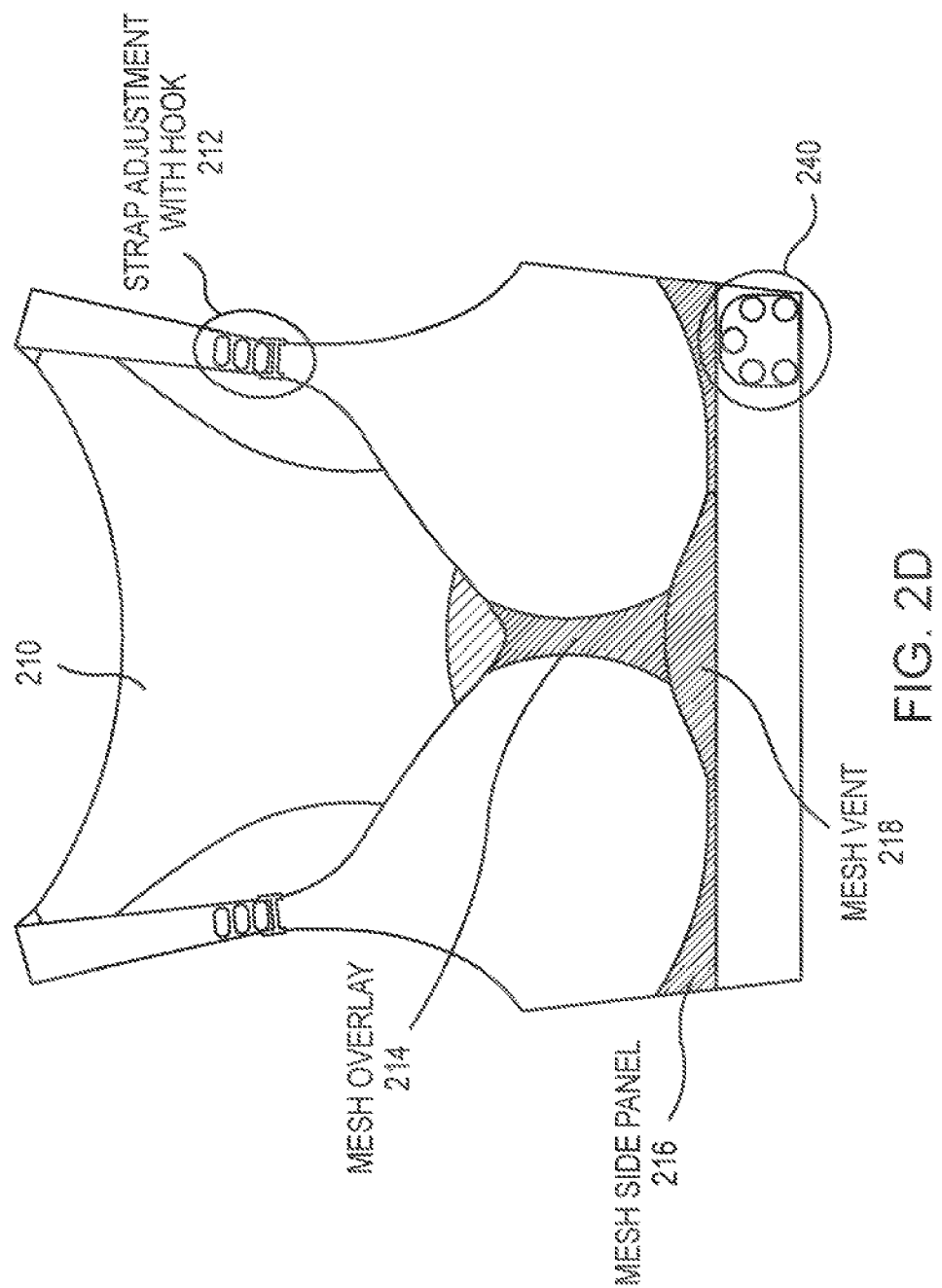
FIG. 2D shows a further front view of the biosensing garment of FIG. 2A, with labelling.

FIG. 2A shows a front view of a biosensing garment 210 and internal components thereof, according to an embodiment. Specifically, FIG. 2A shows a biosensing sports bra 210 having adjustable shoulder straps, a plurality of mesh reinforcement regions, a plurality of electrical connectors 240 (e.g., collectively defining a "biosensing garment connector region" configured to receive/interface with a transmitter or other communication or measurement device), two electrode arrays 230 each electrically connected, via a corresponding conductive pathway 220, to the biosensing garment connector region 240 (i.e., to a single corresponding connector of the biosensing garment connector region), and an elongate member 250. FIG. 2B shows a further front view of the biosensing garment of FIG. 2A, with internal components hidden. FIG. 2C shows an elongate member 250 (including attachment materials 254, for example comprising a thermoplastic polyurethane, "TPU") suitable for use in the biosensing garment of FIG. 2A. FIG. 2D shows a further front view of the biosensing garment of FIG. 2A, with labelling of the mesh regions (mesh overlay 214, mesh side panel 216, mesh vent 218) and strap adjustment 212 hardware. One or more of the mesh regions shown in FIG. 2D can be omitted, depending on the embodiment. Also, although the mesh regions in FIG. 2D are shown to be disposed between and beneath the bra cups, other configurations are also contemplated. For example, one or mesh regions can be placed in any region of the biosensing sports bra 210 (e.g., on all or part of the bra cup, on the backside, and/or on the chest band, etc.).

The biosensing sports bra of FIGS. 2A-2C includes a chest band having sufficient width (i.e., the vertical dimension as viewed in FIGS. 2A-2C) (e.g., about 2") to accommodate a plurality of sensing elements (i.e., the elongate member 250 and the electrode arrays 230/conductive pathways 220) and the plurality of electrical connectors 240. For such designs, where the sensing elements are disposed within the band, the upper portion of the biosensing sports bra can be altered freely and independent of (or without interfering with) the biosensing technology/elements. Although a 2" wide chest band may be needed and/or sufficient to accommodate some configurations/collections of hardware, embodiments with other hardware configurations (e.g., involving a different number and/or size of the hardware components) may invoke, allow or necessitate the use of a narrower or wider chest band.

The chest band has a hook and loop fastener in the back (see, e.g., FIG. 3), comprising a row of three hooks and a corresponding row of three loops to allow adjustment of the tightness of the band. Adjustability allows the band to be flexibly adjusted for different levels of intensity in training, and/or for different body shapes and sizes. The adjustability is also important to ensure that the band is fitted tightly enough to impart a desired level of compression, such that the electrodes come into/establish good electrical contact with the skin. With a compression level that is too low, in higher intensity movement, the electrodes can be prone to noise that can mask the ECG signal. In some embodiments, the preferred level of compression to maintain both a high level of wearer comfort and a good signal quality (even in high intensity movement), when measured at the side of the bra (see the circled regions in FIG. 2B), under the chest band, is about 15 mmHg. In some embodiments, the biosensing garment is configured to exert a compression force on a wearer that is higher than 15 mmHg (e.g., about 20 mmHg), without affecting the comfort. A wearer's sensitivity to compression can be subjective, and as such, the appropriate/desired levels of compression for different users can vary.

As shown in FIGS. 2A-2H and 3, two of the ECG electrode arrays 230 and their corresponding conductive pathways 220 are disposed on the front portion of the chest band: one close to the connector region, and one on the far right side (from the wearer's perspective). A third ECG electrode array 230 (e.g., a ground electrode array) and its corresponding conductive pathway can be disposed on the back portion of the chest band, in relatively close proximity to the connector region (see FIG. 3). While traditional heart rate monitors typically have 2 ECG electrodes on the chest that are placed very close to each other, such electrode placement reduces the reliability of signal detection. The closer the electrodes are to one another on a wearer's chest, the lower the R-peak amplitude is, such that distinguishing the targeted signal from noise becomes more difficult and can require signal amplification and/or additional signal processing. To increase the R-peak amplitude in systems described herein, the front electrodes are placed as far from each other as possible on the biosensing garment and, hence, make contact with a user's chest over as far apart a distance as possible during use. In some embodiments, a first electrode array is configured so as to contact a first lateral surface of the skin of a wearer (or a surface that is proximal to the first lateral surface of the skin of a wearer) and a second electrode array is configured so as to contact a second lateral surface, substantially opposite the first lateral surface, of the skin of a wearer (or a surface that is distal from the first lateral surface of the skin of a wearer). In some embodiments, a first electrode array is configured so as to contact a first medial surface of the skin of a wearer (or a surface that is proximal to the first medial surface of the skin of a wearer) and a second electrode array is configured so as to contact a second medial surface, substantially opposite the first medial surface, of the skin of a wearer (or a surface that is distal from the first medial surface of the skin of a wearer). The distance between first and second electrode arrays can be selected such the same electrode array placement can be used in all sizes of the bra, thereby significantly reducing the manufacturing complexity.

The elongate member 250 (e.g., a breathing/RIP sensor) is disposed between the 2 conductive pathways (e.g., conductive elastic, conductive traces, etc.) on the front portion of the chest band, and partially covers the front chest region.

The front (or first side) of the biosensing sports bra of FIGS. 2A-2D includes a mesh panel overlay 214 (e.g., applied as an overlay on top of the "body" or "self" fabric) in the center, as well as a mesh vent 218 at center front in the underbust area (i.e., the area beneath the bust region), and elongate mesh side panels 216 each extending from the center front mesh vent to the a respective side portion of the biosensing sports bra. The underbust mesh area can be shaped such that it adds support and stability to the underbust region and/or shaped (e.g., curved) as an aesthetic element. The front of the biosensing sports bra also has a slight V-shaped neckline. In some embodiments, all of the edges of the biosensing sports bra are finished with a binding comprising a soft elastic binding and/or a binding made from the "body" fabric itself. Mesh vents described herein can be configured to increase a moisture evaporation rate, or "breathability" of a biosensing garment (as compared with a garment that does not include a mesh vent). Mesh overlays described herein can be configured to increase stability and/or support of a biosensing garment (as compared with a garment that does not include a mesh overlay).

As used herein, the term "fabric" can refer to cotton, polyester, lycra, spandex, bamboo, gore-tex, nylon, polypropylene, tencel, wool, x-static, or any other man-made or natural textile or substrate suitable for use in biosensing applications and/or performance sports clothing.

The biosensing bra can include molded/padded bra cups that are stitched or otherwise affixed to an inner mesh lining, and are therefore "fully integrated." The fully integrated cups can be configured to provide a level of physical support (e.g., "medium" support) sufficient for most forms of exercises (e.g., high-impact exercise, such as running). Although fully integrated, the cups do not need to be removed for washing, and they do not become folded or creased during washing, but rather maintain their shape (e.g., more effectively than loose cups or removable cups do). Differently sized cups can be used for different breast sizes, e.g. A, B, C, D, etc. In some embodiments, fully integrated cups are configured to provide greater biomechanical support than loose cups, for example because they cannot move around inside the lining. In some embodiments, the biosensing bra can include removable pads (e.g., removable pads of different sizes, etc.).

Figure 2E:
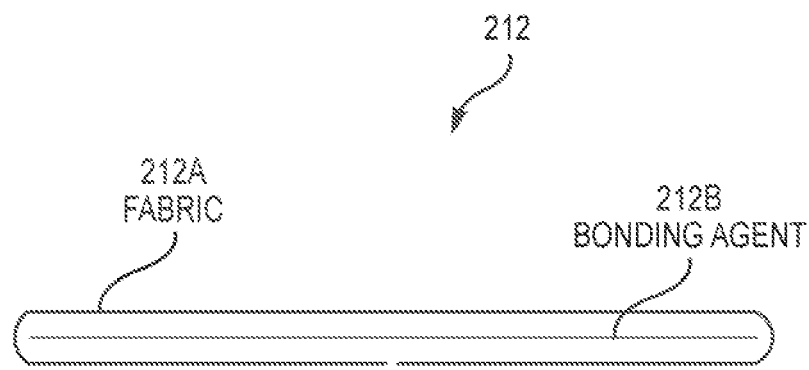
FIG. 2E shows a cross-section of a strap adjustment prior to attachment to a strap, according to an embodiment.
Figure 2F:
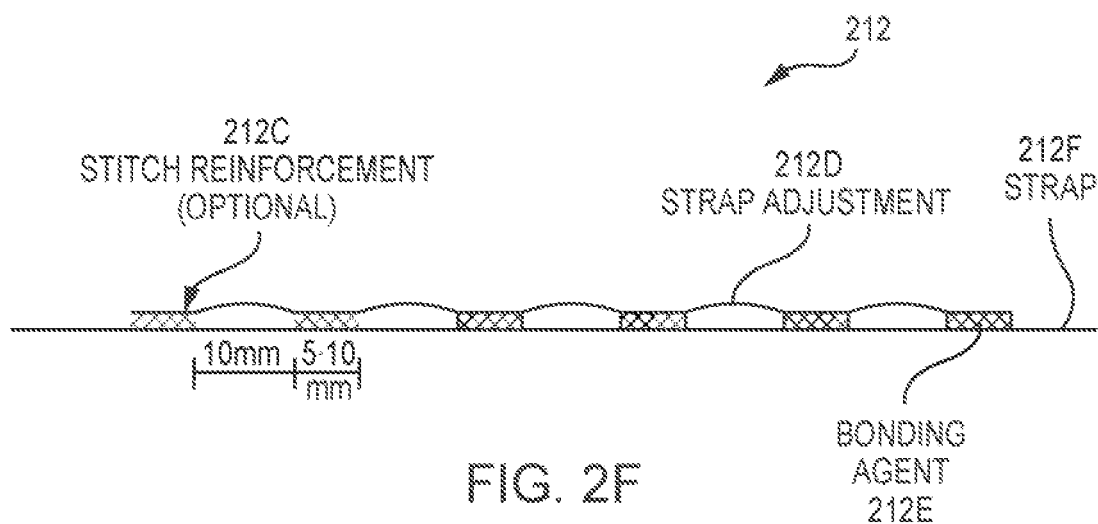
FIG. 2F shows a cross-section of the strap adjustment of FIG. 2E after attachment to a strap, according to an embodiment.
Figure 2G:
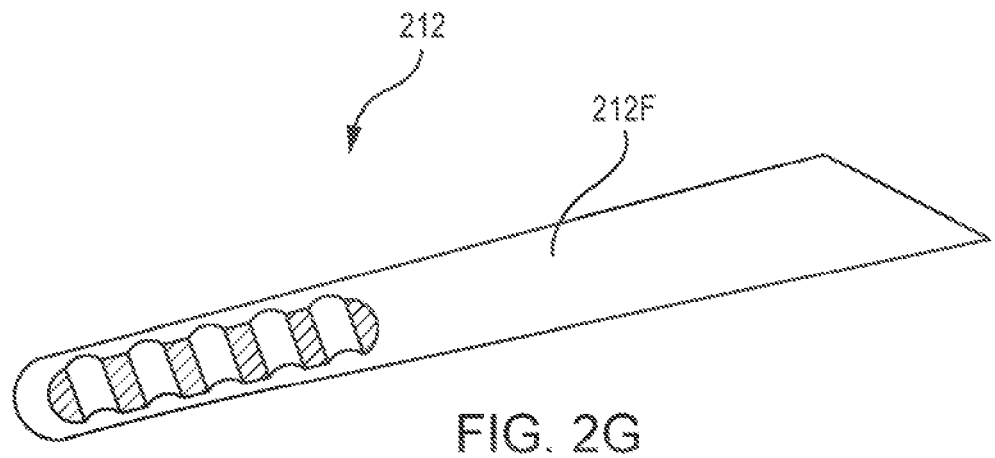
FIG. 2G shows a perspective view of an assembled strap adjustment, according to an embodiment.
Figure 2H:
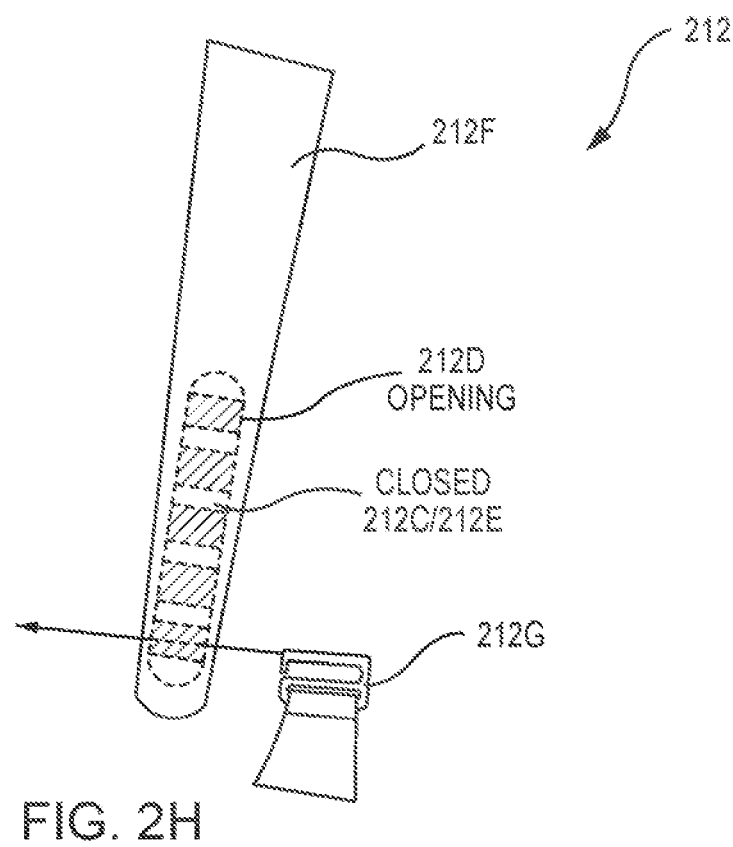
FIG. 2H shows a plan view of the assembled strap adjustment of FIG. 2F.

The straps of the biosensing bra 210 can be constructed by bonding a plurality of layers together with a heat adhesive thermoplastic (e.g., thermoplastic polyurethane, "TPU") film, and one or both said straps can include an adjustment element/mechanism 212 in the front (as shown in FIGS. 2A-2D) or in the back that connects to hooks that are attached to the biosensing bra body (the biosensing bra "body" including the cups, mesh(es), overlays, etc.). For example, in some embodiments, the strap adjustment 212 is constructed of a layered structure of the "self" fabric 212A and a thermoplastic adhesive film 212B as a bonding agent, such that the fabric with the film is folded underneath itself, as shown in FIG. 2E in cross-section. The strap adjustment 212 is attached onto the strap 212F, e.g., using a further thermoplastic adhesive film 212E, stitching 212C, and/or welding, leaving portions of the strap adjustment un-bonded, so as to create openings 212D (e.g., having a length of about 10 mm) for a hook to pass through, as shown in the cross-section of FIG. 2F. In some embodiments, each opening is approximately 10 mm wide, and bonded regions having a length of about 5-10 mm are disposed between the openings. The length of the bonded regions can vary according to the particular implementation, and can be uniform across the strap adjustment, or can vary. The strap adjustment can include a plurality of openings, such as 4 or 5, or as high as 7 or 8 to increase the range of adjustability in the strap. Perspective and plan views of the strap adjustment 212 are shown in FIGS. 2G and 2H, respectively. FIG. 2H shows an example hook and a direction of insertion (indicated by an arrow) into the strap adjustment 212.

Configuring the biosensing bra such that the adjustment element/mechanism is disposed in the front of the biosensing bra allows a wearer to readily adjust the straps while wearing the bra. The hook adjustment allows adjusting the tightness of the straps to either increase or decrease the level of support, and to better accommodate different breast sizes and body shapes. Also, when the adjustment element/mechanism is disposed in the front of the biosensing bra, the wearer is able to lie on her back without the hooks pressing against her body. Such a design is preferable to traditional bras that have metal hooks or sliders disposed on the straps in the back, which can cause pain to a wearer, e.g., when lying on her back.

A higher level of support may be desired in some applications, e.g. in high intensity or high impact sports such as running. The bonded strap construction allows for the use/combination of different materials, such that a strap with a limited level of elasticity can be achieved. Low elasticity in the straps of the biosensing bra can be desirable, for example, so that the strap is configured to more securely and reliably support the weight of the breast. In some embodiments, the strap is about 3 cm wide at the location on the strap that is configured to be disposed on the shoulder of a wearer during use, to allow a higher level of support, comfort, and stability than with a narrower strap. A wider strap distributes the weight of the breast that the strap is supporting to a wider area than with a narrower strap, thereby decreasing the pressure exerted per unit area, as well as the wearer's perceived pressure on the shoulder.

Figure 3:
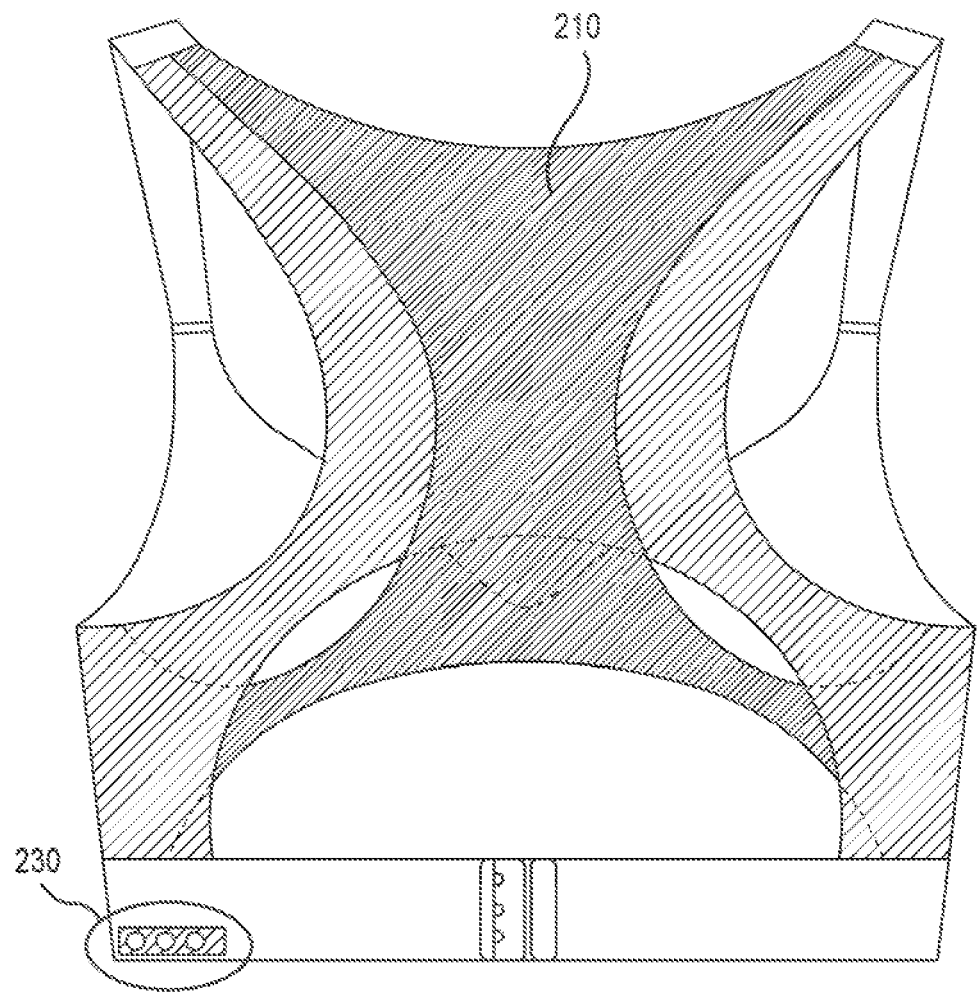
FIG. 3 shows a back view of the biosensing garment of FIG. 2A, showing internal components thereof.

FIG. 3 shows a back view of the biosensing garment of FIG. 2A, showing internal components thereof. Specifically, FIG. 3 shows an electrode array 230 disposed within/on a lower region of the chest band, and a racerback garment configuration including a racerback-shaped mesh reinforcement region.

FIGS. 4A-4D show an assembly process, according to an embodiment. Specifically, a heat adhesive TPU/barrier layer 322 is folded about a conductive pathway 320 (e.g., a conductive elastic) such that it encapsulates both sides of a segment of the conductive pathway. The TPU 322 includes a plurality of substantially square windows "W" and a corresponding plurality of smaller, substantially circular windows "w" defined therein (though other shapes and relative sizes are also contemplated), through which electrodes (e.g., rivets) of an electrode array are passed such that each said electrode makes electrical contact with the conductive pathway. The TPU 322 is folded about the conductive pathway 320 (as shown in FIG. 4B) such that the square windows "W" and the circular windows "w" align with one another. In some embodiments, an opening "O" is subsequently defined in the conductive pathway 320 (e.g., corresponding to the size/shape of the circular windows "w," as shown in FIG. 4D) so that one or more rivets of other connectors can more easily be disposed therein. In some embodiments, a plurality of apertures is defined in the conductive pathway 320 prior to the folding of the TPU 322, and the TPU 322 is then folded such that the square windows "W" and the circular windows "w" align with one another as well as with the apertures of the conductive pathway 320. In some embodiments, the larger holes are disposed on the side of the assembly where the bottoms of the rivets are passed though the conductive elastic.

Figure 5A:
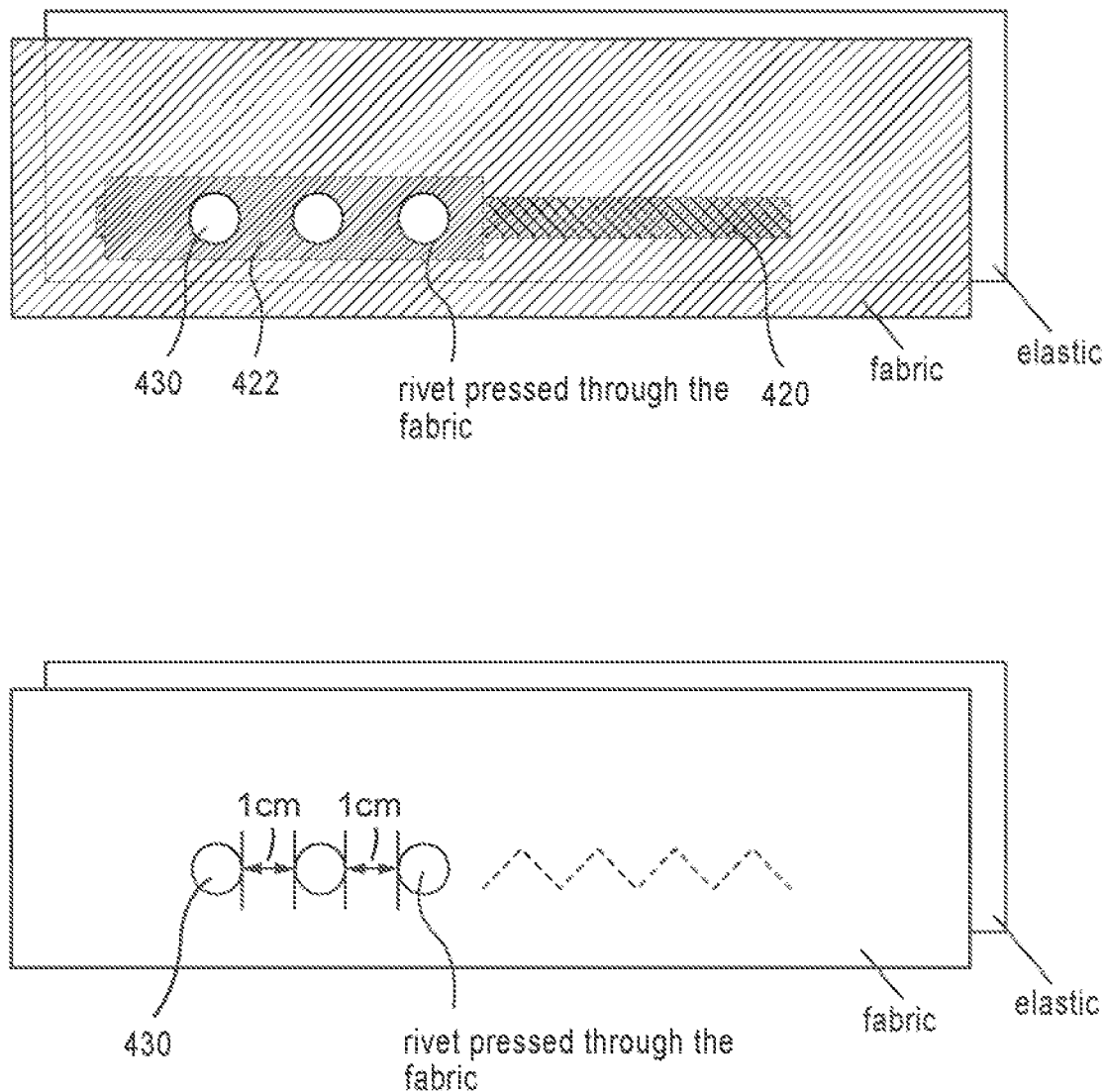
Figure 5C:
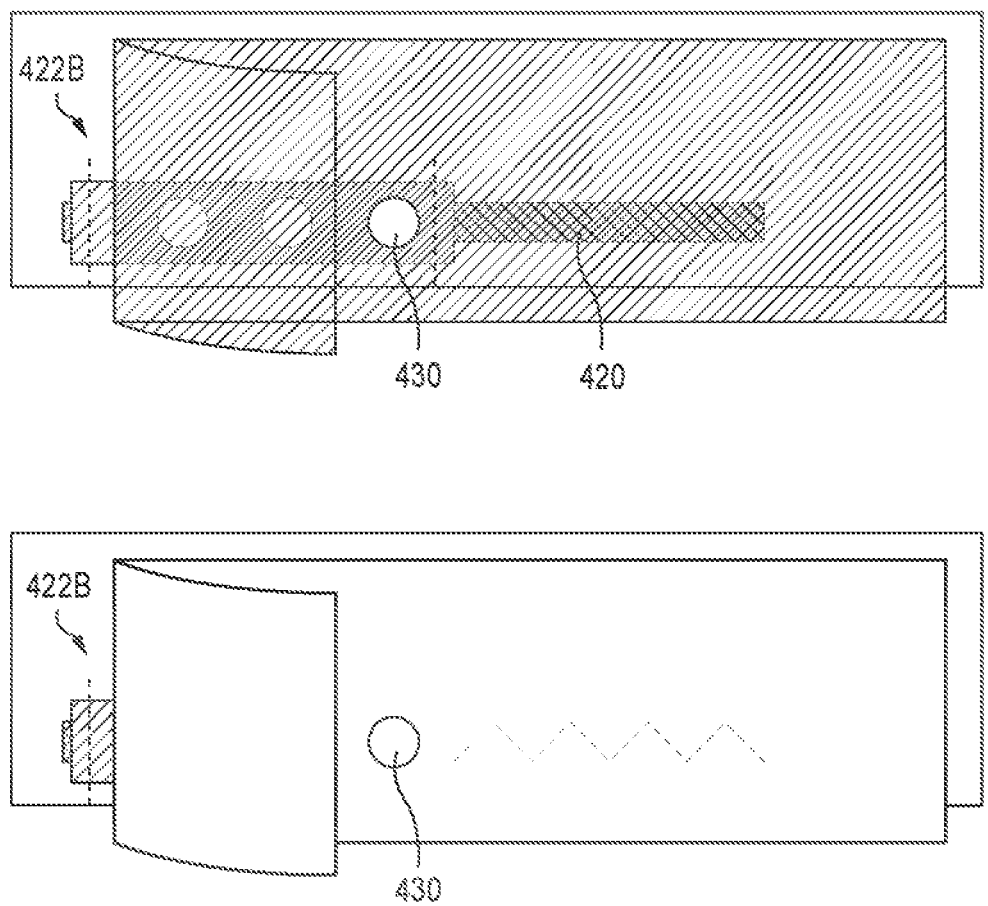

FIGS. 5A-5C show an assembly process, according to an embodiment. In each of FIGS. 5A-5C, the upper image shows elements of the assembly beneath the top fabric by making the top fabric semi-transparent, and the lower image shows the assembly of the upper image with the top fabric opaque. Specifically, FIG. 5A shows a conductive pathway 420 (e.g., a conductive elastic) that is secured, via zig-zag stitching, to a chest-band elastic, for example prior to attachment of the chest-band elastic to a fabric portion (e.g., of a garment). Other methods of attachment of the conductive pathway to the chest-band elastic are also contemplated, such as adhesive and/or other stitch patterns. In some embodiments, the conductive pathway 420 is not secured to, or is only partially secured to, the chest-band elastic. The conductive pathway 420 is partially encapsulated by a heat adhesive TPU/barrier layer 422, and each of three electrodes 430 (e.g., rivets) of a linear electrode array is attached to the TPU-encapsulated conductive pathway (e.g., as described in FIGS. 4A-4D). In FIG. 5B, a first end of the TPU layer (as well as the conductive pathway laminated therein) is secured to the chest-band elastic via linear stitching 422A beneath an outer fabric portion (e.g., of a garment) which has been folded back in a first direction, and in FIG. 5C, a second end of the TPU layer (as well as the conductive pathway laminated therein) is secured to the chest-band elastic via linear stitching 422B beneath a fabric portion (e.g., of a garment) which has been folded back in a second direction. Other methods of attaching the TPU/conductive pathway, such as adhesive and/or other stitch patterns, are also contemplated.

Figure 6A:
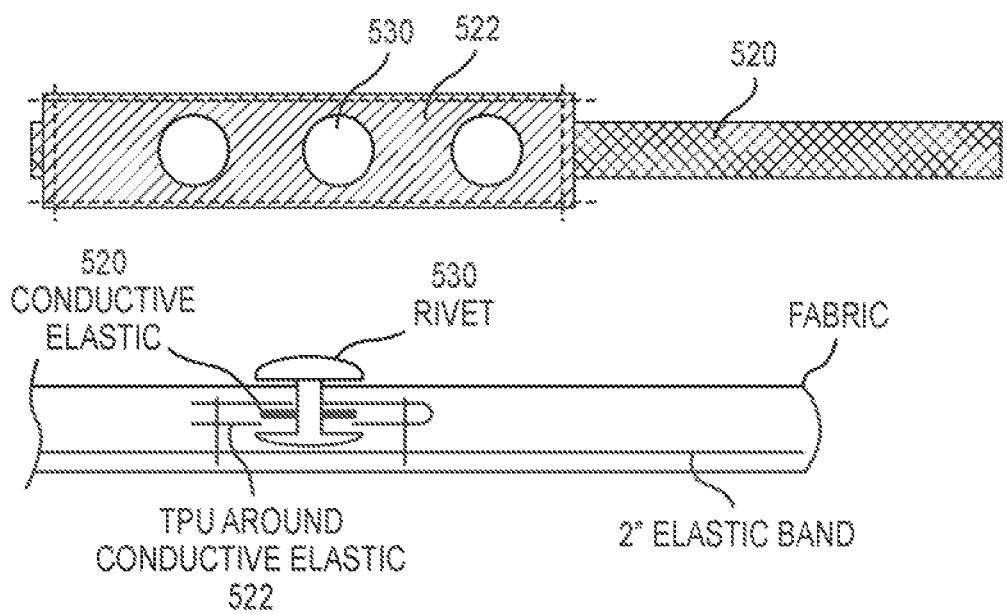
FIG. 6A shows plan and cross-section views of an example assembled electrode assembly, according to an embodiment.
Figure 6B:
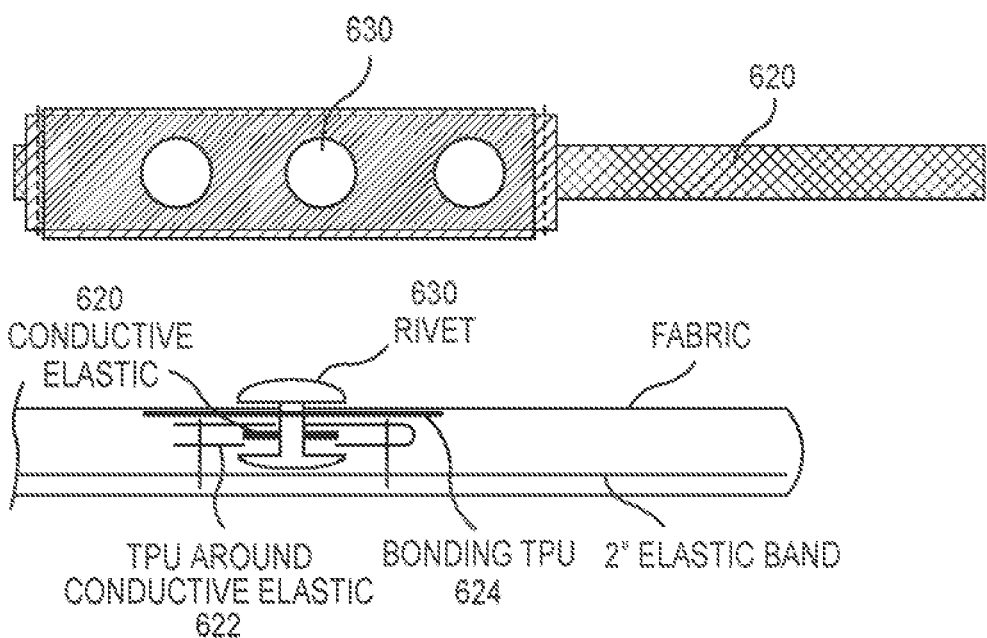
FIG. 6B shows further plan and cross-section views of an example assembled electrode assembly, including a bonding layer, according to an embodiment.

FIG. 6A shows plan and cross-section views of an example assembled electrode assembly, according to an embodiment. As shown, a conductive pathway 520 is partially encapsulated by a substantially rectangular heat adhesive TPU/barrier layer 522, and each of three electrodes 530 (e.g., rivets) of a linear electrode array is attached to the TPU-encapsulated conductive pathway (e.g., as described in FIGS. 4A-4D). All four sides (both long edges and both short edges) of the TPU layer are secured to a 2" elastic band via linear stitching. As shown in cross-section, a first end (e.g., "head") of the rivet 530 is disposed on a first surface of a fabric (e.g., a garment or portion thereof) and a second end of the rivet (e.g., a "tail") is disposed adjacent to an elastic band. The shaft of the rivet passes through the first surface of the fabric, both layers of the folded TPU 522, and the conductive pathway 520 (e.g., conductive elastic). In the location of the rivet electrode 530, the layers (from top to bottom in FIG. 6A) are the rivet head, a first section/layer of fabric (e.g., of a fabric that is folded about the elastic band and/or the conductive pathway, and through which the rivet shaft passes), a first section of TPU (e.g., of a TPU that is folded about the conductive pathway, and through which the rivet shaft passes), the conductive pathway 520 (through which the rivet shaft passes), a second section of TPU (through which the rivet shaft passes), the rivet tail, the elastic band, and a second section/layer of fabric (e.g., of a fabric that is folded about the elastic band and/or the conductive pathway). FIG. 6B shows plan and cross-section views of a further example assembled electrode assembly that includes the layers shown in FIG. 6A, but that only includes stitching along the short sides of the encapsulating TPU, and that further includes a bonding layer 624 (e.g., a further TPU) disposed between the first section of the TPU that encapsulates the conductive pathway and the first section/layer of fabric, according to an embodiment. By bonding a portion of the assembly directly to the fabric, the long edges of the encapsulating TPU are simultaneously bonded to the elastic band beneath the rivets.

FIGS. 7A-7C show an assembly/folding process, according to an embodiment. Specifically, FIG. 7A shows an elongate member 750 comprising a conductive member 752 coupled to three elastic members 753, the conductive member 752 having a curved/sawtooth pattern, the elongate member 750 having two sections of TPU 754 secured thereto and spaced apart. A dashed cut line is shown between the two sections of TPU. In FIG. 7B, two of the three elastic members have been cut along the cut line, and the elongate member is folded back on itself (at bend "B"), in-plane, such that the conductive member forms a continuous, substantially U-shaped path, and a first section of the elongate member is disposed substantially parallel to (and, in some embodiments, in a mirrored configuration) a second section of the elongate member. In other words the elastic members of the first section of the elongate member are parallel to the elastic members of the second section of the elongate member. The two sections of TPU are partially overlapping. In FIG. 7C, a further, larger section of TPU 756 is disposed atop a portion of the parallel elongate member sections, as well as atop the overlapping TPU sections, and is secured to a chest-band elastic, fabric, or other substrate via two longitudinal linear lengths of stitching (though other methods of attachment, such as adhesive and/or other patterns of stitching, are also contemplated). In some embodiments, the elongate member (e.g., a breathing sensor, a RIP sensor, an IP sensor, etc.) is configured to change from a first configuration to a second configuration (e.g., such that the conductive member changes from a first pattern to a second pattern) as the elongate member stretches. The change from the first configuration to the second configuration can result in a change of inductance of the conductive member.

Figure 8A:
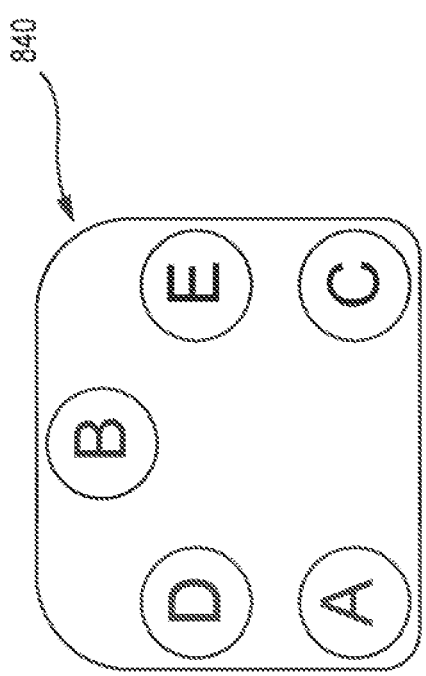
FIG. 8A shows an arrangement of electrical connectors, according to an embodiment.

FIG. 8A shows an arrangement of electrical connectors 840 (i.e., collectively a "biosensing garment connector region"), according to an embodiment. In some embodiments, conductive pathways described herein are connected to connectors A, B, and C at a connector area on the left side of the bra (from the wearer's perspective) via stainless steel snaps (e.g., comprising an S-spring socket and a hidden cap, or "snap cap"). The caps can comprise stainless steel, brass, or any other suitable (i.e., biocompatible) material. The connectors can be disposed on a connector base comprising a plurality of layers of heat adhesive TPU films and/or a flexible yet non-stretchable PET film, such that desired levels of support, reinforcement and insulation are achieved. In between the socket and the cap of each of the 5 snaps, a section (e.g., a round section) of conductive tape can be inserted/disposed to ensure a proper electrical connection between the hidden cap and the conductive pathway (e.g., conductive elastic, trace, wire, etc.) that is attached to it. For example, the conductive tape ring can be inserted in between the metal plate of the hidden cap and the conductive pathway prior to pressing the snap.

Connectors D and E can be connected to an elongate member (e.g., a RIP/breathing sensor) that extends along or is looped around the front side of the bra chest band. The elongate member can be a stretchable tape that is knitted with a conductive wire or filament that is disposed in a sinusoidal shape. The elongate member can be partially attached to a chest-band elastic, e.g., with TPU pieces/strips that are used to bond the elongate member to the chest-band elastic. The TPU pieces/strips can also be further stitched to secure the connection to the chest-band elastic. The same snaps as described above (stainless steel S-spring sockets and hidden caps) can be used to connect the elongate member to connectors D and E. In between the socket and the cap of snaps D and E, a layer (e.g., a ring) of a thin PET film can be inserted/disposed, for example to secure the elongate member and/or the conductive member of the elongate member, tightly against the snap bottom plate when connected (e.g., during assembly). Alternatively or in addition, to further secure the electrical connection, a ring of conductive adhesive tape can be inserted between the socket and cap of the snaps (e.g., such that the conductive member is sandwiched between the snap cap and the ring conductive adhesive tape, and ring of conductive adhesive tape is attached to the lower/inside surface of the PET ring). In such a configuration, the components are disposed in the following order: snap cap, conductive member, conductive adhesive tape, PET film ring.

Figure 8B:
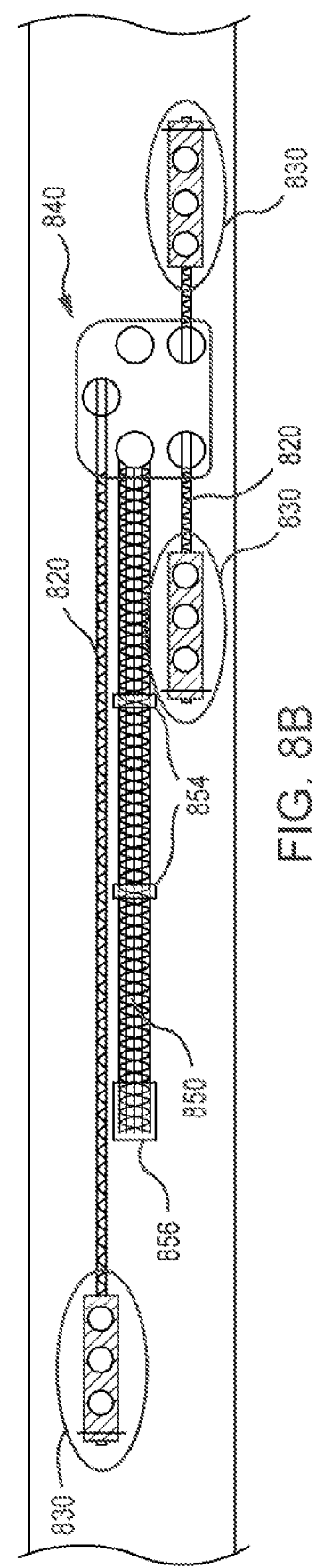
FIG. 8B shows an assembly including conductive pathways, electrical connectors, electrode arrays, and an elongate member, according to an embodiment.

A completed chest-band elastic, e.g., including integrated sensor(s) (elongate member 850), conductive pathways 850, electrode arrays 830 and/or connectors, as shown in FIG. 8B, can be secured (e.g., stitched or otherwise attached) to the biosensing garment itself, or the chest-band elastic may be integral with the biosensing garment.

In some embodiments, the length of the elongate member in its folded state is about 30 cm (e.g., 30.5 cm), as measured from the connector D. The entire length of the elongate member is therefore approximately twice that length (i.e., about 60 cm, or 61 cm). In some embodiments, the length of the elongate member in its folded state traverses about half a circumference of a wearer, such that the overall length of the elongate member prior to folding is approximately the full circumference of the wearer (e.g., the entire chest circumference). As such, embodiments described herein can achieve substantially the same resistance value(s) and sensor parameters as could be achieved in a sensor that traverses the entire circumference of the wearer (e.g., his chest), using the same hardware and with substantially the same levels of reliability and signal detection.

Figure 10:
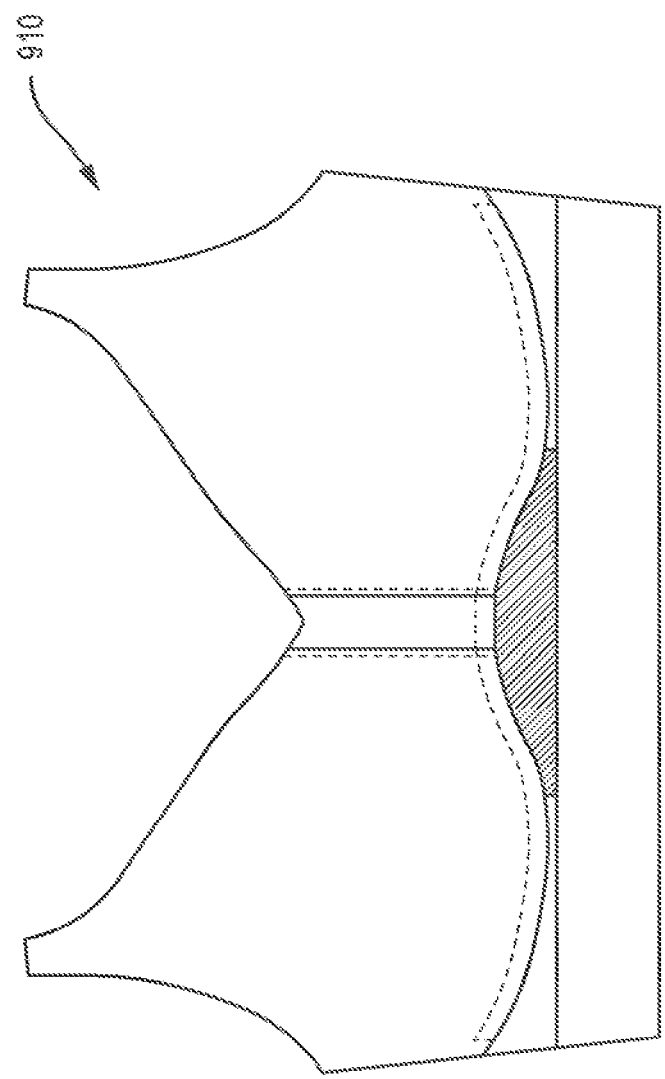
FIG. 10 shows a final outer view of the biosensing sports bra of FIGS. 9A-9B, including the chest-band elastic.

FIG. 9A shows an inner mesh lining and outlines of molded cups of a biosensing garment 910, according to an embodiment. The front lining of the biosensing sports bra 910 can comprise two layers. An 'inner' lining is inserted in between the "body" and the 'outer' lining. The inner lining is an open mesh ("powermesh") to which the padded cups can be stitched onto. The inner lining also adds support and stability to the bra. The outer lining is the skin-facing layer comprising a closed mesh and a mesh vent at the center front. Since the inner lining is an open mesh structure, is allows moisture vapor evaporation through the fabrics. The outer lining also has a mesh structure, but one that is tighter/denser than the inner lining (the pores are less noticeable but become more visible when the fabric is stretched), but that still allows higher rate of moisture evaporation than a solid knit. A ribbon-type trimming is stitched to the top part of the front lining, e.g., along the seam that joins the top part and the bottom part. Such a configuration increases the stability at the underbust by reducing the stretchability, acting as an "underwire," but without adding the bulkiness of a plastic or metal underwire, which can cause discomfort or pain if the wire is not well fitted to the chest. The ribbon can be stitched so that it terminates prior to reaching the side seam, so that it does not add bulkiness to the seam (where it could otherwise cause pressure or pain when wearing the bra). FIG. 9B shows the inner mesh lining of FIG. 9A with an outer lining fabric sewn onto it. FIG. 10 shows a final outer view of the biosensing sports bra 910 of FIGS. 9A-9B, including the chest-band elastic.

Figure 11:
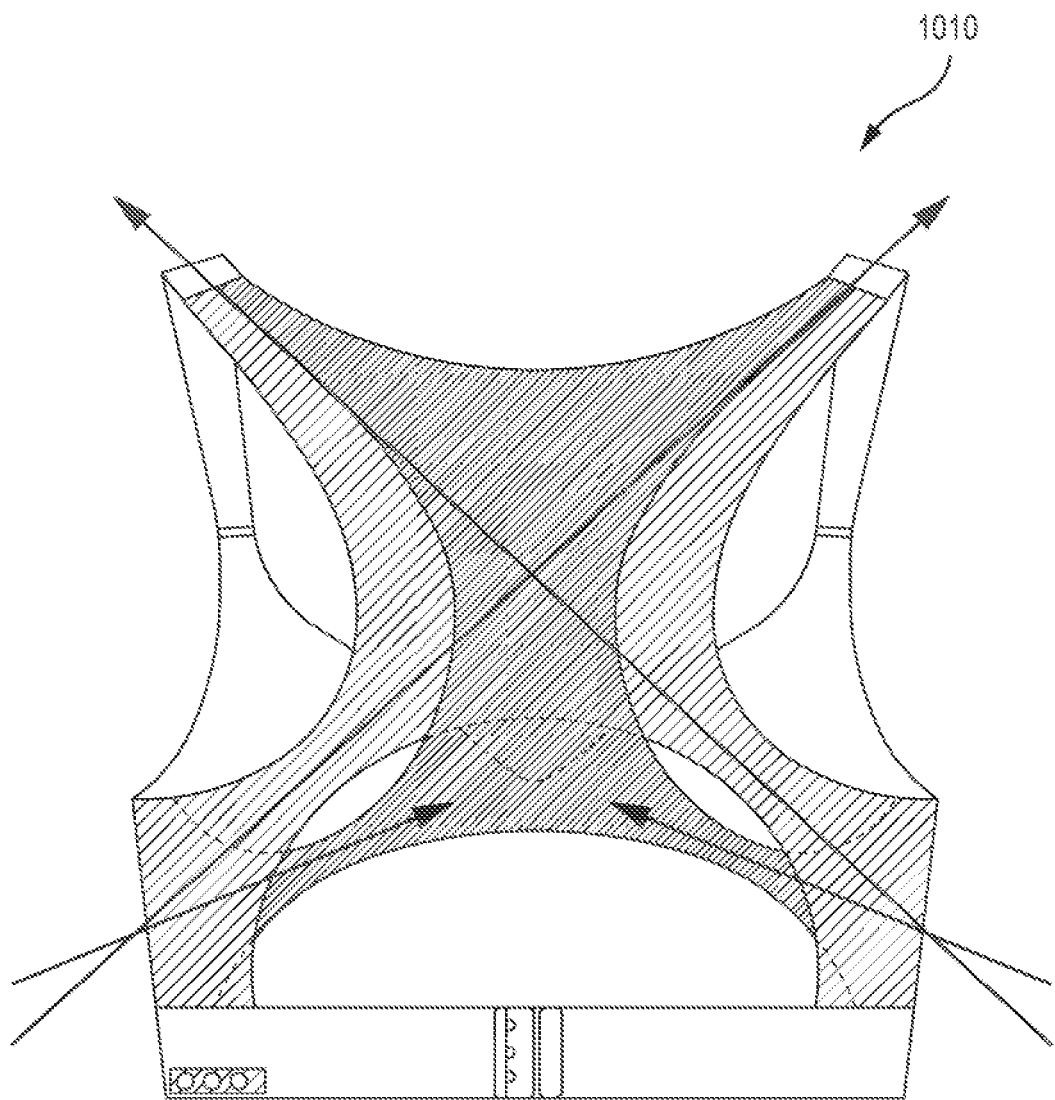
FIG. 11 shows a back view of a biosensing garment having a double racerback configuration, and showing support axes, according to an embodiment.

FIG. 11 shows a back view of a biosensing garment 1010 having a double racerback configuration, and showing support axes, according to an embodiment. The back of the biosensing sports bra 1010 is constructed of a two-layer racerback. The inner layer, i.e. the skin-facing layer, having a racerback shape, is made with a body fabric (e.g., the "self fabric," or the same fabric that is used for the outer fabric of the biosensing garment). The outer layer (also having a racerback shape) is constructed of a mesh fabric. The outer mesh layer is disposed beneath the body fabric at both sides and is connected to the side seams. The two layers are connected at the side seams as well as at the neckline and shoulders. This allows the two layers to act 'independently' to provide dynamic support during movement, and also to accommodate different body shapes and sizes. The overlapping of the two layers lends support and stability to the biosensing sports bra at the sides. Because the two overlapping racerback layers have different shapes, they support the bust by pulling from two different directions, and act as a "support axis" or "support vector," thereby distributing the weight of the bust to a larger area and supporting the bust more dynamically. Some or all of the garment edges can be finished with a binding that is either a soft elastic binding or a binding made from the "body" fabric itself.

Conductive Pathways (Conductive Bands)

As described herein conductive pathway(s) 120 are conductive elastic bands, for example, including a plurality of elastic filaments disposed substantially parallel to one another and mechanically coupled to one another by one or more conductive and/or non-conductive filaments that are knitted or woven about the elastic filaments. In other embodiments, either additionally or alternatively, the conductive pathway(s) 120 include one or more wires, conductive traces, metallizations, printed conductors, conductive laminates, and/or the likes. Examples of conductive pathways include one or more conductive bands described in detail below.

Embodiments described herein relate generally to wearable electronic applications that include one or more conductive bands. In some embodiments, a conductive band comprises one or more electrically conductive filaments (or fibers, threads, yarn, wires, etc.) and a plurality of elastic members that are mechanically joined together by the electrically conductive filament. In some embodiments, the elastic members are discrete from one another. Said another way, the elastic members can be distinct from, or not coupled to, one another until such that the conductive filament is added, thereby forming the conductive band. As such, the conductive filament may be said to serve as both an electrical conductor as well as a structural element that holds the conductive band together. In some embodiments, the elastic members are substantially parallel with one another. The conductive band has a first major longitudinal surface and a second major longitudinal surface. In some embodiments, the second major longitudinal surface is opposite the first major longitudinal surface. In some embodiments, the electrically conductive filament that is coupled to the elastic members to form the conductive band is disposed such that the electrically conductive filament imparts conductivity to both the first major longitudinal surface and the second major longitudinal surface.

In some embodiments described herein, a conductive elastic band, or "conductive band," suitable for use in wearable electronic applications, is configured to act as a conductor (to transfer signals) and/or as a strain sensor (to detect e.g. movement or respiration). The conductive band can also be used as an electrode to detect signals such as electrocardiogram (ECG) signals and electromyography (EMG) signals from the skin of a wearer. In some embodiments, the conductive band is an elastic band made up at least in part of one or more elastic members and one or more filaments (or fibers, threads, yarns, wires, etc.), where all or part of the one or more filaments is electrically conductive (e.g., X-Static fiber and/or any suitable conductive material, such as a stainless steel plated material, other types of metal-clad materials, etc.). The conductive filaments can be braided, woven, knitted, and/or otherwise coupled to the elastic members to form a composite conductive band. For example, the conductive filaments can be woven about the elastic members such that the elastic members are mechanically secured within the woven pattern. In some embodiments, the conductive band includes one or more non-conductive filaments (or fibers, threads, yarns, wires, etc.). The band construction (whether conductive or non-conductive) can vary based on the required properties for a given application. For example, the number of plies, yarn/thread count, twist type (e.g., S twist, Z twist or non-twisted), number of twists/inch, etc. of the filaments (either conductive filaments or a combination of conductive and non-conductive filaments) can be selected so as to achieve a desired performance parameter, such as conductivity, elasticity, force required to stretch to a certain degree, thickness, and/or the like. Either all or some of the filaments are electrically conductive, for example, to achieve a required level of conductivity. In some embodiments, all of the filaments are conductive (e.g., to maximize conductivity). In some embodiments, a plurality of filaments are used to form the composite conductive band, and only "some" of the filaments (i.e., a subset of the filaments) are conductive, such that the conductive band includes both conductive and non-conductive filaments. In still other embodiments, "portions" of all or some of the filaments are conductive, or are modified so as to be conductive (i.e., one or more of the filaments may only be conductive along a portion of its length). In some embodiments, the filaments can be insulated and only portions of the insulation can be removed to expose the conductive portion of the filaments. In other words, the filaments can be selectively insulated to provide insulation on some portions and provide a conductive pathway on some portions. By virtue of all or part of the filaments being electrically conductive, a band is created that is conductive on both of its surfaces (e.g., on both of its major longitudinal surfaces) as well as conductive through the cross-sectional thickness of the band (i.e., exhibiting volume resistivity). The elastic members can be elastane fibers comprising any elastomeric material, e.g. spandex or rubber, and can be of any suitable fiber size (also referred to as "denier"). The denier of the elastane fiber can be selected depending upon the embodiment or application, for example, to achieve a desired thickness, elasticity, and/or force of the conductive band. In some embodiments, the elastomeric material can be wrapped with conductive fibers.

The conductive band can be manufactured using knitting, weaving, braiding, or any other suitable technique, depending on the desired physical and electrical properties. The conductive band can be of any desired width, such as ½" ¾" ½" ¾", 1", etc. In some embodiments, the conductive band has a substantially flat shape. In some embodiments, the conductive band can have a substantially round or oval cross-section.

In some embodiments, a conductive band can include a support band (which may also be referred to as an "elastic band") with a plurality of elastic members and a plurality of non-conductive filaments (or fibers, threads, yarns, wires, etc.). For example, the non-conductive filaments can be knitted about the elastic members to form a support band such that the elastic members are enmeshed within the support band and disposed along a longitudinal axis of the support band, for example in substantially parallel relation to one another. One or more conductive filaments can be introduced to (e.g., knitted with, threaded within, woven with, inserted into, affixed to, wrapped around, etc., for example in a periodic pattern such as a sinusoid) only one surface of the support band, or to both surfaces of the support band, for example so as to create conductivity and/or surface resistivity across only one, or across both surfaces of the overall band. In some embodiments, the one or more conductive filaments are fed in a sinusoidal (or other) shape while knitting the support band with one or more non-conductive filaments.

The conductive band can be integrated to and/or paired with a variety of electrodes in biosensing garments. For example, the conductive band can be paired with ECG or EMG electrodes by connecting them via a method such as stitching, riveting, snapping, crimping, gluing, bonding, welding, etc. Due to the flexible and elastic nature of the conductor within the conductive band (which serves, for example, as an electrical trace), flexible placement of the electrodes on any bio-sensing garment is achieved, such that the electrodes can be placed anywhere on the body or any type of garment. The conductive band can be unattached to a textile (e.g., flow or drape freely) between connecting points thereof, or can be attached (e.g., partially or along its full length) to the textile using a variety of methods such as stitching, laminating, bonding, ultrasonic welding, channeling though a tunnel or series of loops, slits, and/or the like, as discussed further below with reference to the figures.

Figure 12:
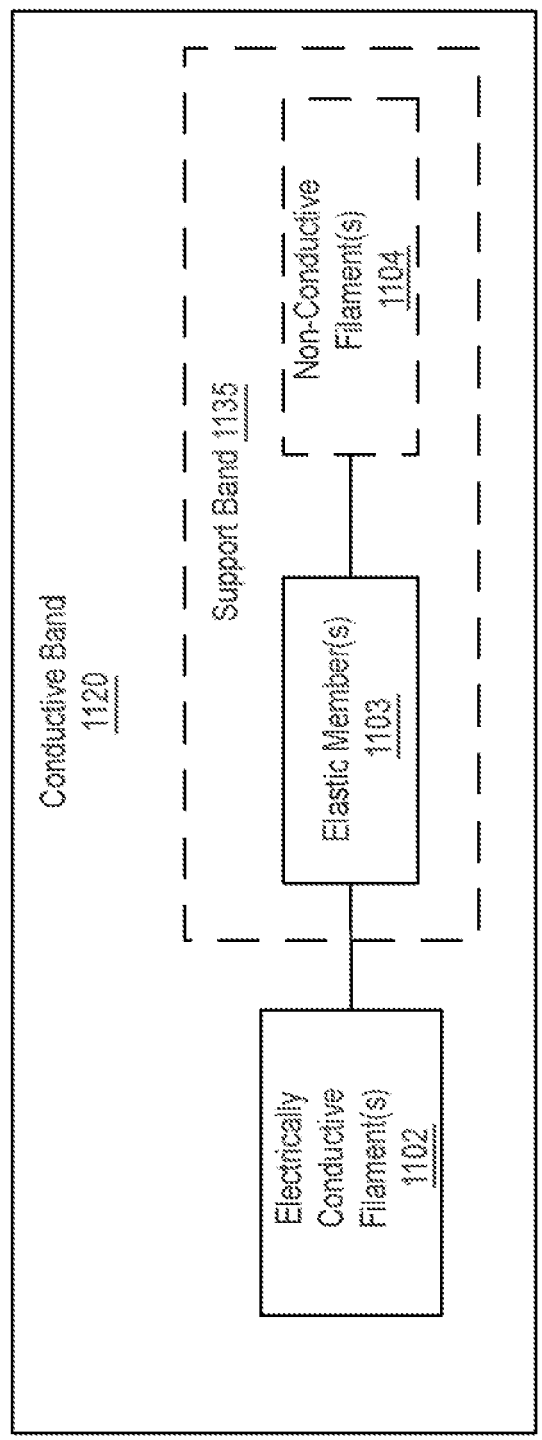
FIG. 12 is a schematic block diagram of a conductive band, according to an embodiment.

Referring now to FIG. 12, a schematic block diagram of a conductive band, according to some embodiments, is shown. A conductive band 1120 (e.g., conductive pathways 120 in FIG. 1) includes one or more elastic members 1103 coupled to one or more electrically conductive filaments 1102 and, optionally, one or more non-conductive filaments 1104. The conductive band 1120 may have a band-like or ribbon-like shape, such that it is elongate (i.e., longer than it is wide) and has two major faces (e.g., a front and back or top and bottom) that extend along its longitudinal axis. The electrically conductive filaments 1102 (and, optionally, the non-conductive filaments 1104) are mechanically coupled to the elastic members 1103, for example by weaving, knitting, wrapping, crocheting or knotting. The conductive band 1120, by virtue of the elastic members 1103 and/or the shape/pattern of the electrically conductive filaments 1102, is stretchable along its longitudinal axis. In some embodiments, the conductive band 1120 is substantially inelastic (i.e., not stretchable) along its short or transverse axis. The elastic members 1103 can be made of any stretchable material, such as an elastane fiber or strand comprising any elastomeric material, e.g. spandex or rubber, and can be of any suitable denier. The size (e.g., denier and/or length) of the elastane fiber can be selected according to its suitability for a given application, for example, to achieve a desired thickness, elasticity, and/or force of the conductive band 1120. The electrically conductive filaments 1102 can include solid metal (e.g., metal wire) or a metal-coated nonmetal, such as X-Static fiber or Circuitex, a flexible polymer material coated with metal such as silver, Lurex, or any other conductive material, such as stainless steel plated filament (e.g., yarn), other types of metal-clad filament (e.g., yarn), etc. In some embodiments, the conductive filaments 1102 are non-stretchable or substantially non-stretchable. In other embodiments, the conductive filaments 1102 are stretchable. In some embodiments, the conductive filaments 1102 are antimicrobial. In some embodiments the elastic members 1103 and the non-conductive filaments 1104, collectively, form an intermediate support band 1135 that may be non-conductive, and into which the electrically conductive filaments is woven or otherwise routed, or to which the electrically conductive filaments is affixed. The non-conductive filaments 1104 can include a thread, yarn, or other type of filament made of a natural or man-made material such as is used in the manufacture of textiles, for example cotton, wool, flax, polyester, aramid, acrylic, nylon, spandex, olefin fiber, ingeo, and/or the like.

Figure 13:
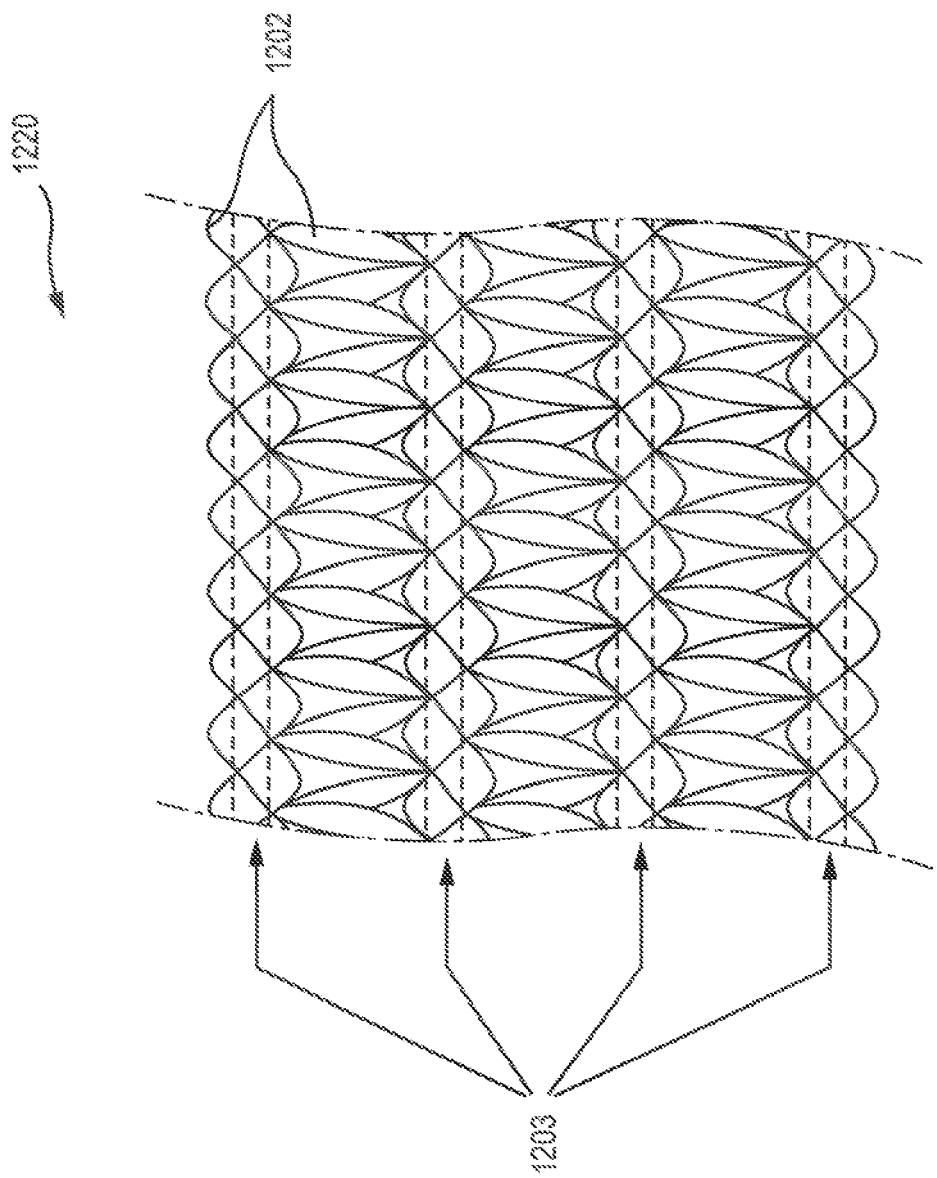
FIG. 13 shows a plan view of a conductive band, according to an embodiment.

FIG. 13 shows a plan view of a conductive band, according to an embodiment. As shown, four elastic members 1203 are disposed parallel to one another along the longitudinal axis of the conductive band 1220. One or more electrically conductive filaments 1202 (e.g., a single-ply filament or a two-ply conductive filament) are knitted or woven about the four elastic members 1203, thereby mechanically coupling the four elastic members 1203 together and creating a weave pattern that repeats along the length of the conductive band 1220. In some embodiments, four first electrically conductive filaments 1202 are knitted, woven, or stitched around/about corresponding ones of the four elastic members 1203 (i.e., using four separate conductive filaments), and one or more further conductive filaments 1202 is subsequently interlaced with the four first electrically conductive filaments to produce the conductive band 1220.

Figure 14:
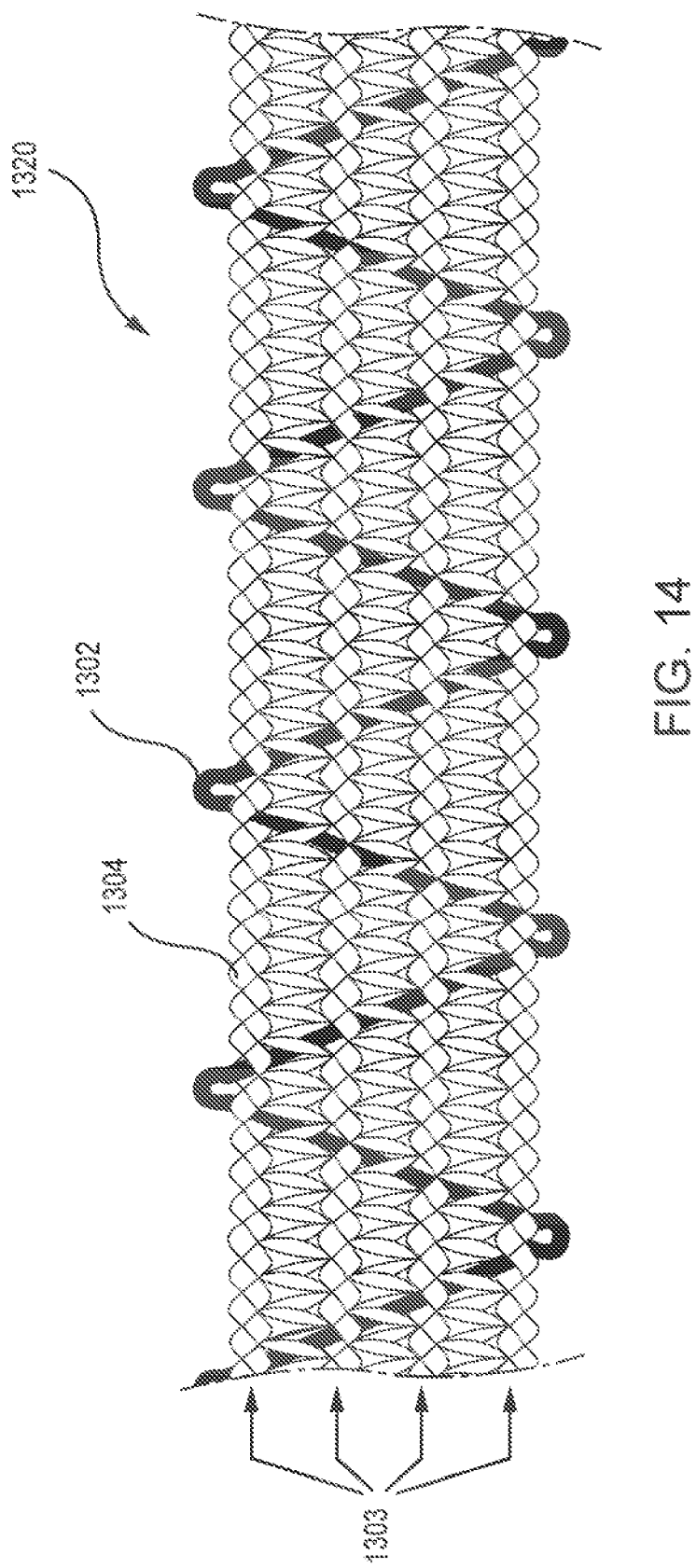
FIG. 14 shows a plan view of a conductive band, according to an embodiment.

FIG. 14 shows a plan view of a conductive band, according to another embodiment. As shown, a bundle of electrically conductive filaments 1302 (collectively a "conductive yarn" or "conductor") passes through a support band comprising a plurality of elastic members 1303 and one or more non-conductive filaments 1304 woven about the elastic members 1303. The conductive filaments 1302 are fed through the support member in a periodic pattern, which is shown in FIG. 14 to be a substantially zigzag (i.e., a triangle wave or sawtooth), but in some embodiments can take on other shapes, such as sinusoidal, aperiodic, etc., and can have either a constant or a varying period ("periodicity") or frequency. The support band and the one or more conductive filaments 1302, collectively, form a conductive band 1320. FIG. 15 is a detail view of the conductive band 1320 of FIG. 14. In some embodiments, the conductive yarn 1302 is fed simultaneously with the knitting or weaving of the support band, so as to interlace or interweave the conductive yarn 1302 with the non-conductive filaments 1304. In some embodiments, the conductive band 1320 is not substantially conductive on either of the major longitudinal surfaces of the conductive band 1320, and is therefore suitable, for example, for data transfer purposes and/or as a conductive trace or pathway.

In some embodiments, the conductive band configuration shown in FIG. 14 can be obtained by inserting/adding conductive filaments to an already-fabricated support band to form a conductive band. In other embodiments, a conductive band is formed by replacing one of the non-conductive filaments of the support band with one or more electrically conductive filaments. In still other embodiments, a conductive band is formed using the non-conductive filaments and the one or more electrically conductive filaments simultaneously. For example, rather than starting with a non-conductive support band, a conductive band can be formed by knitting (or weaving, wrapping, knotting, etc.) one or more non-conductive filaments and one or more conductive filaments about a plurality of elastic members. In still further embodiments, a conductive band is formed by knitting (or weaving, wrapping, knotting, etc.) one or more conductive filaments (e.g., two conductive filaments, or "two-ply" conductive filament) about a plurality of elastic members, and does not include any non-conductive filaments.

To incorporate a conductive band as described herein into a textile (e.g., a garment or other wearable textile, or portion thereof), several approaches can be used. By way of example, FIG. 16A is a cross-sectional view of a conductive band 1420 that is laminated to a substrate 1406, according to an embodiment. As shown in FIG. 16A, a conductive band 1420 is disposed on a substrate 1406 (such as a textile) surface, and a laminating layer 1405 is disposed on top of the conductive band 1420. The laminating layer 1405 can include, for example, a thermoplastic material or any other heat-sealable or self-sealing material layer. In some embodiments the lamination acts as an electrical insulator as well as a means of attachment. Depending upon the application, the lamination may be placed along the entire length of the conductive band, or may be selectively placed at desired locations, for example to ensure that portions of the conductive band remain exposed to a user and/or to the external environment, e.g., so that it can readily be connected to a measurement or communications device, and/or so that it can serve as an electrode for collecting biological and/or other signals (e.g., from sensors).

FIG. 16B is a cross-sectional view of a conductive band 1420 that is bonded to a substrate 1406 (e.g., a textile such as a fabric or a garment) surface, according to an embodiment. A laminating or other bonding material (e.g., thermoplastic, adhesive, etc.) 1472 is disposed beneath the conductive band 1420 in FIG. 16B so as to mechanically attach it to the substrate 1406 surface. Such a configuration leaves one full major longitudinal surface, and potentially the two minor longitudinal edges, of the conductive band 1420 exposed, and thus available for use as an electrode and/or for connection to a measurement or communications device.

FIG. 16C is a cross-sectional view of a conductive band 1420 that is stitched (e.g., using filament such as thread or yarn 1474, which may be conductive or non-conductive) to a substrate 1406, according to an embodiment. In other embodiments, the conductive band 1420 is welded to the substrate 1406.

Figure 17A:
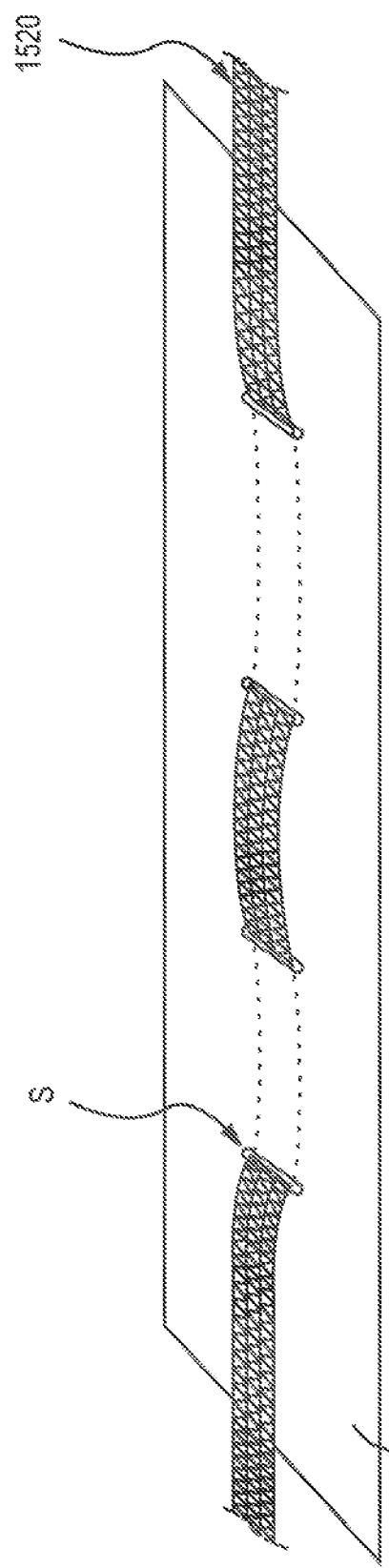
FIG. 17A is a perspective view of a conductive band that has been routed through a series of slits in a substrate, according to an embodiment.
Figure 17B:
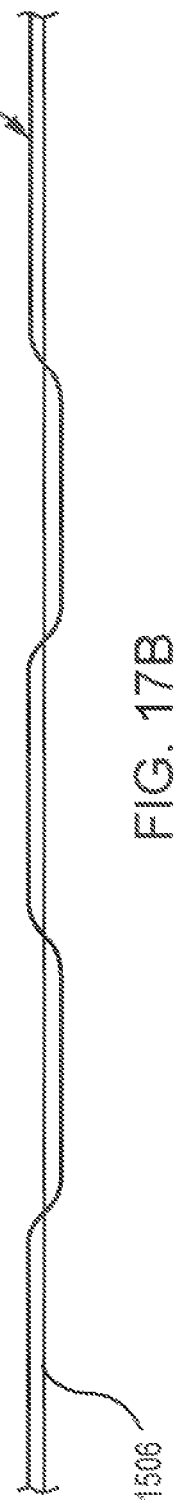
FIG. 17B is a side view of the conductive band and substrate of FIG. 17A.

FIG. 17A is a perspective view of a conductive band 1520 that has been routed through a series of slits "S" in a substrate 1506 (such as a textile), according to an embodiment. FIG. 17B is a side view of the conductive band 1520 and substrate 1506 of FIG. 17A.

Figure 18A:
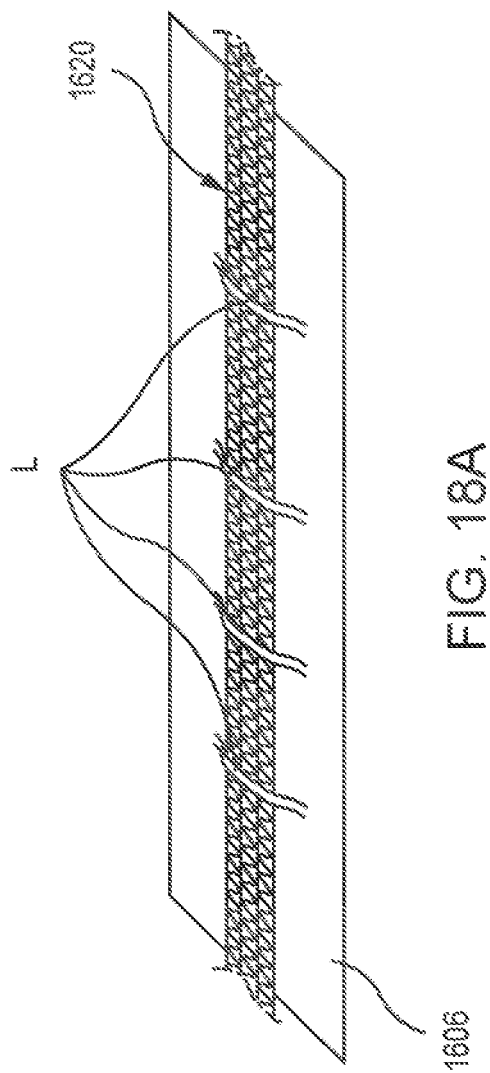
FIG. 18A is a perspective view of a conductive band that has been secured to a substrate with a series of loops, according to an embodiment.
Figure 18B:
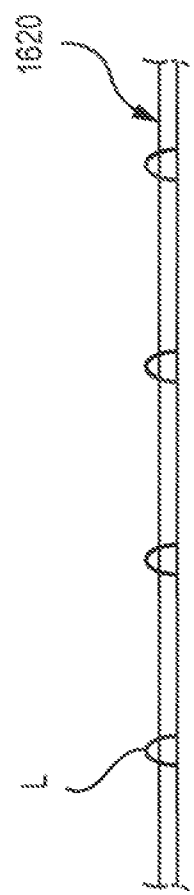
FIG. 18B is a side view of the conductive band and loops "L" of FIG. 18A.

FIG. 18A is a perspective view of a conductive band 1620 that has been secured to a substrate 1606 with a series of loops "L," according to an embodiment. FIG. 18B is a side view of the conductive band 1620 and loops "L" of FIG. 18A.

FIG. 19A is a perspective view of a conductive band 1720 disposed within a tunnel structure "T" on a substrate, according to an embodiment. FIG. 19B is an end view of the conductive band 1720 and tunnel "T" of FIG. 19A.

FIG. 20 is a cross-sectional view of a conductive band 1820 disposed within a textile/garment 1806 or portion thereof, with a segment 1820B of the conductive band exposed at a surface of the garment 1806 and a segment 1820A of the conductive band disposed beneath a surface of the garment 1806, according to an embodiment. By selectively passing the conductive band 1820 up through the textile surface (e.g., through slits, as shown in FIG. 20), or, alternatively, by selectively including openings in the textile on at least one side of the conductive band 1820, the conductive band 1820 can come in contact with the skin of a wearer, such that the conductive band 1820 can act simultaneously as a conductor trace and as an electrode (e.g. in ECG and/or EMG applications, etc.).

Figure 22:
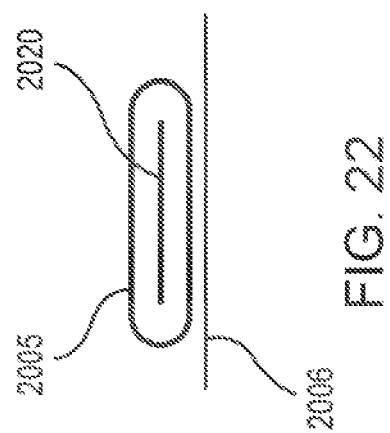
FIG. 22 is a cross-sectional view of a conductive band disposed within a fabric tube, according to an embodiment.

When used as a conductive trace and/or as a strain sensor, the conductive band can be either insulated or not, partially or completely, on one or both sides, depending upon the application. Insulation, e.g. thermoplastic adhesive film, can be applied to encapsulate desired areas of the conductive band, and/or the conductive band can be disposed within fabric tubing. FIGS. 21A-21C are cross-sectional views of a conductive band that is laminated to a substrate, according to some embodiments. Specifically, FIG. 21A shows a conductive band 1920 that is laminated (via lamination 1905) to a substrate 1906 on one side of the conductive band 1920. FIG. 21B shows a conductive band 1920 that is laminated on both sides, using two separate laminating elements 1972 (e.g., film segments). FIG. 21C shows a conductive band 1920 that is laminated on both sides, using a single folded laminating element 1974 (e.g., film segment). FIG. 22 is a cross-sectional view of a conductive band 2020 disposed within a fabric tube 2005, according to an embodiment. With regard to FIGS. 21B, 21C and 22, once an insulation (e.g., lamination or fabric) has been applied to a conductive band, the insulated conductive band can then be attached to the textile/garment (e.g., 1906,2006) using any of the methods described herein.

Electrode Arrays

Examples of electrodes 130 include a plurality of electrodes including an array of at least two metallic rivets or snaps as described in further detail below. As described herein, a plurality of electrode(s) 130 may be mechanically coupled to the biosensing garment 110, electrically coupled to the conductive pathway 120, and configured to contact skin of a wearer during use.

Embodiments described herein, relating generally to wearable electronic applications that include a metal-based electrode system or configuration, overcome the disadvantages commonly associated with existing electrodes. In some embodiments, a biosensing apparatus comprises a garment with a conductive pathway disposed therein or thereon, and a plurality of electrodes including an array of at least two metallic rivets or snap caps. The plurality of electrodes is mechanically coupled to the garment, electrically coupled to the conductive pathway, and configured to contact skin of a wearer during use. The benefits of an electrode configuration that comprises more than one article, such as a metal rivet, are multifold: increased design flexibility, increased measurement surface area for signal detection, increased degree of redundancy, increased resistance to movement artifacts, increased flexibility, and adaptability to variation in body shapes. Electrodes described herein can be used in bio-sensing garments and accessories for a variety of applications, such as electrocardiography (ECG) and electromyography (EMG). Electrodes described herein can also be used as part of a breathing rate sensor circuit (e.g., for wire-based impedance pneumography (IP) or respiratory inductance plethysmography (RIP)), and/or to derive breathing rate from an ECG signal, such as from heart rate variability (HRV) or R peak amplitude (i.e., the maximum amplitude in the R wave deflection of an ECG). Rivet-type metal electrodes of the present disclosure can be integrated to any type of garment/textile or other bio-sensing assembly, and can be connected directly to any type of conductive pathway, such as a wire, knitted conductive trace, conductive elastic band, and/or the like.

As defined herein, an "electrode array" is one or more individual electrodes in any configuration, where the electrodes of the plurality of electrodes may or may not be evenly spaced or distributed. In some embodiments, the electrode array includes a two-dimensional arrangement of electrodes that can be symmetric or asymmetric. In some embodiments, the electrode array includes a one-dimensional arrangement of electrodes that can be a single row or column. In some embodiments, the electrode array is a three-dimensional arrangement of electrodes. Each electrode of the electrode array 130 is an article such as a snap cap, a socket, a stud, a post, (e.g. an S-spring, ring-spring, prong type), a rivet, a cover button, and/or the like. Electrodes of the electrode array can have a shape that is round, triangular, rectangular, or any other shape. The diameter of electrodes of the electrode array 130 can be, e.g. 3 mm, 5 mm, 9 mm, 12 mm, 15 mm, or any other size, for example to improve signal quality and/or comfort of the wearer. The electrode array 130 can include one or multiple articles, for example 2, 3, 4, 5, 6 or more, in a configuration as discussed in greater detail below. A single bio-sensing garment (e.g., 110 in FIG. 1) can include one or more electrode arrays (e.g., 130 in FIG. 1), each grouping including 2 or multiple electrodes, such as 3, 4, or more, in a cluster or configuration. In other embodiments, a single bio-sensing garment (e.g., 110 in FIG. 1) can consist of multiple electrode arrays (e.g., 130 in FIG. 1) (i.e., multiple clusters having the same or different configurations). The electrodes of the electrode array can comprise any suitable metal, such as brass, silver, gold, stainless steel, etc., or a combination thereof. Additionally or alternatively, the electrodes of the electrode array can comprise a topical coating of any suitable conductive material such as silver, gold, conductive polymer, etc., or a combination thereof. The electrode array can be located anywhere on the bio-sensing garment, for instance on the chest area, the back, arms, legs, shoulders or any other desired location on the body. In some embodiments, the biosensing garment (e.g., 110 in FIG. 1) includes multiple electrode arrays (e.g., 130 in FIG. 1), each including one or more clusters or groupings of articles (e.g., rivets, snaps, etc.), positioned/disposed in different locations on the biosensing garment.

Depending upon the embodiment or application, some or all of the electrodes of the electrode array are configured to contact skin of a wearer during use. In other words, the electrodes of the electrode array have a skin-contacting surface and a non-skin-contacting surface opposite the skin-contacting surface. In some embodiments, the electrodes of the electrode array include small diameter rivets, such that they can be placed discreetly and/or comfortably within garments such as underwear and bras, e.g., on bra straps or bra chest-bands. The electrodes of the electrode array can be attached to any suitable substrate (either within the biosensing garment itself, or prior to attachment to the biosensing garment), such as an elastic band, a fabric, a heat-activated thermoplastic adhesive film, a plastic sheet, etc., and be can be laminated, stitched, bonded, or otherwise attached to the biosensing garment. The electrodes of the electrode array can also be directly attached to the fabric of the biosensing garment, for example by pressing them through the fabric while simultaneously connecting them to the conductive pathway. In some instances, one or more electrodes of the electrode array can be insulated on a non-skin-contacting surface (or "reverse" side) with a layer of insulating material, such as heat activated thermoplastic adhesive film ("TPU"), a coating, a spray, or any other desired method, for example to insulate the electrodes from humidity, electrostatic interference, external electrical interference, and/or mechanical interference. The non-skin-contacting surface of a snap, rivet, or other artifact, for example, can, in addition or alternatively, be coated/treated with a non-conductive material, such as plastic, prior to attaching it to the garment.

Figure 23:
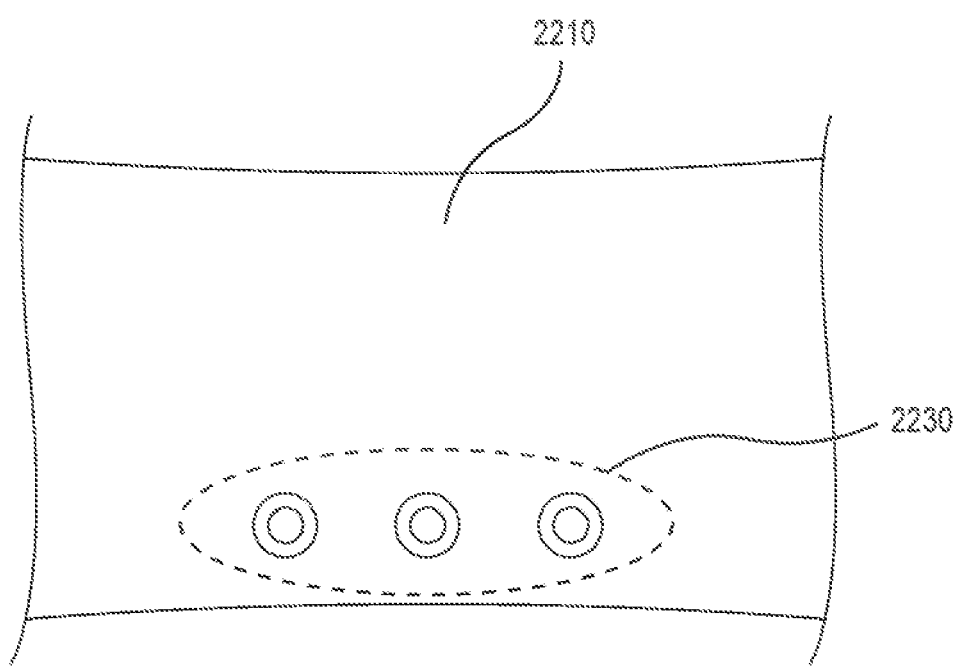
FIG. 23 shows a configuration of rivet electrodes, according to an embodiment.
Figure 25:
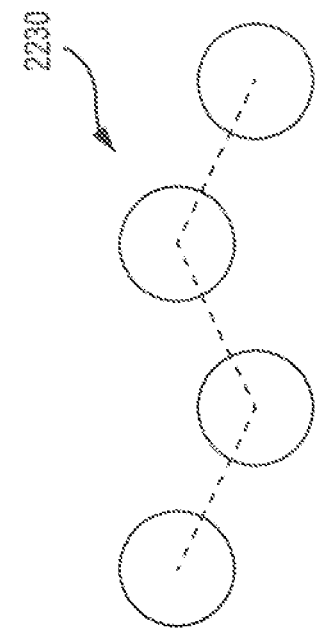
FIG. 25 shows a configuration of rivet electrodes, according to an embodiment.
Figure 27:
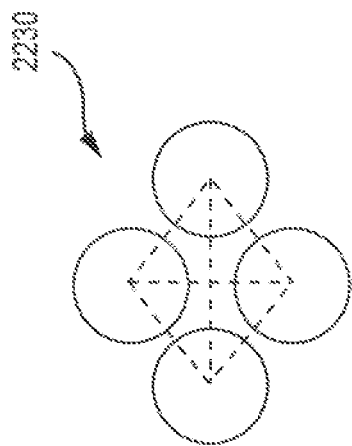
FIG. 27 shows a configuration of rivet electrodes, according to an embodiment.
Figure 24:
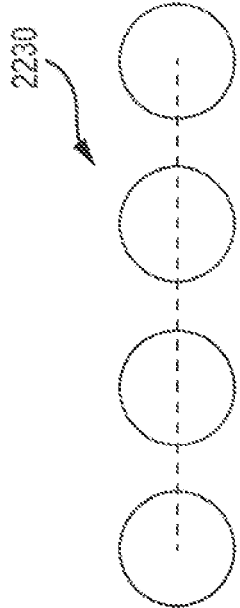
FIG. 24 shows a configuration of rivet electrodes, according to an embodiment.
Figure 26:
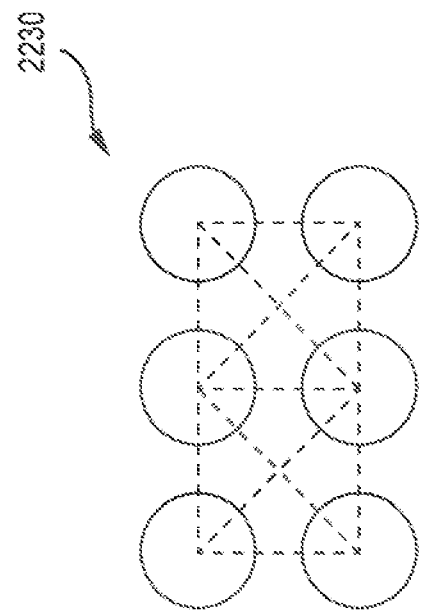
FIG. 26 shows a configuration of rivet electrodes, according to an embodiment.

When using multiple rivets, snaps, and/or caps in a single electrode array, they can be spaced apart from one another at any desired distance, for instance 5 mm, 10 mm, 15 mm, 30 mm, etc., and can be placed at any desired configuration. For example, FIG. 23 shows an electrode array 2230 including three rivet electrodes arranged on a biosensing garment 2210 (in this case, a textile band) with a spacing of about 1 cm, according to an embodiment. The rivets have been pressed through the fabric so that they are placed in contact with the skin of a wearer when the biosensing garment is worn. Although shown in FIG. 23 to comprise rivets, in some embodiments the electrode array 2230 can instead include snap caps, or a combination of snap caps and rivets, etc. FIG. 24 shows an electrode array 2230 including rivet electrodes in a substantially linear configuration, according to an embodiment. FIG. 25 shows an electrode array 2230 including rivet electrodes in a zig-zag (or "triangle wave," "sawtooth," or "meandering") configuration, according to an embodiment. FIG. 26 shows an electrode array 2230 including rivet electrodes comprising an orthogonal array (also "square packed"), according to an embodiment. FIG. 27 shows an electrode array 2230 including rivet electrodes in a diamond-shaped configuration, according to an embodiment. Other configurations contemplated by the present disclosure include hexagonal packing, circular, oval and curved configurations.

By using S-spring type snaps with a socket and cap (or other suitable snap type, depending on the transmitter being used in conjunction with the biosensing garment), the electrode can be directly connected to a transmitter (and/or other hardware) and act simultaneously as both a connector and an electrode. In other words, in such configurations, the cap faces the skin of the wearer and acts as the electrode, and the socket receives the transmitter connection. This can be applied to any type of transmitter that has snap studs as connectors, and the socket configuration and quantity can be selected so as to accommodate the required number of snaps (e.g., 2, 3, or more).

FIG. 28A shows a biosensing garment 2310 including an array of electrodes, "1," "2" and "3" (e.g., snaps, sockets, caps, and/or rivets), which are disposed on a lower, chest band portion of a biosensing brassiere 2310, and together with two connectors, "B1" and "B2," collectively forming a "biosensing garment connector" 2340 for example, electrical connectors 140 in FIG. 1 (or "wearable device connector" or "wearable device interface" or "wearable connector"), configured to interface with a measurement and/or communications device (such as a transmitter, a mobile device, a controller box, etc.). In some embodiments, the biosensing garment connector 2340 is configured to capture and/or monitor a biological signal, such as an ECG signal.

Electrode "3" is an optional "ground" electrode. Without wishing to be bound by theory, the ground electrode can serve, in some embodiments, one or more of the following functions: to prevent electrical interference (noise), to obtain a differential voltage by subtracting the voltages from other electrodes (e.g., electrodes "1" and "2," which may correspond to a positive (+), or "active," electrode and a negative (−), or "reference," electrode, respectively). The positive and negative electrodes may be referred to as "measuring" electrodes. In some embodiments, the ground electrode can be used to compare the signals at electrodes "1" and "2" and subtract components of those respective signals that are common to both of the electrodes "1" and "2" (e.g., the noise component of the signals).

Figure 28C:
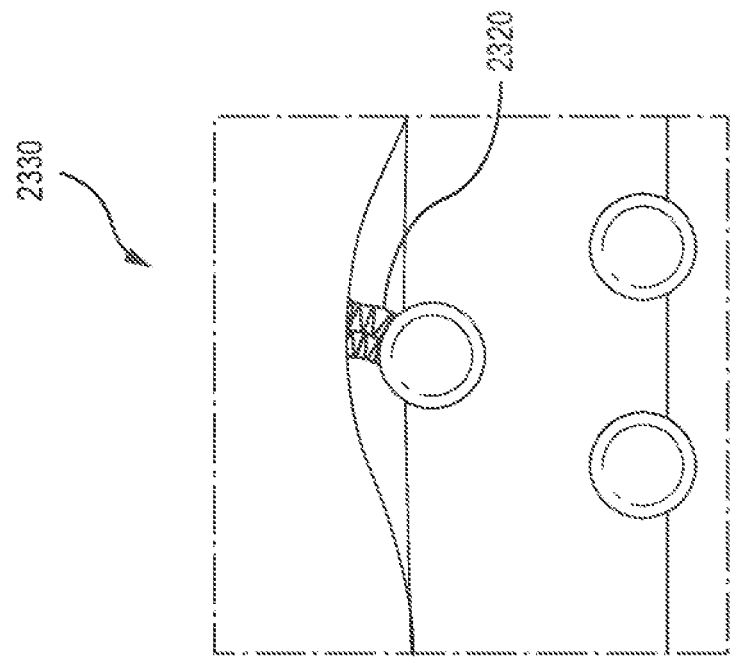
FIG. 28C shows an interior view of a portion of the biosensing garment of FIG. 28A.
Figure 28B:
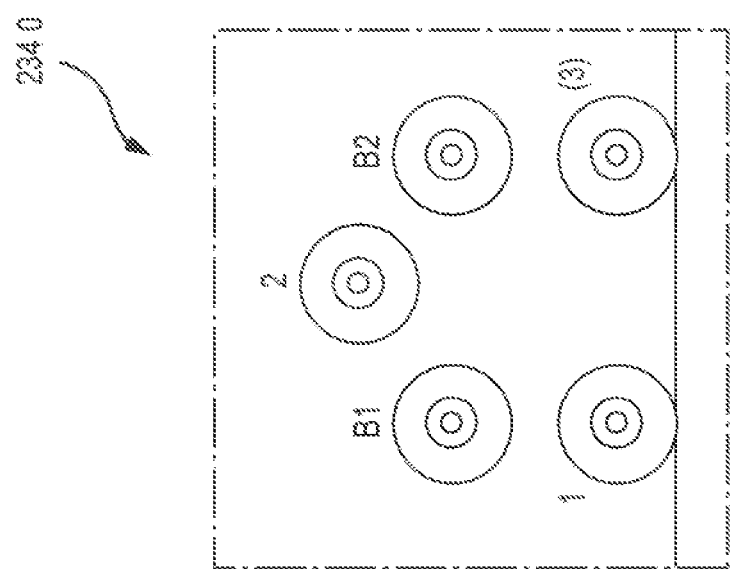
FIG. 28B shows an exterior view of a portion of the biosensing garment of FIG. 28A.

A further electrode "4A" is electrically connected to (via a conductive pathway, such as a conductive elastic, metal trace, wire, stretchable wire, conductive printing, etc.), but disposed remotely from (i.e., on a shoulder strap of the biosensing brassiere), electrode "2" of the biosensing garment connector area. Although the electrode "4A" (e.g., a snap, socket, cap, or rivet) is shown to be disposed on the front of the left shoulder strap of the biosensing brassiere (from the wearer's perspective), electrodes of the present disclosure can be placed, alternatively or in addition, at any other location on the biosensing garment (e.g., on the rear of the left shoulder strap (see location 4B in FIG. 28A), on the front or rear of the right shoulder strap, on the upper chest, etc.). Depending upon the embodiment, electrode "4" can function as a standalone replacement for electrode "2," or both electrodes "2" and "4" can be in contact with the skin at the same time. In some embodiments, electrode "4" is omitted. FIG. 28B shows an exterior view of a portion of the biosensing garment connector 2340 of FIG. 28A, including 5 S-spring type sockets (of a snap connector), labelled "1," "2," "(3)," "B1," and "B2," collectively forming the biosensing garment connector. FIG. 28C shows an interior view of a portion of the biosensing garment of FIG. 28A, showing an electrode array 2330 including three cap electrodes (each connected to a corresponding S-spring type socket of FIG. 28B, e.g., electrodes 1, 2 and 3) that are configured to contact skin of a wearer of the biosensing garment. A single electrode may be said to include both a cap and a socket (e.g., mechanically and electrically coupled to one another through the thickness of the fabric of a biosensing garment). An upwardly-extending conductive pathway 2320 (e.g., conductive pathways 120 in FIG. 1), in the form of a conductive band, is partially visible adjacent (and electrically connected to) the uppermost cap in FIG. 28C.

Figure 28D:
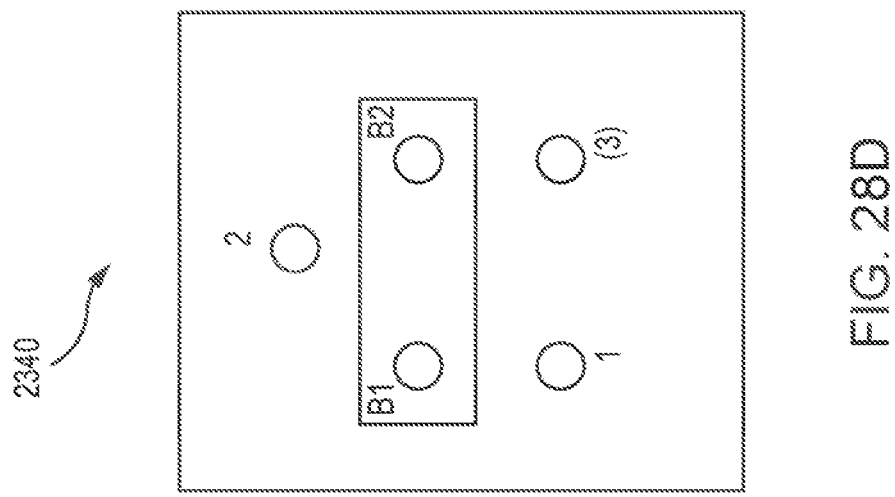
FIG. 28D is a diagram of the biosensing garment connector of FIG. 28A.
Figure 28E:
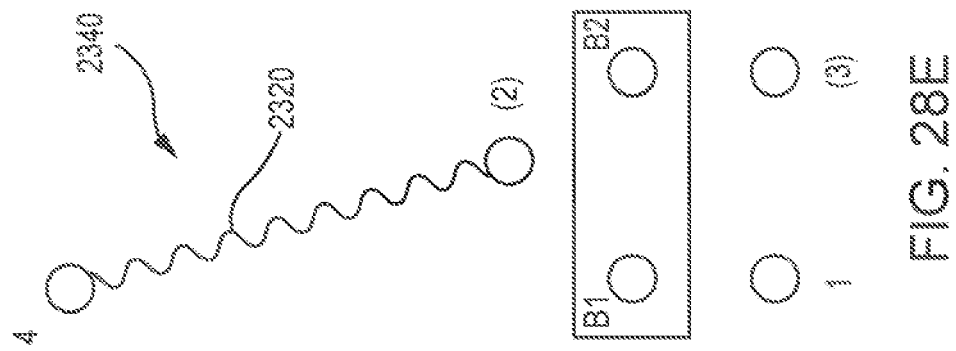
FIG. 28E is a diagram of the biosensing garment connector and a shoulder strap electrode of FIG. 28A.

FIG. 28D is a diagram of the biosensing garment connector 2340 of FIG. 28A, including electrodes "1," "2" and "3," and connectors "B1" and "B2," and FIG. 28E is a further diagram of the biosensing garment connector 2340 of FIG. 28A, also showing a shoulder strap electrode "4." As noted above, electrode "3" is optional, and can serve as a signal ground. Also, as noted above, electrode "2" is optional (i.e., electrodes "2" and "4" may both be included in the biosensing garment and/or used, or only one of them may be included in the biosensing garment and/or used). In some embodiments where electrode "3" is omitted, the following configurations (specifying which electrodes are "active," in other words, which electrodes are being actively measured and/or monitored) can successfully capture ECG signal(s):

1. Electrodes 1 and 2 active
2. Electrodes 1 and 4 active
3. Electrodes 1, 2, and 4 active The locations marked "B1" and "B2" in FIGS. 28B, 28D and 28E correspond to electrical connection points (e.g., which can also comprise one or more of: a snap cap, a socket, a stud, a post, (e.g. an S-spring, ring-spring, prong type), a rivet, a cover button, and/or the like) for a RIP breathing circuit. In some embodiments, "B1" and "B2" are not electrodes.

Figure 29:
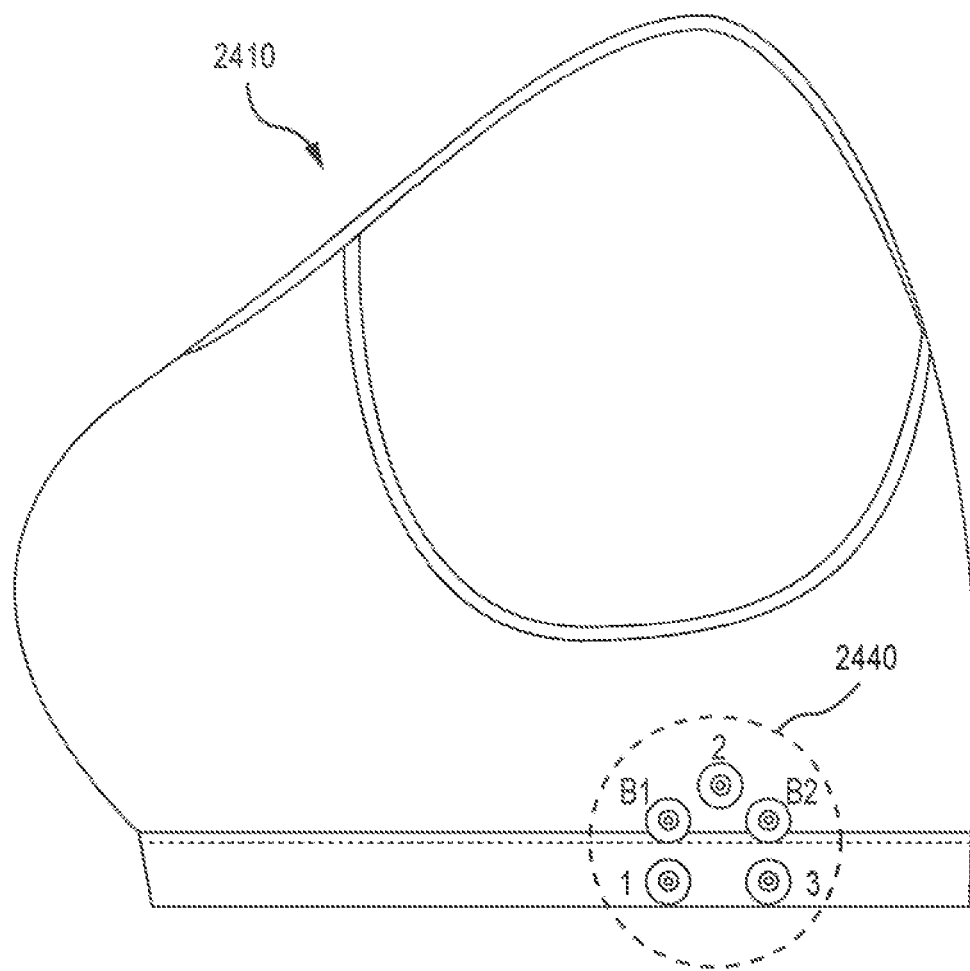
FIG. 29 shows an exterior view of a biosensing garment including an electrode configuration, according to an embodiment.

FIG. 29 shows an exterior view of a biosensing garment 2410 including an electrode array 2440, according to an embodiment. Specifically, FIG. 29 shows an exterior view of a sports bra 2410 that includes 3 or 4 active ECG electrodes (each of which consists of 1 brass snap cap), of which the third or fourth electrode is a ground electrode, and a RIP breathing circuit (including the 2 remaining snap caps). In some embodiments, at least one of the ECG electrodes is a ground electrode. The 3 ECG electrodes are located where the transmitter connects to the garment; the electrodes are pressed through the fabric, and the snap caps come in contact with the skin, while the corresponding sockets face outwardly for connection to a transmitter or other communications and/or measurement device. A fourth electrode (see, e.g., snap 2430B FIG. 30A), which is optional, can be electrically connected (e.g., via a conductive pathway) to any one of the 3 ECG electrodes and disposed in any location on the garment, and may improve the signal quality captured when compared to the 3 ECG electrodes only. In some such embodiments, all four snaps are electrically active and/or used for a given biosensing application. In other such embodiments, the electrode to which the fourth electrode is electrically connected in electrically inactive.

Figure 30A:
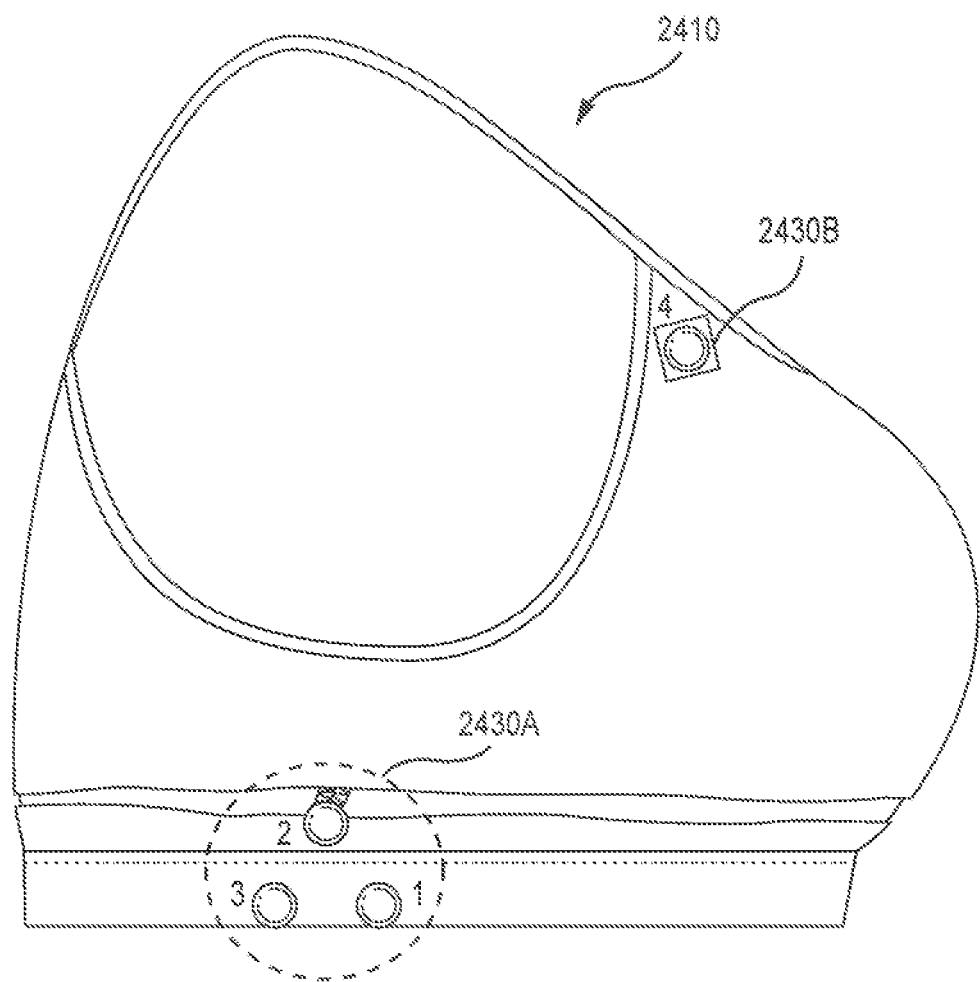
FIG. 30A shows an interior view of the biosensing garment of FIG. 29.
Figure 30B:
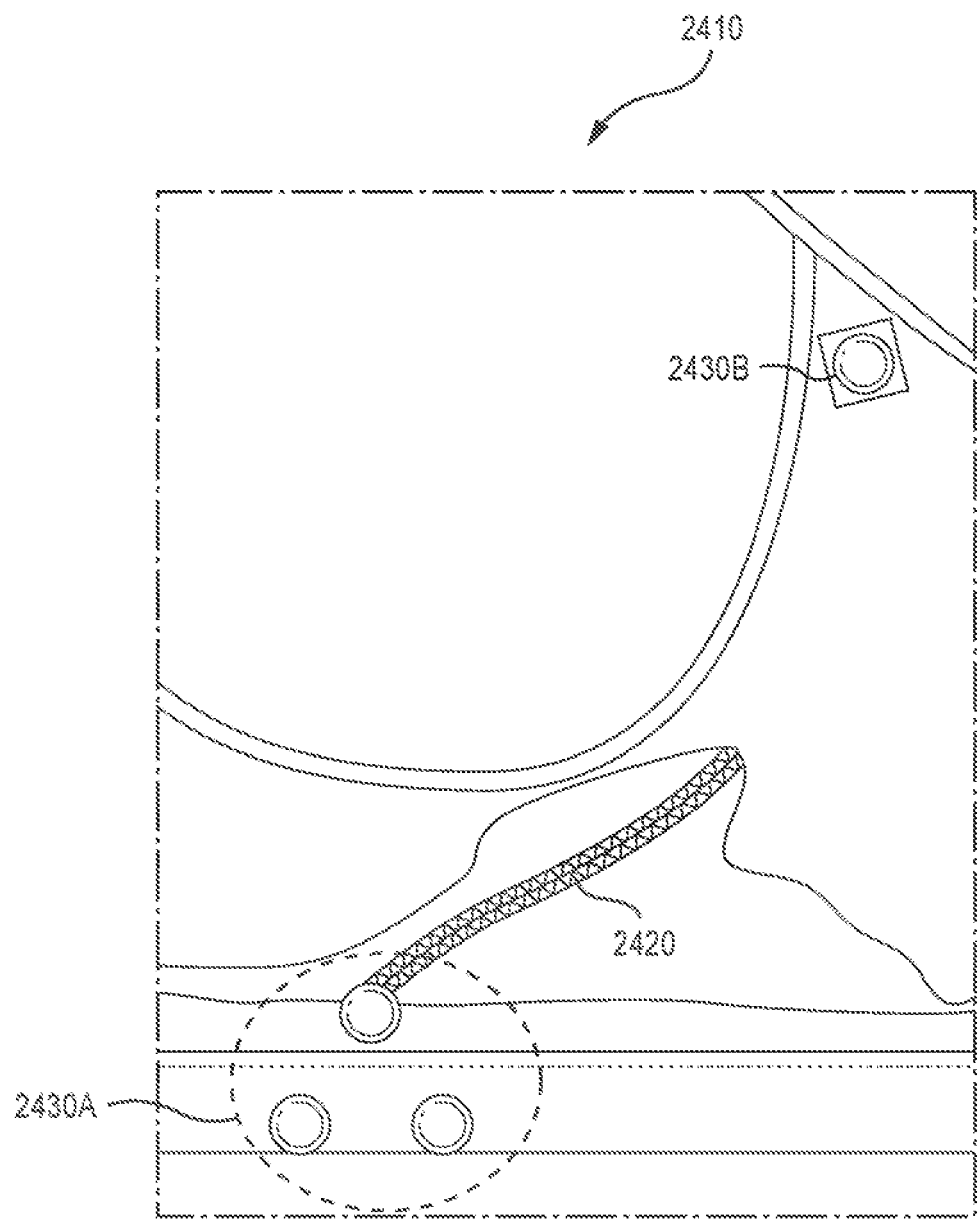
FIG. 30B shows a further interior view of the biosensing garment of FIG. 29.
Figure 30C:
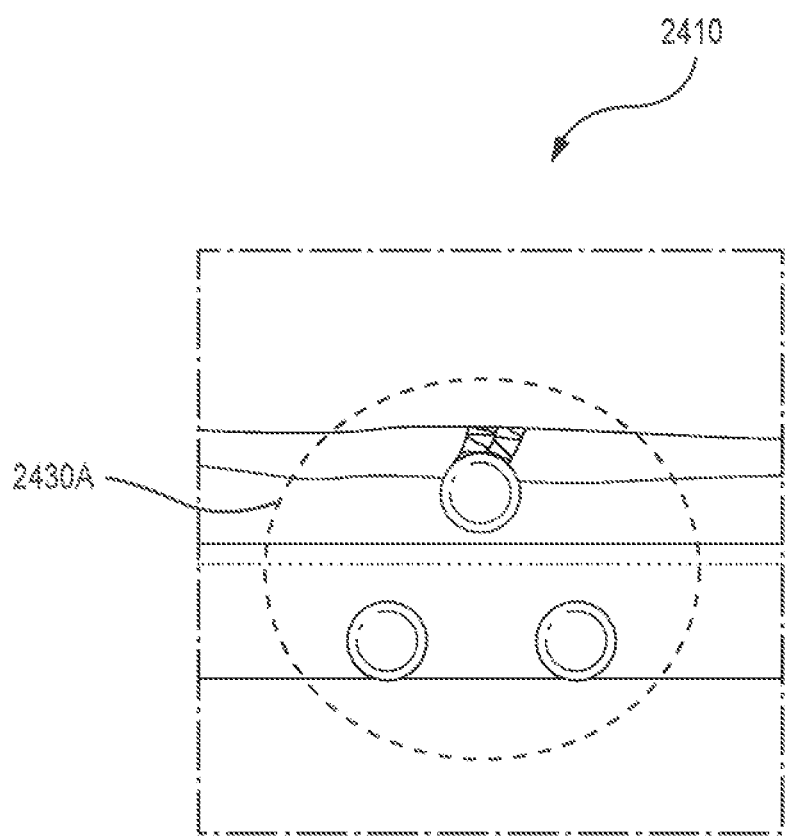
FIG. 30C shows a further interior view of the biosensing garment of FIG. 29.

FIG. 30A shows an interior view of the biosensing garment 2410 of FIG. 29, and illustrates electrode array 2430A. Electrode "1" can be used for sensing ECG signals. Electrode "2" can be used alone, or in conjunction with electrode "4" (2430B) (to which it is electrically coupled via a conductive pathway, partially visible in FIG. 30A), or electrode "4" (2430B) can be used alone (e.g., electrode "2" would be covered with cloth of the biosensing garment and not placed in contact with the skin of a wearer during use). Electrode "4" (2430B) can be disposed in/on the front of the biosensing garment 2410 (e.g., the "chest" or on a front portion of a shoulder strap thereof), or in/on the back of the biosensing garment 2410 (e.g., a rear portion of a shoulder strap thereof). FIGS. 30B and 30C show a further/detail interior views of the biosensing garment 2410 of FIG. 29. FIG. 30B shows a portion of the biosensing garment 2410 pulled away to reveal the conductive pathway 2420.

Figure 31:
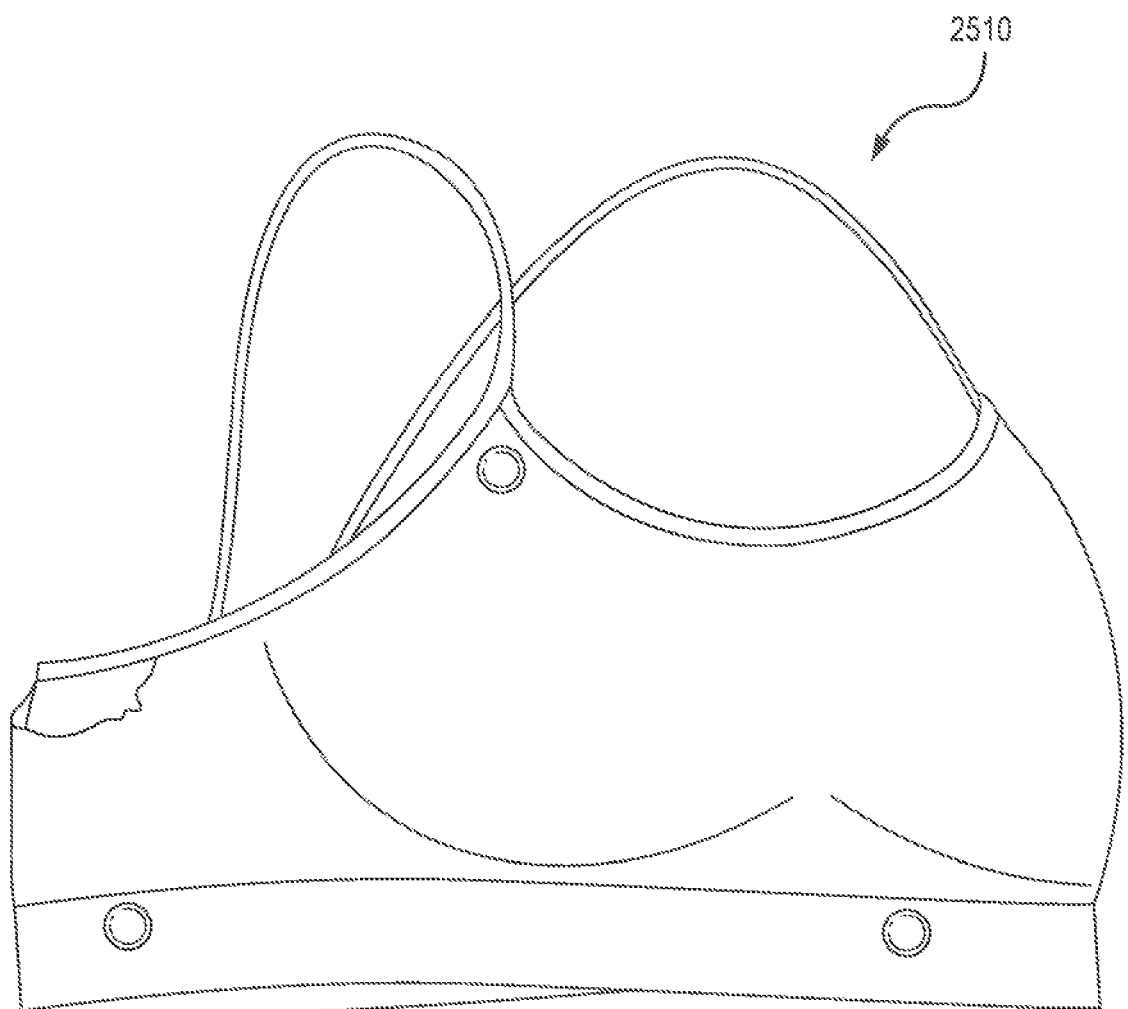
FIG. 31 shows an interior view of a biosensing garment including a snap electrode configuration, according to an embodiment.

FIG. 31 shows an interior view of a biosensing garment 2510 including a snap electrode configuration, according to an embodiment. Specifically, FIG. 31 shows an interior view of a sports bra 2510 that includes 3 ECG electrodes (one positive electrode, one negative electrode, and one ground electrode), each of which consists of 1 brass snap cap configured to contact the skin of a wearer. The ECG electrodes are snap caps that can be located anywhere on the bio-sensing garment 2510. In use, the electrodes are electrically coupled to a 'snap connector', which receives a transmitter (or other communications or measurement device), via conductive pathways that can be, e.g., wire, conductive elastic band, knitted conductive trace, or any other suitable conductor. Although the electrode configuration shown in FIG. 31 comprises snap caps, in some embodiments the electrode configuration can instead include rivets, or can include a combination of snap caps and rivets, etc.

Figure 32:
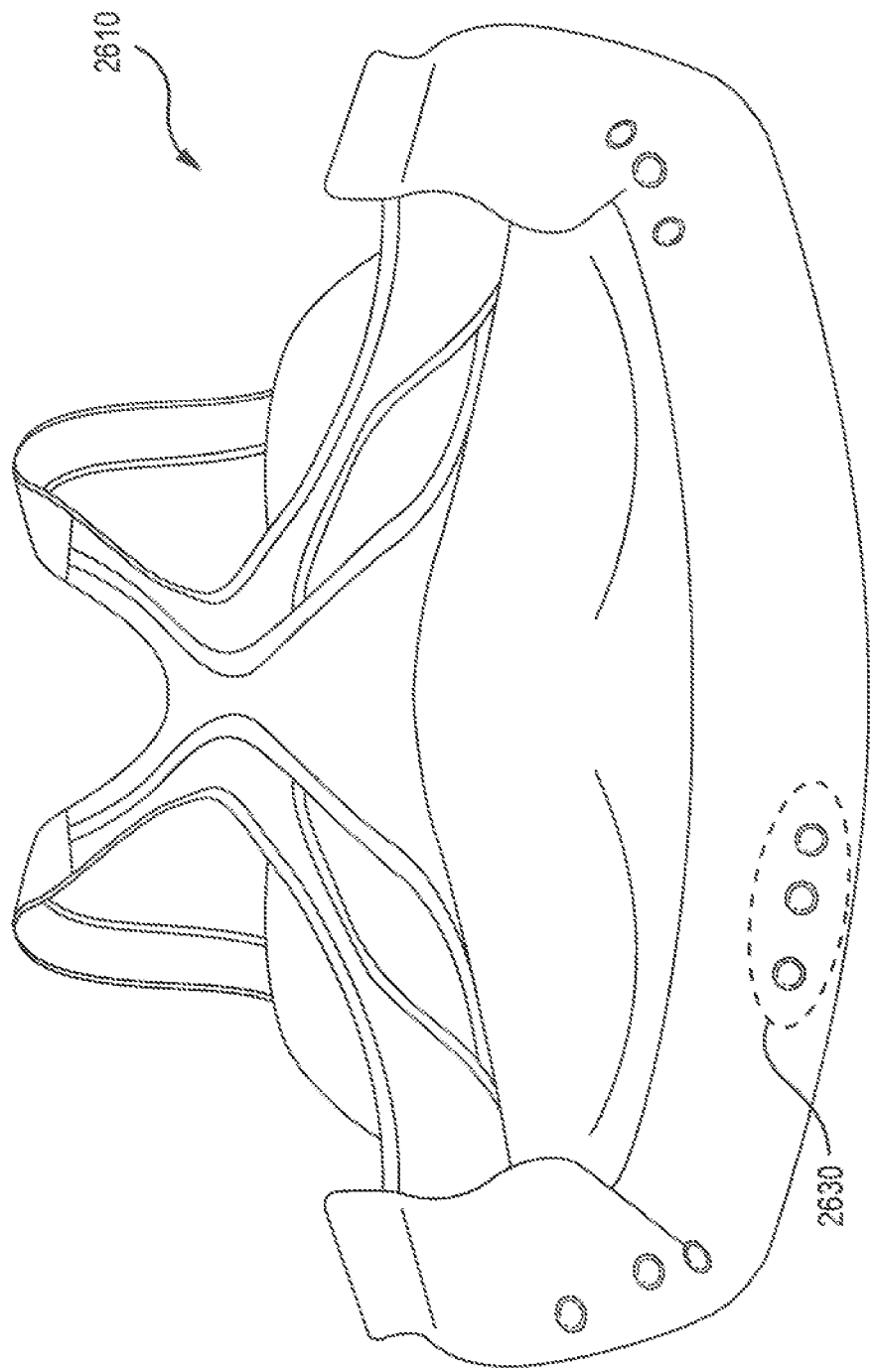
FIG. 32 shows an interior view of a biosensing garment including a rivet electrode configuration, according to an embodiment.

FIG. 32 shows an interior view of a biosensing garment 2610 including electrode arrays 2630 that include rivet electrodes, according to an embodiment. Specifically, FIG. 32 shows an interior view of a sports bra 2610 that includes 3 ECG electrodes (one positive electrode, one negative electrode, and one ground electrode), each of which includes an electrode array 2630 (also "cluster," "grouping" or "configuration") of 3 rivets. In some embodiments, the ground electrode is disposed on a back side of the garment (i.e., a portion of the garment that is configured to contact a wearer's back during use). In some embodiments, the biosensing garment 2610 interfaces with hardware (e.g., a transmitter) and/or firmware that are configured to process signals from the electrodes in a configuration in which the ground electrode is disposed on a back side of the garment. In other embodiments, the biosensing garment 2610 interfaces with hardware (e.g., a transmitter) and/or firmware that are configured such that the function (e.g., ground or measuring) of the each of the electrodes of the electrode array 2630 is interchangeable. Said another way, the electrode that is disposed on the back side of the garment may be selected to function as the positive measuring electrode, the negative measuring electrode, or the ground.

Figure 33:
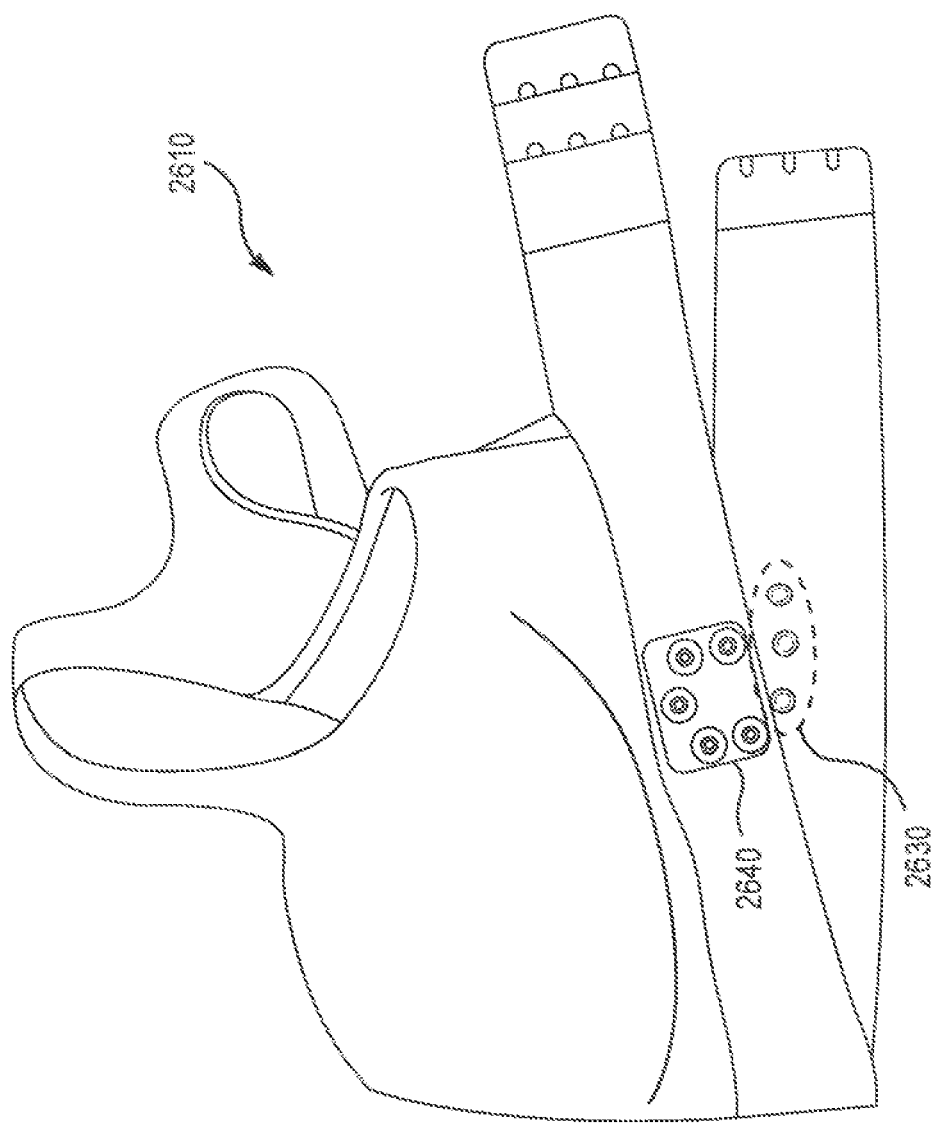
FIG. 33 is a side view of the biosensing garment of FIG. 32.
Figure 34:
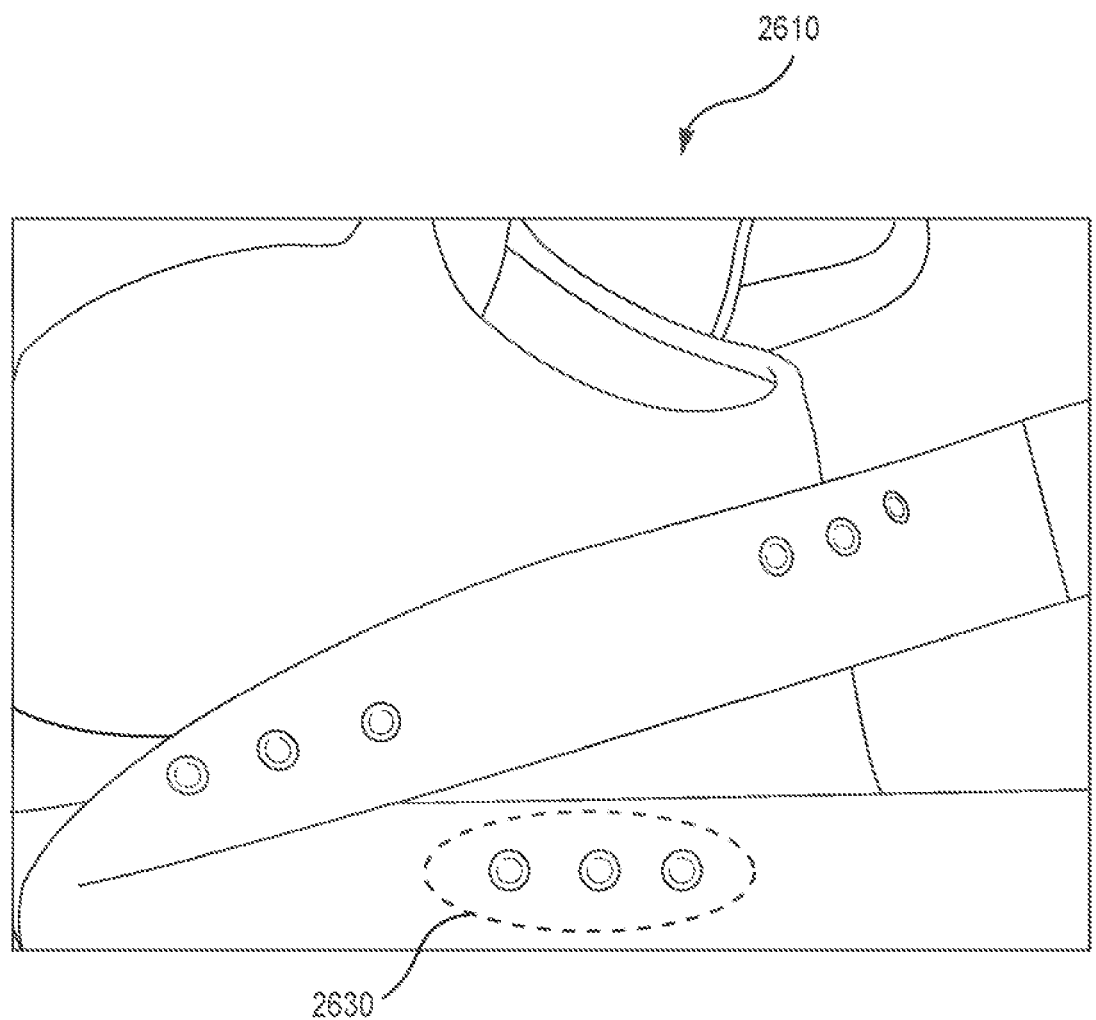
FIG. 34 is a further side view of the biosensing garment of FIG. 32.

The rivets of FIG. 32 are about 9 mm in diameter and are spaced about 10 mm apart from one another within an electrode array. Each electrode array of 3 rivets makes up one ECG electrode, where the 3 rivets are all connected to one conductive pathway that leads to the 'snap connector' that receives the transmitter. FIG. 33 is a side view of the biosensing garment 2610 of FIG. 32, showing one of the three-rivet electrode arrays, 2630, disposed on an interior surface of the sports bra 2610 chest band, and showing a biosensing garment connector 2640 (for mechanical and electrical connection to a transmitter during use), which includes an electrode array and, optionally, two connection points for a RIP sensor circuit, on an external surface of the sports bra 2610 chest band. FIG. 34 is a further side view of the biosensing garment of FIG. 32, showing three of the three-rivet electrode arrays 2630 disposed on an interior surface of the sports bra chest band. Although shown in FIGS. 32-34 to comprise rivets, in some embodiments the electrode configuration can instead include snap caps, or can include a combination of snap caps and rivets, etc.

Figure 35:
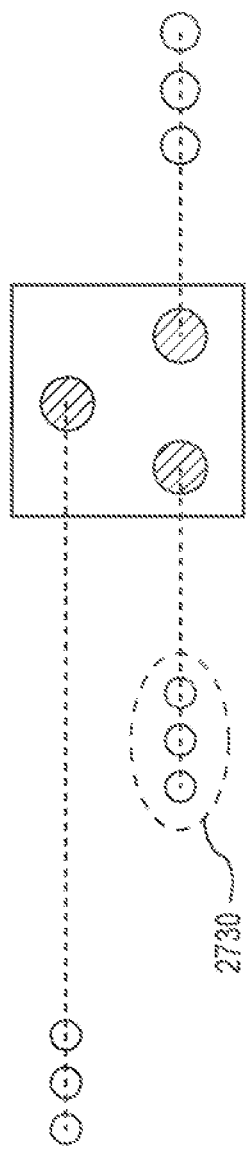
FIG. 35 is a schematic drawing of a plurality of three-electrode (e.g., snap caps and/or rivets) electrode arrays and their respective correspondences to snap-cap terminals of a biosensing garment connector, according to an embodiment.

FIG. 35 is a schematic drawing of a plurality of three-electrode (e.g., snap caps and/or rivets) electrode arrays 2730 and their respective correspondences to snap-cap terminals of a biosensing garment connector, according to an embodiment.

Printed Electrodes

Examples of electrodes 130 include film-based electrodes such as, printed electrodes as described in further detail below. As described herein, a plurality of electrode(s) 130 may be mechanically coupled to the biosensing garment 110, electrically coupled to the conductive pathway 120, and configured to contact skin of a wearer during use.

In some embodiments, a biosensing garment 110 comprises a fabric substrate (such as textile) having a first major surface, a second major surface opposite the first major surface, and a thickness. A conductor (such as conductive pathways 120 in FIG. 1) is disposed on or adjacent to the first major surface of the fabric substrate. A printed electrode is disposed on or adjacent to the second major surface of the fabric substrate and electrically coupled to the conductor through the thickness of the fabric substrate.

Wearable electronics such as biosensing garments (end the electronic textiles from which they are made) are subjected to different mechanical stresses than traditional electronic systems. For example, biosensing garments may be stretched during enrobing, disrobing, and wear (e.g., during physical activity of the wearer). This stretching can result in deformation of conductors and/or sensor elements that are embedded within and/or secured to a surface of the biosensing garment. As a result, wearable electronics often suffer from compromised performance after only limited period of use. Additionally, biosensing garment electrodes designed to contact a wearer's skin are often prone to shift during activity, resulting in inconsistent signal strength and/or intermittent signal reliability. Biosensing garment electrodes are also often of a fixed geometry and/or of a rigid construction, such that they are prone to making inadequate contact with the skin of a wearer (e.g., insufficient surface area, low conformality, etc.). According to embodiments of the present disclosure, improved electrodes are described that are "film" based, resulting in improved design flexibility, signal quality, durability, reliability.

Embodiments described herein relate generally to film-based electrodes for biosensing applications, such as biosensing garments. Referring to FIG. 1, in some embodiments, a biosensing garment such as 110 in FIG. 1 includes a substrate having one or more electrodes such as 130 in FIG. 1 mechanically coupled to a first surface thereof. For example, the electrode may be fixed to the first surface of the substrate, or may be disposed adjacent thereto. A conductor such as conductive pathways 120 in FIG. 1 is electrically coupled to the electrode, and can be mechanically coupled to the electrode, the substrate, or both. The conductor can be disposed on or adjacent to a second surface of the substrate that is opposite of the first surface of the substrate, and/or can be disposed on the first surface of the substrate, and/or can form part of the substrate (e.g., woven, knitted, or otherwise integrated therein). The substrate can comprise a fabric, for example an article of clothing or garment such as a shirt or sports brassiere, or a portion thereof, such as a segment of fabric for later incorporation into a garment or for use as a standalone accessory, such as an arm band, leg band, head band, wrist band, etc. As used herein, the term "fabric" can refer to cotton, polyester, lycra, spandex, bamboo, gore-tex, nylon, polypropylene, tencel, wool, x-static, or any other man-made or natural textile or other substrate material that is suitable for use in biosensing applications and/or performance sports clothing. Alternatively or in addition, the substrate can comprise a non-fabric, such as a thermoplastic, rubber, silicone, plastic, or any other suitable material.

The electrode 130 can be formed from one or more conductive inks, conductive pastes and/or conductive coatings, or any combination thereof. For example, an ink suitable for use in forming an electrode 130 can be silver, carbon, or graphene based. In other words, a conductive ink may include particles (e.g., microparticles and/or nanoparticles), flakes, threads, filaments, etc. In some embodiments, an electrode 130 includes a conductive polymer. The electrode 130 is mechanically coupled to the first surface of the substrate via application to the first surface of the substrate. The application can be performed by screen printing, inkjet printing, transfer printing, sublimation printing, pad printing, coating, transfer coating, spraying, extrusion, or any other suitable application technology. When incorporated in a biosensing garment 110, the electrode 130 can be used to detect biological signals of a wearer, for example electrocardiogram (ECG) and/or electromyogram (EMG) signals, and can be incorporated into any type of wearable garment or accessory. Printing the electrode 130 allows for the creation of the electrode 130 in any desired shape and size (e.g., rectangular, oblong, oval, circular, ring-shaped, etc.), and also allows for the placement of the electrode 130 directly onto the substrate. When applied directly to the surface of the substrate, the electrode 130 can exhibit high conformality with the substrate, such that the electrode 130 is less noticeable to a wearer, makes better contact with a wearer during use as compared with traditional electrode configurations, and/or may exhibit improved mechanical durability.

In some embodiments, rather than being applied directly to a surface of the substrate, the electrode 130 is printed onto a primer "layer," such as a thermoplastic adhesive film, prior to applying the electrode 130 to the substrate, at which point the electrode 130 can be affixed to the substrate, for example by heat-bonding. In some such embodiments, the primer layer comprises a non-conductive material, and includes a through-hole through which the electrode 130 makes physical contact with a connection point on the substrate (e.g. a conductive stitch) that electrically connects the printed electrode 130 to the conductor 130.

In some embodiments, described in further detail below, the substrate can be prepared with either a conductive or a non-conductive "primer," for example a thermoplastic film (such as thermoplastic polyurethane, "TPU"), a dielectric ink, paste or coating, or a conductive ink, paste or coating, prior to the application of the electrode 130. This approach can be used, for example, to aid in or improve the adhesion of the electrode 130 material to the substrate, to create an insulation barrier between the electrode 130 and the substrate, to reduce the porosity of the substrate surface, and/or, in the case of conductive primers, to affect electrical properties of the electrode 130 and/or to improve the conductivity of the electrical connection between the conductor 120 trace and the electrode 130.

Figure 36:
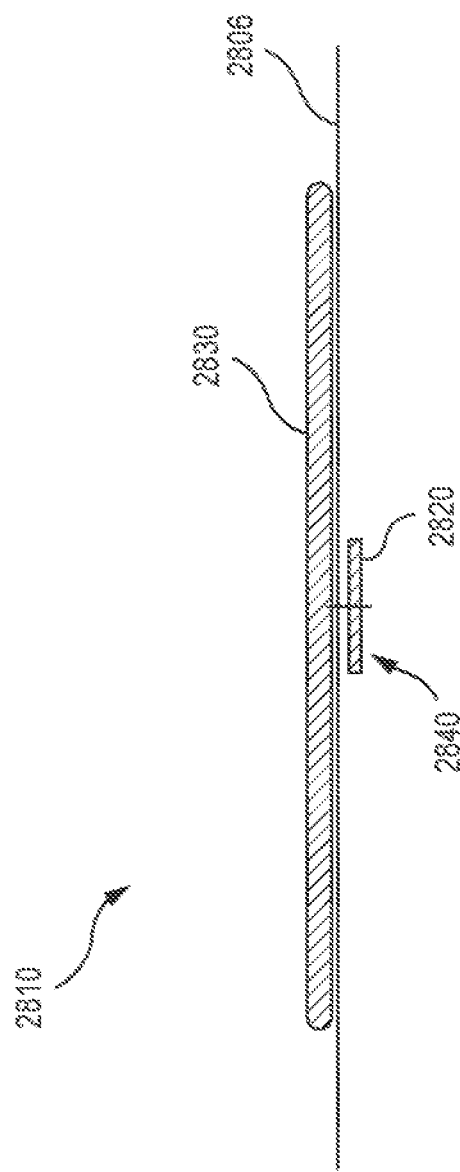
FIG. 36 shows a cross-sectional view of an electrode-bearing substrate, according to an embodiment.

FIG. 36 shows a cross-sectional view of an electrode-bearing substrate, according to an embodiment. As shown, an electrode 2830 (e.g., a printed electrode) is disposed on a first surface of a substrate 2806, e.g., forming part of a biosensing garment 2810, and a conductor 2820 (such as conductive pathways 120 in FIG. 1) is disposed on a second surface of the substrate 2806. A connection point 2840 extends through the substrate 2806 and electrically connects the electrode 2830 with the conductor 2820. The connection point can comprise, for example, a conductive stitch formed from a conductive thread, wire, filament, or other material that is passed through the substrate 2806 and, optionally, mechanically fixes the conductor 2820 to the substrate 2806. In some embodiments, the conductive stitch is formed in the substrate 2806 prior to the application of the electrode 2830. In other embodiments, the conductive stitch is formed in the substrate 2806 after the application of the electrode 2810.

Figure 37:
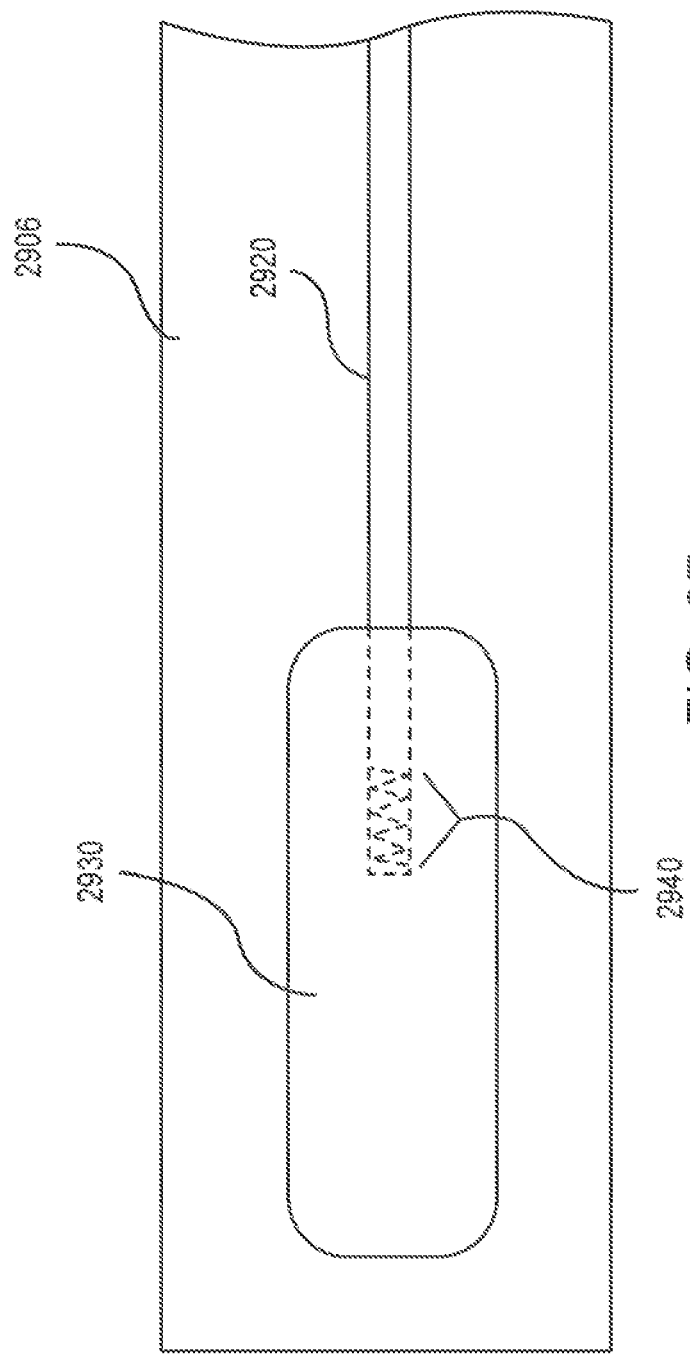
FIG. 37 shows a plan view of an electrode and a conductor connected via a connection point, according to an embodiment.

FIG. 37 shows a plan view of an electrode and a conductor connected via a connection point, according to an embodiment. As shown, a region of the oblong electrode 2930 (e.g., a printed electrode) overlaps with an area of the conductor 2920 (such as conductive pathways 120 in FIG. 1), and a connection point 2940 such as electrical connectors 140 in FIG. 1 (which may also be referred to as a connection "region"), in the form of a zig-zag conductive stitch pattern formed from a conductive thread, wire, filament, or other material, is disposed within at least a portion of the region of overlap between the electrode 2930 and the conductor 2920. In some embodiments, the conductive stitch pattern comprises stitches that penetrate the substrate 2906 (e.g., a fabric garment or portion thereof). In other words, the stitches are formed "through" the substrate 2906. In some embodiments, the electrode 2930 is disposed on a first surface of a substrate 2906 and the conductor 2920 is disposed on a second surface of the substrate 2906 that is opposite the first surface of the substrate 2906. In other embodiments, the conductor 2920 is disposed on a first surface of a substrate 2906 and the electrode 2930 is also disposed on the first surface of a substrate 2906 (i.e., the electrode 2930 is applied directly to the first surface of the substrate and directly onto a portion of the conductor 2920). Although depicted as a zig-zag stitch, other types of stitch are also contemplated, such as a straight, fly, running, back, lock, chain, overcast, slip, catch, hemming, and/or cross stitch. Also, other means of attachment are contemplated, such as stapling and/or conductive adhesive.

Figure 38:
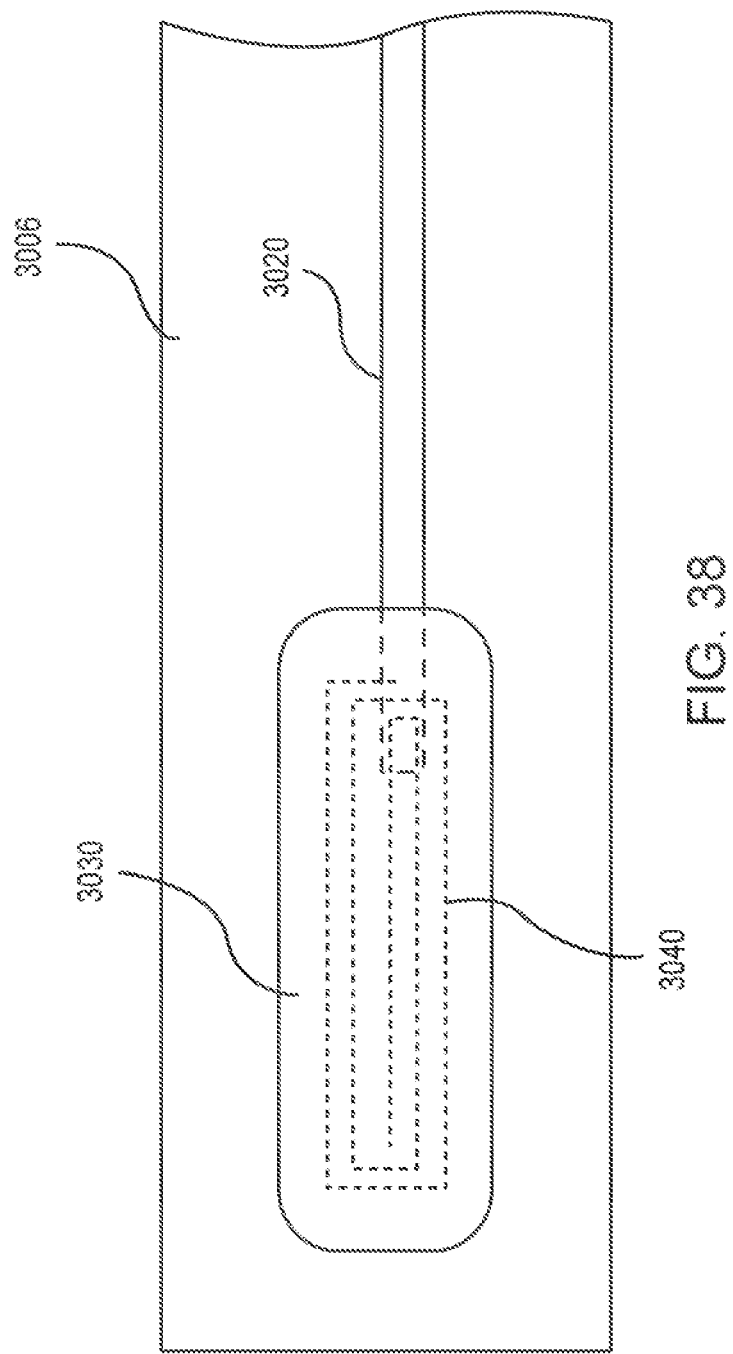
FIG. 38 shows a plan view of an electrode and a conductor connected via a connection point, according to an embodiment.

FIG. 38 shows a plan view of an electrode and a conductor connected via a connection point, according to an embodiment. As shown, an oblong electrode 3030 (e.g., a printed electrode) overlaps with a conductor 3020, and a connection point 3040, in the form of a running conductive stitch, having a rectangular spiral pattern, formed from a conductive thread, wire, filament, or other material, is disposed on a portion of the region of overlap between the electrode 3030 and the conductor 3020, and also occupies a portion of the non-overlapping region of the electrode 3030. In some embodiments, the running conductive stitch penetrates the substrate 3006 (e.g., a fabric garment or portion thereof). In other words, the stitching is formed "through" the substrate 3006. In some embodiments, the electrode 3030 is disposed on a first surface of a substrate 3006 and the conductor 3020 is disposed on a second surface of the substrate 3006 that is opposite the first surface of the substrate 3006. In other embodiments, the conductor 3020 is disposed on a first surface of a substrate 3006 and the electrode 3030 is also disposed on the first surface of a substrate 3006 (i.e., the electrode 3030 is applied directly to the first surface of the substrate and directly onto a portion of the conductor 3020). Although depicted as a straight stitch, other types of stitch are also contemplated, such as zig-zag, fly, running, back, lock, chain, overcast, slip, catch, hemming, and/or cross stitch. Also, other means of attachment are contemplated, such as stapling and/or conductive adhesive.

Figure 39:
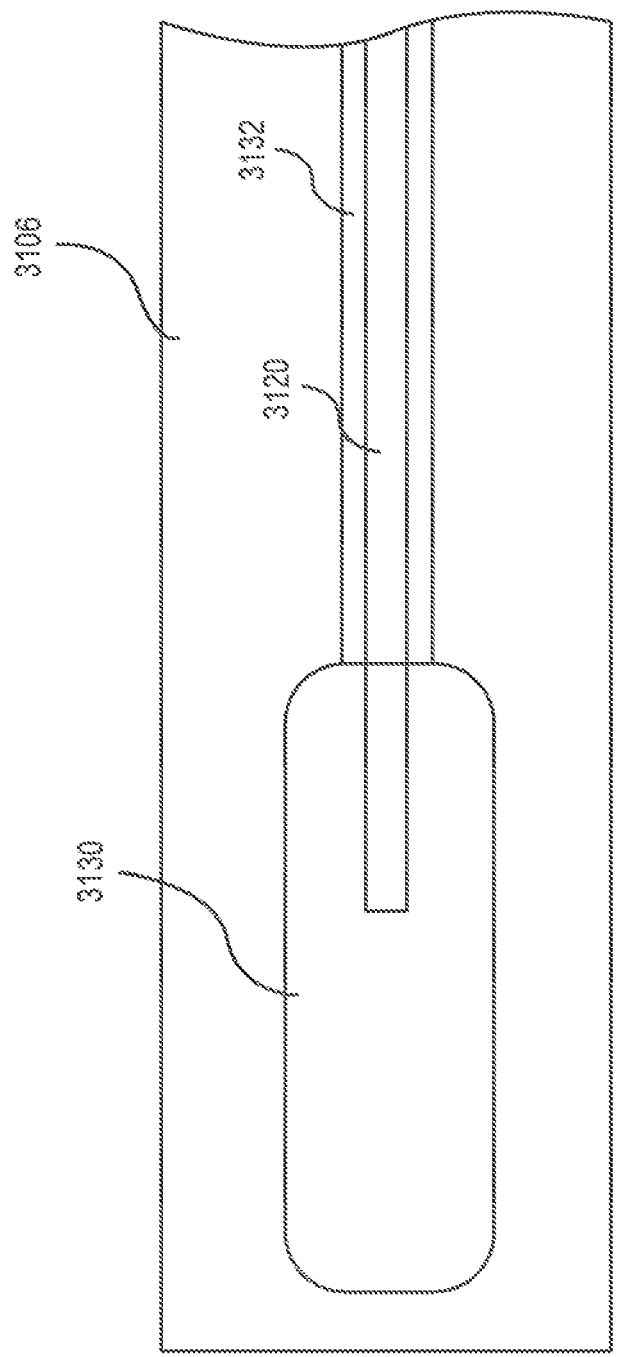
FIG. 39 shows a plan view of an electrode partially overlapping with a conductor, according to an embodiment.

FIG. 39 shows a plan view of an electrode partially overlapping with a conductor, according to an embodiment. An oblong electrode 3130 (e.g., a printed electrode) overlaps with a conductor 3120 that is disposed within a substrate 3106, and the electrode 3130 is applied directly onto the conductor 3120 such that an electrical connection is formed in the region of overlap therebetween. An optional electrically insulating "isolation" layer 3132 is also shown, covering a portion of the conductor 3120 that does not overlap with the electrode 3130. The isolation layer 3132 can comprise any electrical insulator, such as a thermoplastic, plastic, rubber, dielectric ink or other material form, fabric, and/or the like. In some embodiments, rather than being disposed within the substrate 3106 itself, the conductor 3120 of FIG. 39 can be a conductive trace (for example, a printed trace) disposed on the same surface of the substrate 3106 as the electrode 3130.

Figure 40:
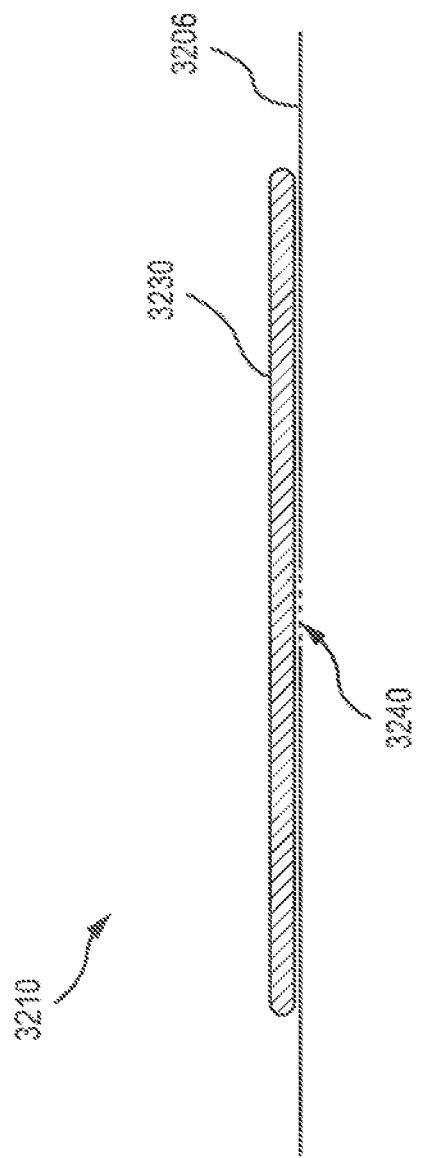
FIG. 40 shows a cross-sectional view of an electrode-bearing substrate, according to an embodiment.

FIG. 40 shows a cross-sectional view of an electrode-bearing substrate, forming part of a biosensing garment 3210, according to an embodiment. An electrode 3230 (e.g., a printed electrode) is disposed on a first surface of a substrate 3206, and a connection region 3240 within which a conductive pathway that is knitted with, embedded in, or otherwise incorporated into the substrate 3206, is exposed. As such, when the electrode 3230 is applied (e.g., printed) onto the substrate 3206, electrical connectivity is established between the electrode 3230 and the conductive pathway exposed by connection region 3240. In some such embodiments, a further connection method can also be employed, such as conductive stitching, conductive adhesive, etc., for example, to enhance the electrical connection between the conductive pathway and the electrode 3230. In some embodiments, multiple connection regions 3240 can be used.

Figure 41:
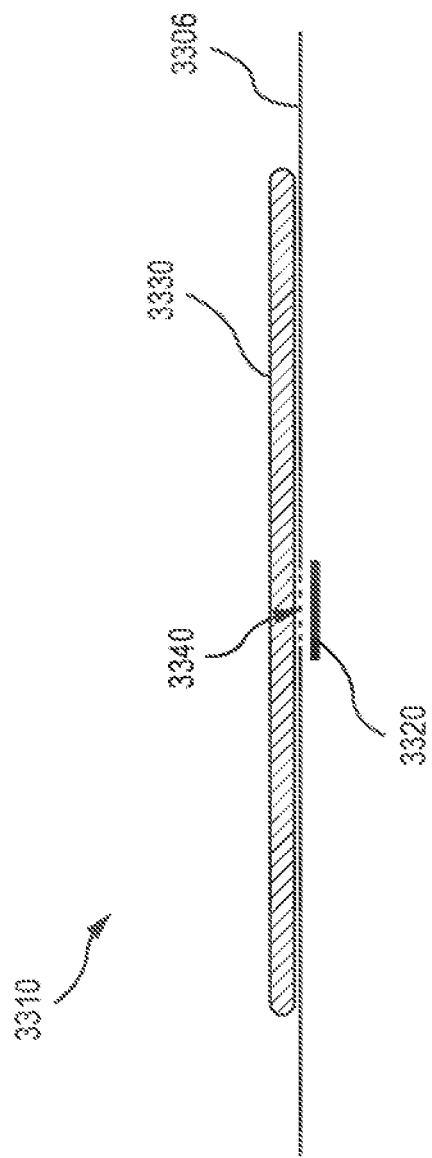
FIG. 41 shows a cross-sectional view of an electrode-bearing substrate, according to an embodiment.

FIG. 41 shows a cross-sectional view of an electrode-bearing substrate, forming part of a biosensing garment 3310, according to an embodiment. An electrode 3330 (e.g., a printed electrode) is disposed on a first surface of a substrate 3306, and a conductor 3320 is disposed on a second surface (opposite the first surface) of the substrate 3306. A connection point 3340, which can comprise a stitch, a rivet, a conductive paste, a conductive ink, and/or a hole through the substrate 3306, is disposed in the substrate 3306 within a region of the substrate 3306 that is disposed between the electrode 3330 and the conductor 3320. The connection point 3340 establishes electrical connectivity between the electrode 3330 and the conductor 3320, either directly via conductive stitches or conductive hardware, or indirectly by virtue of the printed electrode contacting the conductor 3320 via the hole in the substrate 3306, and can also mechanically secure the conductor 3320 to the substrate 3306.

Figure 42:
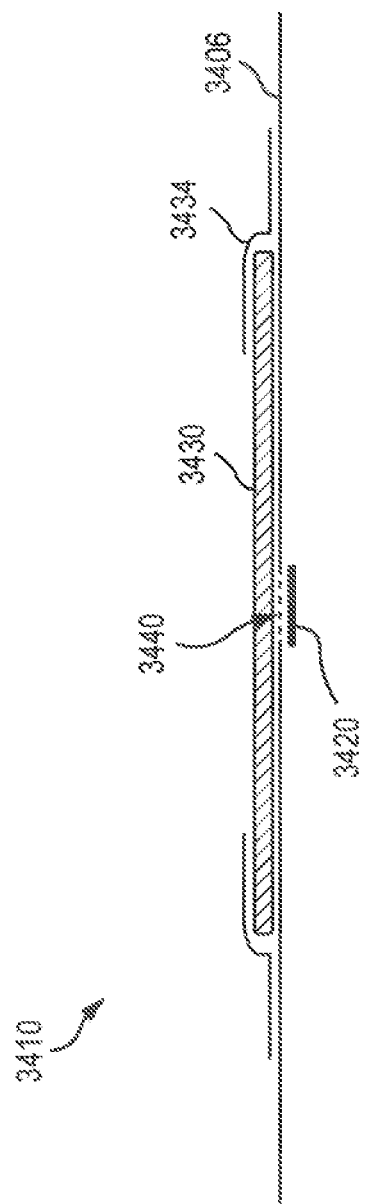
FIG. 42 shows a cross-sectional view of an electrode-bearing substrate, according to an embodiment.
Figure 43:
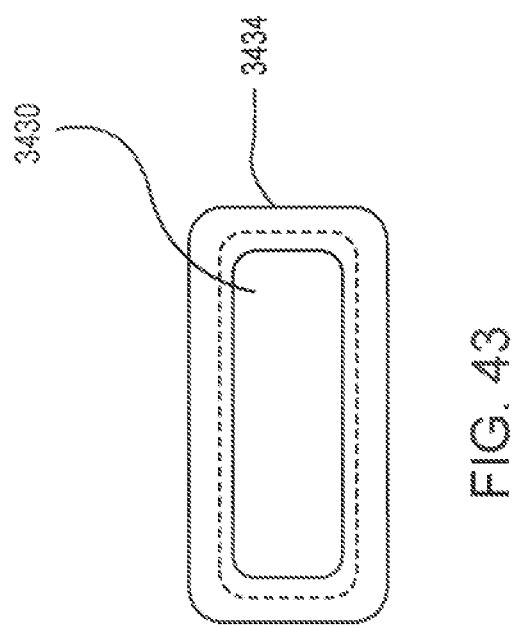
FIG. 43 shows a plan view of the electrode of FIG. 42.

FIG. 42 shows a cross-sectional view of an electrode-bearing substrate, forming part of a biosensing garment 3410, according to an embodiment. An electrode 3430 (e.g., a printed electrode) is disposed on a first surface of a substrate 3406, and a conductor 3420 is disposed on a second surface (opposite the first surface) of the substrate 3406. A connection point 3440, which can comprise a stitch, a rivet, and/or a hole through the substrate 3406, is disposed in the substrate 3406 within a region of the substrate 3406 that is disposed between the electrode 3430 and the conductor 3420. The connection point 3440 establishes electrical connectivity between the electrode 3430 and the conductor 3420, either directly via conductive stitches or conductive hardware, or indirectly by virtue of the printed electrode contacting the conductor 3420 via the hole in the substrate 3406, and can also mechanically secure the conductor 3420 to the substrate 3406. Edges of the electrode 3430 are also covered with a frame 3434, e.g., comprising a thermoplastic film such as TPU, or a printed layer or coating (e.g., using a silicone-based ink, a plastisol-based ink, etc.), applied using any of the application methods described herein. The frame can be solid (see, e.g., FIG. 43), perforated (see, e.g., FIG. 47), or patterned (see, e.g., FIG. 48). FIG. 43 shows a plan view of the electrode 3430 and frame 3434 of FIG. 42, showing the frame 3434 overlapping the edged of the electrode 3430.

Figure 44:
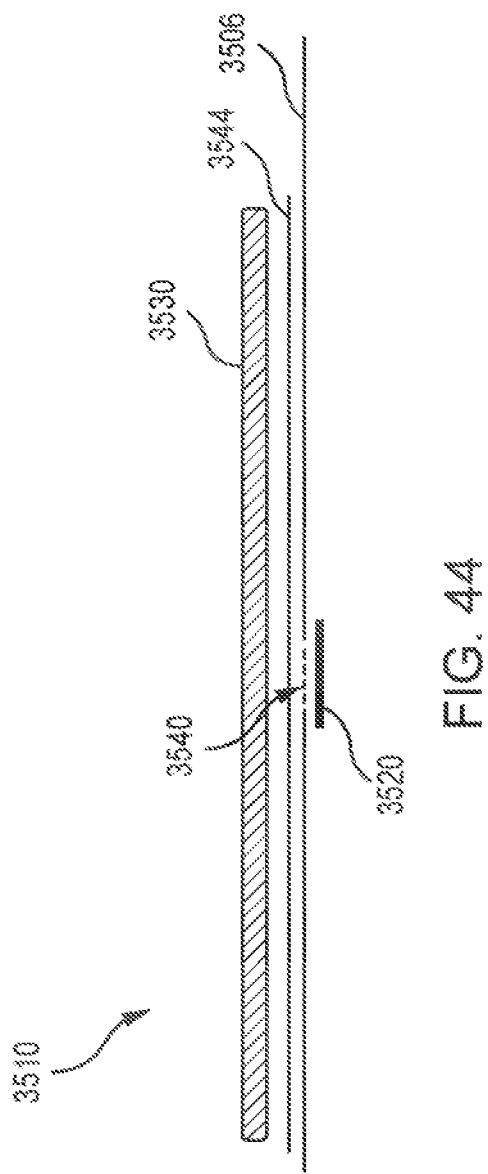
FIG. 44 shows a cross-sectional view of an electrode-bearing substrate, according to an embodiment.

FIG. 44 shows a cross-sectional view of an electrode-bearing substrate, forming part of a biosensing garment 3510, according to an embodiment. An electrode 3530 (e.g., a printed electrode) is disposed on a conductive primer layer 3544. The conductive primer layer 3544 is disposed on a first surface of a substrate 3506. A conductor 3520 is disposed on a second surface (opposite the first surface) of the substrate 3506. A connection point 3540, which can comprise a stitch, a rivet, and/or a hole through the substrate 3506, is disposed in the substrate 3506 within a region of the substrate 3506 that is disposed between the electrode 3530/conductive primer layer 3544 and the conductor 3520. The conductive primer layer 3544 can comprise a conductive tape or other conductive sheet material, such as anisotropic conductive film, conductive silicone rubber sheeting, conductive silicone, flexible printed circuit board material (e.g., Pyralux), pressure-sensitive conductive sheet (e.g., Velostat/Linqstat), stretchable inks, conductive polyamides (e.g., Zytel®), and/or the like. The connection point 3540 establishes electrical connectivity between the conductive primer layer 3544, the electrode 3530 and the conductor 3520, for example via conductive stitches or conductive hardware, and can also mechanically secure the conductor 3520 to the substrate 3506 (and, optionally, to the conductive primer layer 3544).

Figure 45:
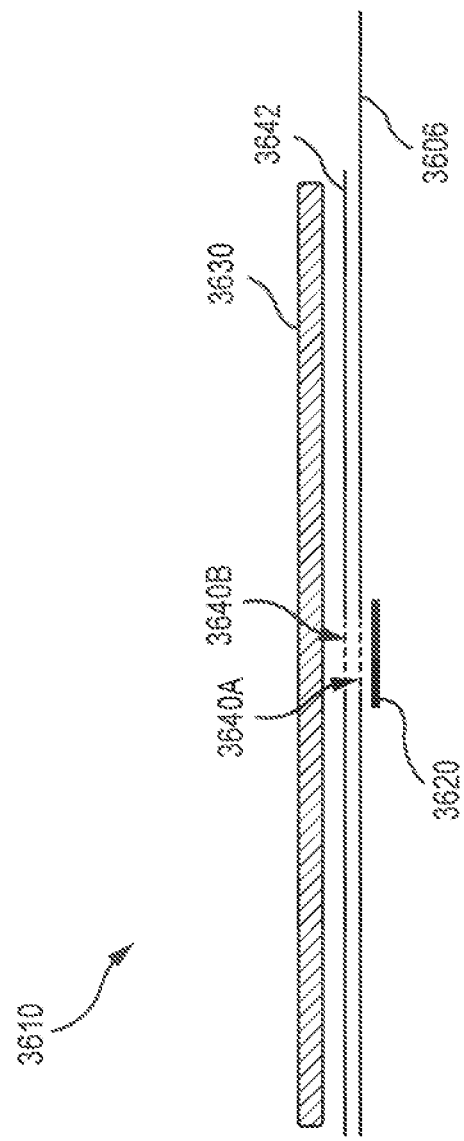
FIG. 45 shows a cross-sectional view of an electrode-bearing substrate, according to an embodiment.

FIG. 45 shows a cross-sectional view of an electrode-bearing substrate, forming part of a biosensing garment 3610, according to an embodiment. An electrode 3630 (e.g., a printed electrode) is disposed on a non-conductive primer layer 3642. The non-conductive primer layer 3642 is disposed on a first surface of a substrate 3606. A conductor 3620 is disposed on a second surface (opposite the first surface) of the substrate 3606. The substrate 3606 includes/defines a first connection point 3640A, which can comprise a stitch, a rivet, and/or a hole through the substrate 3606, within a region of the substrate 3606 that is disposed between the electrode 3630, non-conductive primer layer 3642, and the conductor 3620. The non-conductive primer layer 3642 includes/defines a second connection point 3640B, which can comprise a stitch, a rivet, and/or a hole through the non-conductive primer layer 3642, within a region of the non-conductive primer layer 3642 that is disposed between the electrode 3630/non-conductive primer layer 3642 and the conductor 3620. The first connection point 3640A and the second connection point 3640B may be substantially aligned with one another, and may share one or more common stitches, rivets, etc. The non-conductive primer layer 3642 can comprise an insulating tape or other non-conductive sheet material, such as silicone rubber, silicone, polyamide, and/or the like. The connection points 3640A and 3640B, collectively, establish electrical connectivity between the electrode 3630 and the conductor 3620, for example via conductive stitches or conductive hardware, and can also mechanically secure the conductor 3620 to the substrate 3606 (and, optionally, to the non-conductive primer layer 3642).

Figure 46:
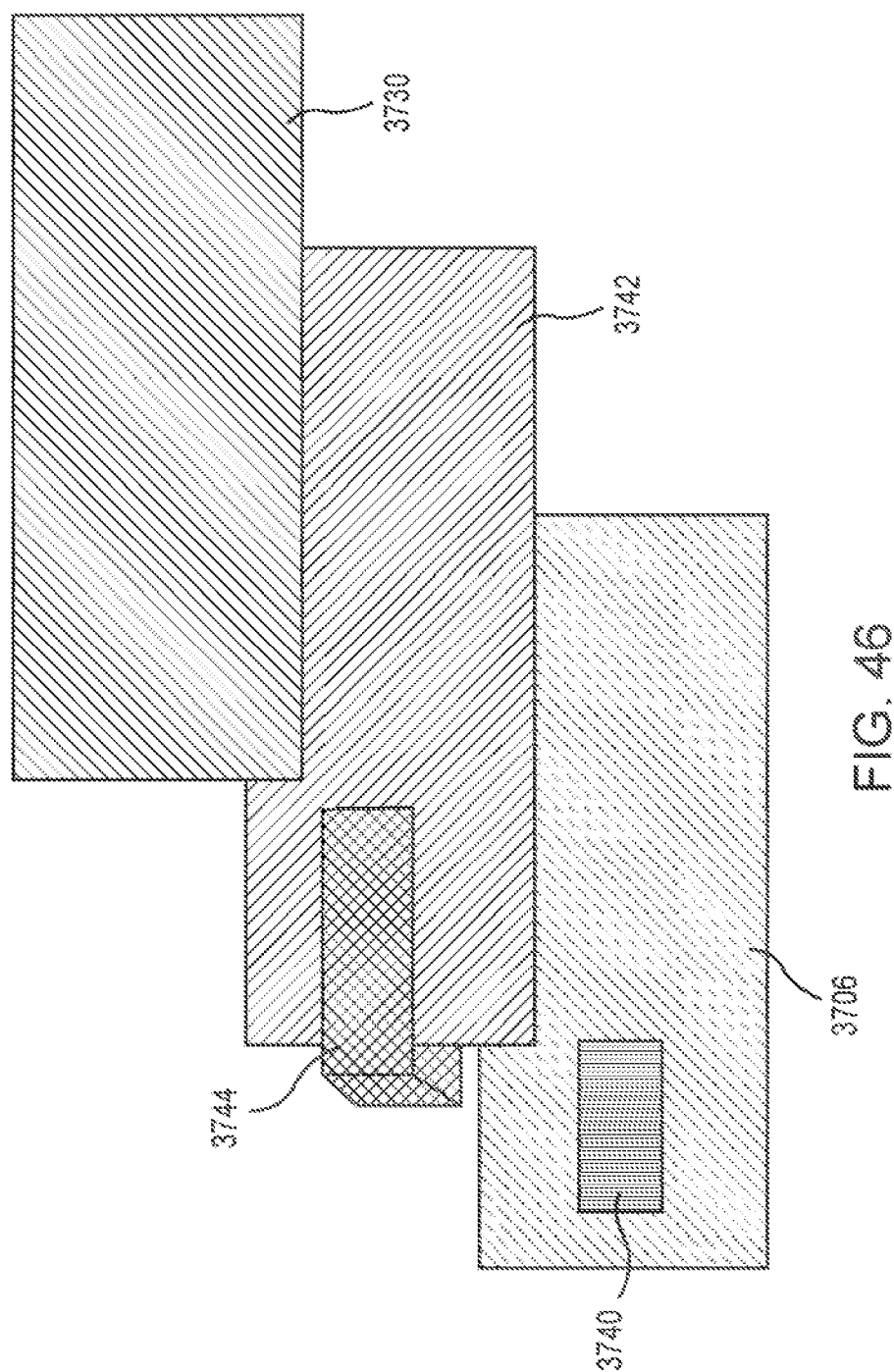
FIG. 46 shows an electrode assembly configuration, according to an embodiment.

FIG. 46 shows an electrode assembly configuration, according to an embodiment. As shown in FIG. 46, a fabric substrate 3706 is disposed at the bottom of a layered stack, and includes a stitched region 3740 (e.g., a "bar tack," or a series of machine-made or handmade stitches, such as a lockstitch, chain stitch, or any other suitable stitch pattern). Stitches of the stitched region 3740 are formed from one or more conductive threads (or fibers, filaments, yarns, wires, etc.), where all or part of the one or more filaments is electrically conductive (e.g., X-Static fiber and/or any suitable conductive material, such as a stainless steel plated material, other types of metal-clad materials, metallic threads, etc.). Disposed above the fabric substrate 3706 is an adhesive layer 3742 which can be insulating, and can comprise an elastomer such as TPU (e.g., ET312) or any other suitable barrier layer material, such as those described herein. A conductive fabric segment 3744 is wrapped about a first edge of the adhesive layer 3742 such that a portion of the adhesive layer 3742 is received or "enveloped" by the conductive fabric segment 3744. The conductive fabric segment 3744 can comprise a silver-plated nylon such as Medtex, or a conductive Velcro®, a conductive knit, a conductive film such as Velostat, flexible Pyralux, electrically conductive silicone sheeting, conductive polyethylene, Zytel polyamide, and/or the like). A conductive pathway is disposed beneath the fabric substrate 3706 (i.e., on a major surface of the fabric substrate 3706 opposite the major surface of the fabric substrate 3706 that is shown in FIG. 46), and the stitched region 3740 connects the conductive pathway to the conductive fabric segment 3744. During fabrication of the electrode assembly, a printed electrode 3730 is applied to a major surface of the adhesive layer 3742 (note that both major surfaces of the adhesive layer 3742 including a portion of the conductive fabric segment 3744). In other words, a portion of the conductive fabric segment 3744 serves as a substrate (or part of a substrate, where the substrate includes both the portion of the conductive fabric segment 3744 and a major surface of the adhesive layer 3742) onto which the printed electrode 3730 is applied. During fabrication, each of the fabric substrate 3706, the adhesive layer 3742 and the printed electrode 3730 are assembled together such that a multilayered, substantially planar electrode assembly is formed, in which a conductive path is established from the conductive pathway, via the stitched region 3740 and the conductive fabric segment 3744, to the printed electrode 3730.

Figure 47:
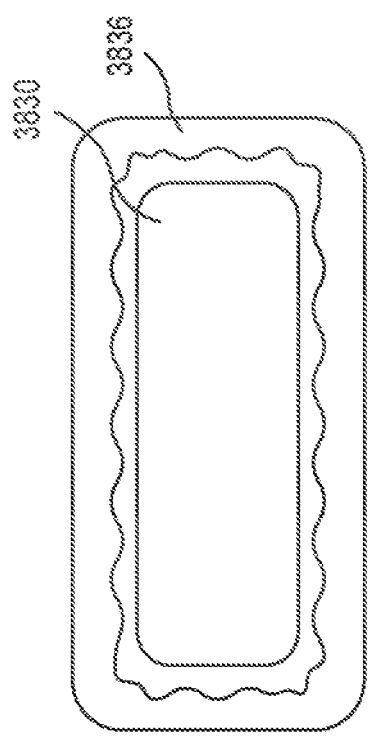
FIG. 47 shows a plan view of a solid frame overlapping an electrode, according to an embodiment.

FIG. 47 shows a plan view of a solid frame 3836 overlapping (e.g., disposed on top of) an electrode 3830, according to an embodiment.

Figure 48A:
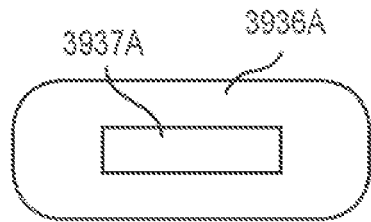
FIGS. 48A-48F show examples of solid frame shapes, according to some embodiments.
Figure 48B:
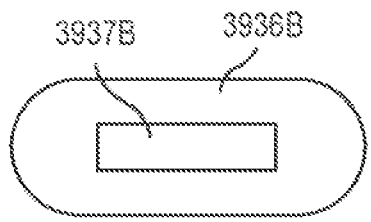
Figure 48C:
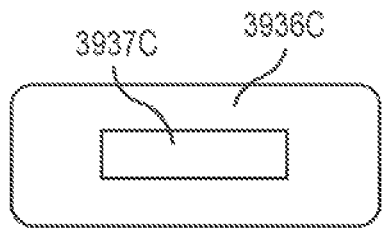
Figure 48D:
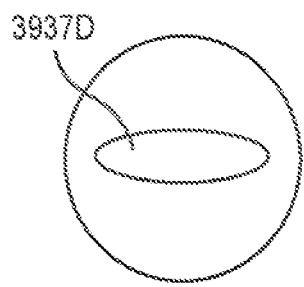
Figure 48E:
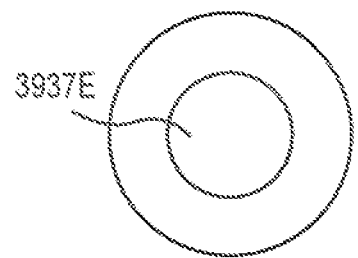
Figure 48F:
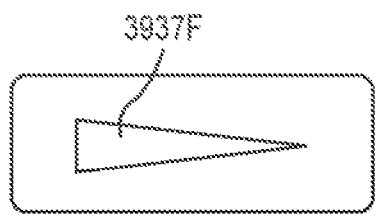

FIGS. 48A-48F show examples of solid frame shapes, according to some embodiments. As shown in FIG. 48A, a solid frame 3936A has a substantially oval outer perimeter shape that is substantially rectangular but with circular/rounded corners, and a substantially rectangular inner perimeter shape. In other words, a substantially rectangular closed recess 3937A is defined by the frame 3936A. FIG. 48B shows a solid frame 3936B having a substantially oval outer perimeter shape with two opposing semi-circular ends and a substantially rectangular inner perimeter shape. Said another way, frame 3936B has corners with a larger radius of curvature than a radius of curvature of the corners of frame 3936A. A substantially rectangular closed recess 3937B is defined by the frame 3936B. FIG. 48C shows a solid frame 3936C having a substantially oval outer perimeter shape that is substantially rectangular but with circular/rounded corners. Said another way, frame 3936C has corners with a smaller radius of curvature than a radius of curvature of the corners of frame 3936A. A substantially rectangular closed recess 3937C is defined by the frame 3936C. In other embodiments, a central recess of a frame can have a substantially oval, circular, or triangular shape (shown in FIGS. 48D, 48E and 48F, respectively, at 3937D, 3937E and 3937F, respectively), and/or a frame can have a substantially circular (shown in FIGS. 48D and 48E) or triangular (shown in FIG. 48F) shape. Any combination of the aforementioned shapes, as well as variations thereof, are also contemplated. For example, the shape of the outer perimeter of the frame and the shape of the perimeter of the recess defined by the frame can be of the same or different shapes.

Figure 49:
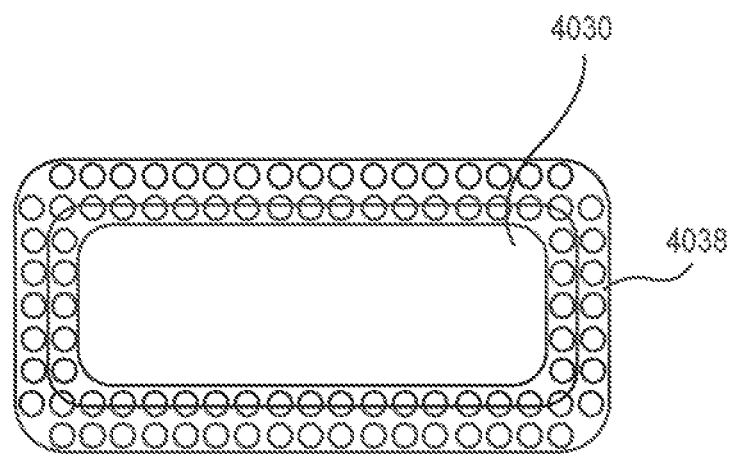
FIG. 49 shows a plan view of a perforated frame overlapping an electrode, according to an embodiment.

FIG. 49 shows a plan view of a perforated frame 4038 overlapping an electrode 4030, according to an embodiment. Perforated frame 4038 can be produced, for example, by removing a plurality of portions of a solid frame (such as frame 3836 of FIG. 47). The removed portions can each have a shape that is substantially circular, as shown in FIG. 49, or any other suitable shape, such as square, rectangular, linear strips, etc. The perforated frame 4038 includes less surface area than a solid frame of equivalent dimensions, and may be desirable, e.g., for added flexibility when disposed on a fabric substrate.

Figure 50:
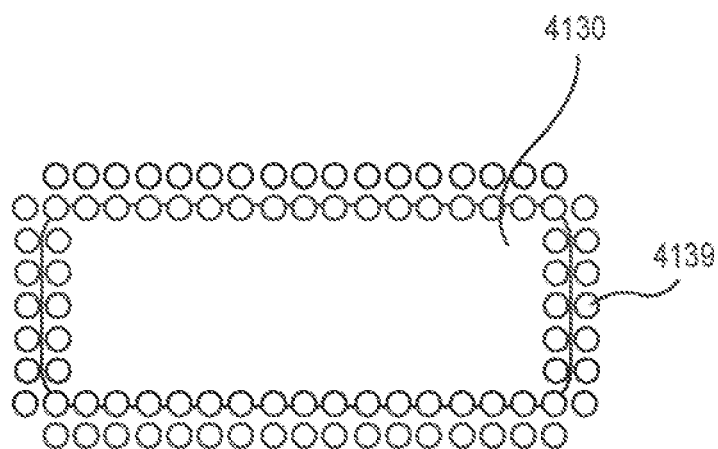
FIG. 50 shows a plan view of a patterned frame overlapping an electrode, according to an embodiment.

FIG. 50 shows a plan view of a patterned frame 4139 (i.e., a configuration that is substantially the inverse of that shown in FIG. 49) overlapping an electrode 4130, according to an embodiment. Patterned frame 4139 can be produced, for example, by removing a region of a solid frame (such as frame 3836 of FIG. 47) such that a plurality of portions of the frame remain. The remaining portions can each have a shape that is substantially circular, as shown in FIG. 50, or any other suitable shape, such as square, rectangular, linear strips, etc. Like the perforated frame 4038 of FIG. 49, the patterned frame 4139 includes less surface area than a solid frame of equivalent dimensions, and may be desirable, e.g., for added flexibility when disposed on a fabric substrate.

As used herein, the term "filament" refers to any elongate material that is suitable for weaving, and may refer to a fiber, thread, yarn, wire, and/or the like. An individual filament can include a single strand of material or a cohesive plurality of strands.

As used herein, the term "knit" or "knitted" refers to layers, portions, or components included in a textile-based electrode system that are formed by interlacing filaments (e.g., yarn or threads) in a series of connected loops with needles.

As used herein, the terms "about" and "approximately" generally mean plus or minus 10% of the value stated, for example about 250 μm would include 225 μm to 275 μm, about 1,000 μm would include 900 μm to 1,100 μm.

As used herein, the term "electrode" refers to an electrical conductor configured to contact a non-metallic surface including a skin of a user (e.g., a human or an animal) and measure electrical signals corresponding to one or more physiological parameters of the user.

As used herein, the term "conformal" or "conformality" refers to the ability of an object (e.g., an electrode) to conform to a surface (e.g., the skin of a wearer). "Highly conformal" or "high conformality" means that the object has or takes on a shape that substantially matches the shape of an underlying surface to which it is applied, for example, such that the object and the surface are in close contact or are touching over substantially the entirety of the interface therebetween.

While various embodiments of the system, methods and devices have been described above, it should be understood that they have been presented by way of example only, and not limitation. Where methods and steps described above indicate certain events occurring in a certain order, those of ordinary skill in the art having the benefit of this disclosure would recognize that the ordering of certain steps may be modified and such modification are in accordance with the variations of the invention. Additionally, certain of the steps may be performed concurrently in a parallel process when possible, as well as performed sequentially as described above. The embodiments have been particularly shown and described, but it will be understood that various changes in form and details may be made.

The invention claimed is:

1. A conductive band comprising:
an electrically conductive filament; and
a plurality of elastic members mechanically joined by the electrically conductive filament,
wherein
the conductive band having a first major longitudinal surface and a second major longitudinal surface, and
the electrically conductive filament being disposed within the conductive band such that the electrically conductive filament imparts conductivity to both the first major longitudinal surface and the second major longitudinal surface.

2. The conductive band of claim 1, wherein the electrically conductive filament is knitted, braided, crocheted, wrapped, knotted, or woven to the plurality of elastic members.

3. The conductive band of claim 1, further comprising:
a support band comprising the plurality of elastic members and a plurality of non-conductive filaments.

4. The conductive band of claim 1, wherein the plurality of elastic members are configured to be stretchable along a longitudinal axis of the conductive band.

5. The conductive band of claim 1, wherein the electrically conductive filament is configured to be stretchable along a longitudinal axis of the conductive band.

6. The conductive band of claim 1, wherein the second major longitudinal surface is opposite the first major longitudinal surface.

7. The conductive band of claim 1, further comprising:
an electrode to detect signals of electrocardiogram (ECG) signals and electromyography (EMG) signals from a skin of a wearer of the conductive band.

8. The conductive band of claim 1, wherein the conductive band has a cross-sectional shape selected from one of: a flat cross-sectional shape, a round cross-sectional shape, or a oval cross-sectional shape.

9. A conductive band comprising:
an electrically conductive filament; and
one or more elastic members mechanically joined to the electrically conductive filament, wherein:
the conductive band having a first major longitudinal surface and a second major longitudinal surface, and
the electrically conductive filament being configured to impart conductivity to the first major longitudinal surface and the second major longitudinal surface of the conductive band.

10. The conductive band of claim 9, wherein the electrically conductive filament is knitted, braided, crocheted, wrapped, knotted, or woven to the one or more elastic members.

11. The conductive band of claim 9, further comprising:
a support band comprising the one or more elastic members and a plurality of non-conductive filaments.

12. The conductive band of claim 9, wherein the one or more elastic members are configured to be stretchable along a longitudinal axis of the conductive band.

13. The conductive band of claim 9, wherein the electrically conductive filament is configured to be stretchable along a longitudinal axis of the conductive band.

14. The conductive band of claim 9, wherein the second major longitudinal surface is opposite the first major longitudinal surface.

15. The conductive band of claim 9, further comprising:
an electrode to detect signals of electrocardiogram (ECG) signals and electromyography (EMG) signals from a skin of a wearer of the conductive band.

16. The conductive band of claim 9, wherein the conductive band has a cross-sectional shape selected from one of: a flat cross-sectional shape, a round cross-sectional shape, or a oval cross-sectional shape.

17. A conductive band comprising:
one or more elastic members;
an electrically conductive filament mechanically joined to the one or more elastic members;
an electrode in electrical communication with the electrically conductive filament;
a first major longitudinal surface; and
a second major longitudinal surface opposite the first major longitudinal surface, wherein:
the electrically conductive filament being configured to impart conductivity to both the first major longitudinal surface and the second major longitudinal surface of the conductive band, and the one or more elastic members being configured to cause the electrode to be maintained in contact with skin of a wearer of the conductive band during use of the conductive band.

18. The conductive band of claim 17, further comprising: a support band comprising a plurality of elastic members and a plurality of non-conductive filaments.

19. The conductive band of claim 17, wherein the one or more elastic members and the electrically conductive filament are configured to be stretchable along a longitudinal axis of the conductive band.

20. The conductive band of claim 17, wherein the electrode is configured to detect signals of electrocardiogram (ECG) signals and electromyography (EMG) signals from a skin of a wearer of the conductive band.

* * * * *